United States Patent
Sadeque et al.

(10) Patent No.: US 11,555,015 B2
(45) Date of Patent: Jan. 17, 2023

(54) COMPOUNDS USEFUL IN THE TREATMENT OF AUTOIMMUNE AND INFLAMMATORY DISORDERS

(71) Applicant: Arena Pharmaceuticals, Inc., San Diego, CA (US)

(72) Inventors: Abu J. M. Sadeque, San Diego, CA (US); Daniel J. Buzard, San Diego, CA (US)

(73) Assignee: Arena Pharmaceuticals, Inc., New York, NY (US)

( * ) Notice: Subject to any disclaimer, the term of this patent is extended or adjusted under 35 U.S.C. 154(b) by 0 days.

(21) Appl. No.: 17/273,681

(22) PCT Filed: Sep. 5, 2019

(86) PCT No.: PCT/US2019/049822
§ 371 (c)(1),
(2) Date: Mar. 4, 2021

(87) PCT Pub. No.: WO2020/051378
PCT Pub. Date: Mar. 12, 2020

(65) Prior Publication Data
US 2021/0340104 A1 Nov. 4, 2021

Related U.S. Application Data

(60) Provisional application No. 62/727,970, filed on Sep. 6, 2018, provisional application No. 62/783,875, filed on Dec. 21, 2018, provisional application No. 62/803,190, filed on Feb. 8, 2019, provisional application No. 62/816,368, filed on Mar. 11, 2019.

(51) Int. Cl.
*C07D 209/94* (2006.01)
*C07H 15/26* (2006.01)

(52) U.S. Cl.
CPC ............ *C07D 209/94* (2013.01); *C07H 15/26* (2013.01)

(58) Field of Classification Search
None
See application file for complete search history.

(56) References Cited

U.S. PATENT DOCUMENTS

| | | |
|---|---|---|
| 3,206,470 A | 9/1965 | William et al. |
| 4,057,559 A | 11/1977 | Asselin et al. |
| 4,782,076 A | 11/1988 | Mobilio et al. |
| 4,810,699 A | 3/1989 | Sabatucci et al. |
| 5,221,678 A | 6/1993 | Atkinson et al. |
| 5,776,967 A | 7/1998 | Kreft et al. |
| 5,830,911 A | 11/1998 | Failli et al. |
| 6,410,583 B1 | 6/2002 | Labelle et al. |
| 6,960,692 B2 | 11/2005 | Kohno et al. |
| 7,250,441 B2 | 7/2007 | Gopalsamy et al. |
| 8,415,484 B2 * | 4/2013 | Jones ............. A61P 11/06 548/428 |
| 8,580,841 B2 | 11/2013 | Jones et al. |
| 8,853,419 B2 | 10/2014 | Montalban et al. |
| 9,085,581 B2 | 7/2015 | Jones et al. |
| 9,108,969 B2 | 8/2015 | Jones et al. |
| 9,126,932 B2 | 9/2015 | Jones et al. |
| 9,175,320 B2 | 11/2015 | Montalban et al. |
| 9,447,041 B2 | 9/2016 | Montalban et al. |
| 9,522,133 B2 | 12/2016 | Jones et al. |
| 11,149,292 B2 | 10/2021 | Montalban et al. |
| 2003/0083269 A1 | 5/2003 | Brouillette et al. |
| 2003/0211421 A1 | 11/2003 | Hanabata et al. |
| 2004/0224941 A1 | 11/2004 | Seko et al. |
| 2004/0254222 A1 | 12/2004 | Kohno et al. |

(Continued)

FOREIGN PATENT DOCUMENTS

| | | |
|---|---|---|
| EP | 0468785 | 1/1992 |
| EP | 1650186 | 4/2006 |
| EP | 1826197 | 8/2007 |
| EP | 2003132 | 12/2008 |
| EP | 1772145 | 3/2011 |

(Continued)

OTHER PUBLICATIONS

Arbiser, "Why targeted therapy hasn't worked in advanced cancer," J. Clinical Invest., Oct. 2007, 117(10):2762-2765.
Balatoni et al., "FTY720 sustains and restores neuronal function in the DA rat model of MOG-induced experimental autoimmunue encephalomyelitis," Brain Res. Bull., 2007, 74:307-316.

(Continued)

*Primary Examiner* — Traviss C McIntosh, III
(74) *Attorney, Agent, or Firm* — Fish & Richardson P.C.

(57) ABSTRACT

The present invention relates to certain compounds of Formula (Ia) and pharmaceutically acceptable salts thereof, which exhibit useful pharmacological properties, for example, as agonists of the S1P1 receptor: Also provided by the present invention are pharmaceutical compositions containing compounds of the invention, and methods of using the compounds and compositions of the invention in the treatment of S1P1 receptor-associated disorders, for example, a disease or disorder mediated by lymphocytes, an autoimmune disease or disorder, an inflammatory disease or disorder, an inflammatory skin disease or disorder, cancer, psoriasis, atopic dermatitis, rheumatoid arthritis, Crohn's disease, transplant rejection, multiple sclerosis, systemic lupus erythematosus, ulcerative colitis, type I diabetes, and acne, microbial infections or diseases and viral infections or diseases.

(Ia)

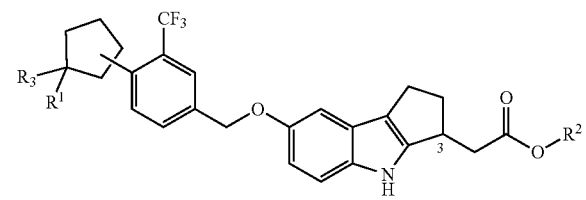

15 Claims, 11 Drawing Sheets

(56) References Cited

U.S. PATENT DOCUMENTS

| | | |
|---|---|---|
| 2005/0004114 A1 | 1/2005 | Whitehouse et al. |
| 2005/0009786 A1 | 1/2005 | Pan et al. |
| 2005/0014724 A1 | 1/2005 | Marsilje et al. |
| 2005/0014725 A1 | 1/2005 | Mi et al. |
| 2005/0014728 A1 | 1/2005 | Pan et al. |
| 2005/0033055 A1 | 2/2005 | Bugianesi et al. |
| 2005/0239899 A1 | 10/2005 | Fecke et al. |
| 2006/0004010 A1 | 1/2006 | Habashita et al. |
| 2006/0063821 A1 | 3/2006 | Gopalsamy et al. |
| 2006/0079542 A1 | 4/2006 | Nestor |
| 2006/0122222 A1 | 6/2006 | Whitehouse et al. |
| 2006/0160771 A1 | 7/2006 | Kohno et al. |
| 2006/0211656 A1 | 9/2006 | Albert et al. |
| 2006/0223866 A1 | 10/2006 | Evindar et al. |
| 2007/0010494 A1 | 1/2007 | Ehrhardt et al. |
| 2007/0043014 A1 | 2/2007 | Doherty et al. |
| 2007/0060573 A1 | 3/2007 | Wortmann et al. |
| 2007/0149595 A1 | 6/2007 | Tanaka et al. |
| 2007/0149597 A1 | 6/2007 | Nishi et al. |
| 2007/0167425 A1 | 7/2007 | Nakade et al. |
| 2007/0173487 A1 | 7/2007 | Saha et al. |
| 2007/0173507 A1 | 7/2007 | Hirata |
| 2007/0191313 A1 | 8/2007 | Beard et al. |
| 2007/0191371 A1 | 8/2007 | Bennett et al. |
| 2007/0191468 A1 | 8/2007 | Nishi et al. |
| 2007/0244155 A1 | 10/2007 | Sharma et al. |
| 2007/0254886 A1 | 11/2007 | Habashita et al. |
| 2008/0051418 A1 | 2/2008 | Maekawa et al. |
| 2008/0153882 A1 | 6/2008 | Nishi et al. |
| 2008/0200535 A1 | 8/2008 | Ohmori et al. |
| 2008/0207584 A1 | 8/2008 | Habashita et al. |
| 2008/0319077 A1 | 12/2008 | Suzuki et al. |
| 2009/0012093 A1 | 1/2009 | Fukatsu et al. |
| 2009/0076070 A1 | 3/2009 | Harada et al. |
| 2009/0131438 A1 | 5/2009 | Ono et al. |
| 2009/0137685 A1 | 5/2009 | Kojima et al. |
| 2009/0325907 A1 | 12/2009 | Kohno et al. |
| 2010/0267778 A1 | 10/2010 | Kusuda et al. |
| 2010/0273806 A1 | 10/2010 | Jones et al. |
| 2010/0292233 A1 | 11/2010 | Jones et al. |
| 2011/0086810 A1 | 4/2011 | Rodgers et al. |
| 2011/0130409 A1 | 6/2011 | Jones et al. |
| 2011/0160243 A1 | 6/2011 | Jones et al. |
| 2012/0064060 A1 | 3/2012 | Habashita et al. |
| 2012/0295947 A1 | 11/2012 | Montalban et al. |
| 2012/0329848 A1 | 12/2012 | Jones et al. |
| 2013/0184307 A1 | 7/2013 | Jones et al. |
| 2014/0038987 A1 | 2/2014 | Jones et al. |
| 2014/0357690 A1 | 12/2014 | Montalban et al. |
| 2015/0284399 A1 | 10/2015 | Jones et al. |
| 2015/0335618 A1 | 11/2015 | Jones et al. |
| 2015/0336966 A1 | 11/2015 | Jones et al. |
| 2016/0016904 A1 | 1/2016 | Montalban et al. |
| 2017/0159088 A1 | 6/2017 | Montalban et al. |
| 2017/0217885 A1 | 8/2017 | Jones et al. |
| 2019/0135752 A1 | 5/2019 | Jones et al. |
| 2020/0407316 A1 | 12/2020 | Jones et al. |

FOREIGN PATENT DOCUMENTS

| | | |
|---|---|---|
| EP | 2017263 | 11/2011 |
| GB | 1436893 | 5/1976 |
| JP | 2007262009 | 10/2007 |
| WO | WO 9106537 | 5/1991 |
| WO | WO 9714674 | 4/1997 |
| WO | WO 0064888 | 11/2000 |
| WO | WO 0239987 | 5/2002 |
| WO | WO 0264616 | 8/2002 |
| WO | WO 02092068 | 11/2002 |
| WO | WO 03029205 | 4/2003 |
| WO | WO 03062252 | 7/2003 |
| WO | WO 03073986 | 9/2003 |
| WO | WO 03074008 | 9/2003 |
| WO | WO 03061567 | 12/2003 |
| WO | WO 03105771 | 12/2003 |
| WO | WO 200405 8149 | 9/2004 |
| WO | WO 2004074297 | 9/2004 |
| WO | WO 2004010949 | 10/2004 |
| WO | WO 2004071442 | 10/2004 |
| WO | WO 2004096752 | 11/2004 |
| WO | WO 2004096757 | 11/2004 |
| WO | WO 2004103279 | 12/2004 |
| WO | WO 2004103306 | 12/2004 |
| WO | WO 2004103309 | 12/2004 |
| WO | WO 2004104205 | 12/2004 |
| WO | WO 2004110979 | 12/2004 |
| WO | WO 2004113330 | 12/2004 |
| WO | WO 2005000833 | 1/2005 |
| WO | WO 2005021503 | 3/2005 |
| WO | WO 2005020882 | 4/2005 |
| WO | WO 2005032465 | 4/2005 |
| WO | WO 2005041899 | 5/2005 |
| WO | WO 2005044780 | 5/2005 |
| WO | WO 2005058848 | 6/2005 |
| WO | WO 2005070886 | 8/2005 |
| WO | WO 2005079788 | 9/2005 |
| WO | WO 2005082089 | 9/2005 |
| WO | WO 2005082841 | 9/2005 |
| WO | WO 2005085179 | 9/2005 |
| WO | WO 2005097745 | 10/2005 |
| WO | WO 2005058295 | 11/2005 |
| WO | WO 2005123677 | 12/2005 |
| WO | WO 2006001463 | 1/2006 |
| WO | WO 2006009092 | 1/2006 |
| WO | WO 2006010379 | 2/2006 |
| WO | WO 2006011554 | 2/2006 |
| WO | WO 2006013948 | 2/2006 |
| WO | WO 2006020951 | 2/2006 |
| WO | WO 2006010544 | 3/2006 |
| WO | WO 2006034337 | 3/2006 |
| WO | WO 2006043149 | 4/2006 |
| WO | WO 2006047195 | 5/2006 |
| WO | WO 2006064757 | 6/2006 |
| WO | WO 2006079406 | 8/2006 |
| WO | WO 2006088944 | 8/2006 |
| WO | WO 2006100631 | 9/2006 |
| WO | WO 2006100633 | 9/2006 |
| WO | WO 2006100635 | 9/2006 |
| WO | WO 2006063033 | 11/2006 |
| WO | WO 2006131336 | 12/2006 |
| WO | WO 2006137019 | 12/2006 |
| WO | WO 2006137509 | 12/2006 |
| WO | WO 2007024922 | 3/2007 |
| WO | WO 2007037196 | 4/2007 |
| WO | WO 2007060626 | 5/2007 |
| WO | WO 2007080542 | 7/2007 |
| WO | WO 2007083089 | 7/2007 |
| WO | WO 200709263 8 | 8/2007 |
| WO | WO 2007085451 | 8/2007 |
| WO | WO 2007086001 | 8/2007 |
| WO | WO 2007091396 | 8/2007 |
| WO | WO 2007091501 | 8/2007 |
| WO | WO 2007098474 | 8/2007 |
| WO | WO 2007100617 | 9/2007 |
| WO | WO 2007109330 | 9/2007 |
| WO | WO 2007109334 | 9/2007 |
| WO | WO 2007115 820 | 10/2007 |
| WO | WO 2007095561 | 10/2007 |
| WO | WO 2007116866 | 10/2007 |
| WO | WO 200706145 8 | 11/2007 |
| WO | WO 2007092190 | 11/2007 |
| WO | WO 2007129473 | 11/2007 |
| WO | WO 2007129745 | 11/2007 |
| WO | WO 2007132307 | 11/2007 |
| WO | WO 2008016674 | 2/2008 |
| WO | WO 2008018427 | 2/2008 |
| WO | WO 2008019090 | 2/2008 |
| WO | WO 2008023783 | 2/2008 |
| WO | WO 2008024196 | 2/2008 |
| WO | WO 2008016692 | 3/2008 |
| WO | WO 2008028937 | 3/2008 |
| WO | WO 2008029371 | 3/2008 |
| WO | WO 2008030843 | 3/2008 |
| WO | WO 2008035239 | 3/2008 |

(56) References Cited

FOREIGN PATENT DOCUMENTS

| WO | WO 2008029306 | 5/2008 |
|---|---|---|
| WO | WO 2008074820 | 6/2008 |
| WO | WO 2008074821 | 6/2008 |
| WO | WO 2008076356 | 6/2008 |
| WO | WO 2008079382 | 7/2008 |
| WO | WO 2008089015 | 7/2008 |
| WO | WO 2008091967 | 7/2008 |
| WO | WO 2008114157 | 9/2008 |
| WO | WO 2008128951 | 10/2008 |
| WO | WO 2008097819 | 11/2008 |
| WO | WO 2008152149 | 12/2008 |
| WO | WO 2009019167 | 2/2009 |
| WO | WO 2009019506 | 2/2009 |
| WO | WO 2009011850 | 3/2009 |
| WO | WO 2009064250 | 5/2009 |
| WO | WO 2009078983 | 6/2009 |
| WO | WO 2009094157 | 7/2009 |
| WO | WO 2009103552 | 8/2009 |
| WO | WO 2009151529 | 12/2009 |
| WO | WO 2009151621 | 12/2009 |
| WO | WO 2009151626 | 12/2009 |
| WO | WO 2010011316 | 1/2010 |
| WO | WO 2010027431 | 3/2010 |
| WO | WO 2010093704 | 8/2010 |
| WO | WO 2011005290 | 1/2011 |
| WO | WO 2011005295 | 1/2011 |
| WO | WO 2011059784 | 5/2011 |
| WO | WO 2011094008 | 8/2011 |
| WO | WO 2011109471 | 9/2011 |
| WO | WO 2012015758 | 2/2012 |

OTHER PUBLICATIONS

Bar-Haim et al., "Interrelationship between Dendritic Cell Trafficking and Francisella tularensis Dissemination following Airway Infection," PLoS Pathogens, 2008, 4(11):e1000211, 15 pages.

Baumruker et al., "FTY720, an immunomodulatory sphingolipid mimetic: translation of a novel mechanism into clinical benefit in multiple sclerosis," Expert Opin. Investig. Drugs, 2007, 16(3):283-289.

Berge et al., "Pharmaceutical Salts," J. Pharma. Sci., 1977, 66(1): 1-19.

Biopharmatiques.com [online], "Merging Pharma and Biotech—Clinical Studies of Product ACT-128800 (Sphingosine-1-phosphate (S1P1) receptor agonist)", Dec. 8, 2009, retrieved on Apr. 20, 2012, retrieved from URL <http://www.biopharmaceutiques.com/fr/tables/clinical_studies_709.html>.

Boismenu et al., "Insights from mouse models of colitis," Journal of Leukocyte Biology, 2000, 67:267-278.

Bolick et al., "Sphingosine-1-Phosphate Prevents Tumor Necrosis Factor-60 -Mediated Monocyte Adhesion to Aortic Endothelium in Mice," Arterioscler. Thromb. Vasc. Biol., 2005, 25:976-981.

Brinkmann et al., "FTY720 Alters Lymphocyte Homing and Protects Allografts Without Inducing General Immunosuppression," Transplantation Proc., 2001, 33:530-531.

Brinkmann et al., "FTY720: Altered Lymphocyte Traffic Results in Allograft Protection," Transplantation, Sep. 2001, 72(5):764-769.

Brinkmann et al., "The Immune Modulator FTY720 Targets Sphingosine 1-Phosphate Receptors," J. Biol. Chem., 2002, 277(24):21453-21457.

Brinkmann, "FTY720 (fingolimod) in Multiple Sclerosis: therapeutic effects in the immune and the central nervous system," British Journal of Pharmacology, 2009, 15 8: 1173-1182.

Brinkmann, "Sphingosine 1-phosphate receptors in health and disease: Mechanistic insights from gene deletion studies and reverse pharmacology," Pharmacology & Therapeutics, 2007, 115:84-105.

Budde et al., "First Human Trial of FTY720, a Novel Immunomodulator, in Stable Renal Transplant Patients," J. Am. Soc. Nephrol., 2002, 13:1073-1083.

Buzard et al., "Discovery and Characterization of Potent and Selective 4-Oxo-4-(5-(5-phenyl-1,2, 4-oxadiazol-3-yl)indolin-1-yl)butanoic acids as S1P1 Agonists", Bioorganic & Medicinal Chemistry Letters, 2011, 21(19):6013-6018.

Buzard et al., "Discovery and Characterization of Potent and Selective 4-Oxo-4-(5-(5-phenyl-1,2, 4-oxadiazol-3-yl)indolin-1-yl)butanoic acids as S1P1 Receptor Agonists", Arena Pharmaceuticals, Inc., San Diego, Ca, MEDI 099, ACS Poster, Mar. 2011, 1 page.

Buzard et al., "Discovery of APD334: Design of a Clinical Stage Functional Antagonist of the Sphingosine-1-phosphate-1 Receptor," ACS Medicinal Chemistry Letters, Nov. 2014, 5(12):1313-1317.

Buzard et al., "Recent Progress in the Development of Selective S1P1 Receptor Agonists for the Treatment of Inflammatory and Autoimmune Disorders," Expert Opinion on Therapeutic Patents, 2008, 18(10): 1141-1159.

Chawla et al., "Challenges in Polymorphism of Pharmaceuticals," CRIPS, Jan.-Mar. 2004, 5(1): 12-15.

Chiba et al., "Role of Sphingosine 1-Phosphate Receptor Type 1 in Lumphocyte Egress from Secondary Lymphoid Tissues and Thymus," Cell. & Mole. Immunol., Feb. 2006, 3(1): 11-19.

Chiba, "FTY720, a new class of immunomodulator, inhibits lymphocyte egress from secondary lymphoid tissues and thymus by agonistic activity at sphingosine 1-phosphate receptors," Pharmacology & Therapeutics, 2005, 108:308-319.

Chun et al., "International Union of Pharmacology. XXXIV. Lysophospholipid Receptor Nomenclature," Pharmacol. Rev., 2002, 54(2):265-269.

ClinicalTrials.gov [online], "Multicenter, Randomized, Double-blind, Placebo-controlled, Phase IIa Study to Evaluate the Efficacy, Safety, and Tolerability of ACT-128800, an S1P1 Receptor Agonist, Administered for 6 Weeks to Subjects With Moderate to Severe Chronic Plaque Psoriasis," Feb. 2009, retrieved from URL <http://clinicaltrials.gov/ct2/show/NCT0085267Q>.

Coelho et al., "The Immunomodulator FTY720 has a direct cytoprotective effect in oligodendrocyte Progenitors," J. Pharmacol. Exp, Ther., 2007, 323:626-635.

Collier et al., "Radiosynthesis and In-vivo Evaluation of the Psuedopeptide 8-pioid Antagonist [125I]-ITIPP($\Psi$)," J. Labelled Compd. Radiopharm., 1999, 42:S264-S266.

Coste et al., "Antinociceptive activity of the SIP-receptor agonist FTY720," Journal of Cellular and Molecular Medicine, 2008, 12(3):995-1004.

Daniel et al., "FTY720 Ameliorates Th1-Mediated Colitis in Mice by Directly Affecting the Functional Activity of DC4+CD25+ Regulatory T Cell1," J. Immunol., 2007, 178:2458-2468.

Deguchi et al., "The S1P receptor modulator FTY720 prevents the development of experimental colitis in mice," Oncology Reports, 2006, 16:699-703.

Dev et al., "Brain sphingosine-1-phosphate receptors: Implication for FTY720 in the treatment of multiple sclerosis," Pharmacology and Therapeutics, 2008, 117:77-93.

DrHoffman.com [online], "Crohn's disease and ulcerative colitis," Sep. 1995, retrieved from URL <https://drhoffman.com/article/crohns-disease-and-ulcerative-colitis-2/?msclkid=bbf781eccfa511ec8773c07b7fb4d777>, 5 pages.

Fischer et al., "Targeting receptor tyrosine kinase signalling in small cell lung cancer (SCLC): What have we learned so far?" Cancer Treatment Revs., 2007, 33:391-406.

Fu et al., "Long-term islet graft survival in streptozotocin- and autoimmune-induced diabetes models by immunosuppressive and potential insulinotropic agent FTY720," Transplantation, May 2002, 73(9): 1425-1430.

Fujii et al., "FTY720 suppresses CD4+CD44highCD62L-effector memory T cell-mediated colitis," Am. J. Physiol. Gastrointest. Liver Physiol., 2006, 291:G267-G274.

Fujino et al., "Amerlioration of Experimental Autoimmune Encephalomyelitis in Lewis Rats by FTY720 Treatment," J. Pharmacol. Exp. Ther., 2003, 305(1):70-77.

(56) References Cited

OTHER PUBLICATIONS

Fujishiro et al., "Change from Cyclosporine to Combination Therapy of Mycophenolic Acid with the New Sphinogosine-1-phosphate Receptor Agonist, KRP-203, Prevents Host Nephrotoxicity and Transplant Vasculopathy in Rats," J. Heart Lung Transplant, 2006, 25:825-833.
Gabriel et al., "High Throughput Screening Technologies for Direct Cyclic AMP Measurement," ASSAY and Drug Development Technologies, 2003, 1:291-303.
Golub et al., "Molecular Classification of Cancer: Class Discovery and Class Prediction by Gene Expression Monitoring," Science, 1999, 286:531-537.
Gottlieb et al., "NMR Chemical Shifts of Common Laboratory Solvents as Trace Impurities," J. Org. Chem. 1997, 62:7512-7515.
Griesser, "The Importance of Solvates," Polymorphism: in the Pharmaceutical Industry, 2006, pp. 211-233.
Groeneveld, "Vascular pharmacology of acute lung injury and acute respiratory distress syndrome," Vascular Pharmacol., 2003, 39:247-256.
Guillory, "Generation of Polymorphs, Hydrates, Solvates, and Amorphous Solids," Polymorphism in Pharmaceutical Solids, 1999, 95:202-209.
Hale et al., "Potent S1P receptor agonists replicate the pharmacologic actions of the novel immune modulator FTY720," Bioorganic & Med. Chem. Lett., 2004, 14:3351-3335.
Han et al., "Discovery of 2-(7-(5-phenyl-1,2,4-oxadiazol-3-yl)-1,2,3,4-tetrahydrocyclopenta[b]indol-3-yl)acetic acids: Potent and Selective Sphingosine-1-phosphate (S1P1) Receptor Agonists", Arena Pharmaceuticals, Inc., San Diego, CA, MEDI 098, ACS Poster, Mar. 2011, 1 page.
Herzinger et al., "Sphingosine-1-Phosphate Signaling and the Skin," Am. J. Clin. Dermatol., 2007, 8(6):329-336.
Higuchi et al., "Pro-drugs as Novel Delivery Systems," ACS Symposium Series, 1975, 14:129 pages.
Hwang et al., "FTY720, a New Immunosuppressant, Promotes Long-Term Graft Survival and Inhibits the Progression of Graft Coronary Artery Disease in a Murine Model of Cardiac Transplantation," Circulation, 1999, 100:1322-1329.
Idzko et al., "Local application of FTY720 to the lung abrogates experimental asthma by altering dendritic cell function," J. Clin. Invest., Nov. 2006, 116(11):2935- 2944.
International Preliminary Report on Patentability in International Appln. No. PCT/US2019/049822, dated Mar. 9, 2021, 8 pages.
International Search Report and Written Opinion in International Appln. No. PCT/US2019/049822, dated Oct. 29, 2019, 11 pages.
Ishii et al., "Sphingosine-1-phosphate mobilizes osteoclast precursors and regulates bone homeostasis," Nature, Mar. 2009, 458(7237):524-528.
Jones, "Discovery of Potent and Selective Sphingosine-1-Phosphate 1 (S1P1) Receptor Agonists", CHI 6th Annual Drug Discovery Chemistry, San Diego, CA, Apr. 12, 2011, 22 pages.
Jones, "Discovery of Potent and Selective Sphingosine-1-Phosphate 1(S1P1) Receptor Agonists", CHI 6th Annual Discovery on Target, Boston, MA, Nov. 3, 2011, 26 pages.
Jung et al., "Functional Consequences of SIP Receptor Modulation in Rat Oligodendroglial Lineage Cells," Glia, 2007, 55:1656-1667.
Kaneider et al., "The immune modulator FTY720 targets sphingosine-kinase-dependent migration of human monocytes in response to amyloid beta-protein and its precursor," FASEB J., 2004, 18:309-311.
Kappos et al., "Oral Fingolimod (FTY720) for Relapsing Multiple Sclerosis," N. Engl. J. Med., 2006, 355:1124-1140.
Kataoka et al., "FTY720, Sphingosine 1-Phosphate Receptor Modulator, Ameliorates Experimental Autoimmune Encephalomyelitis by Inhibition of T Cell Infiltration," Cellular & Molecular Immunology, Dec. 2005, 2(6):439-448.
Kaudel et al., "FTY720 for Treatment of Ischemia-Reperfusion Injury Following Complete Renal Ischemia; Impact on Long-Term Survival and T-Lymphocyte Tissue Infiltration," Transplantation Proc., 2007, 39:499-502.
Kawasaki et al., "Discovery and Characterization of 2-(7-(5-phenyl-1,2,4-oxadiazol-3-yl)-2,3-dihydro-1H-pyrrolo[1,2-a]indol-1-yl)acetic acid Derivatives as Potent & Selective Human S1P1 Receptor Agonists," Arena Pharmaceuticals, Inc., San Diego, CA, MEDI 254, ACS Poster, Mar. 2011, 1 page.
Keul et al., "The Sphinogosine-1-Phosphate Analogue FTY720 Reduces Atherosclerosis in Apolipoprotein E-Deficient Mice," Arterioscler. Thromb. Vasc. Biol., 2007, 27:607-613.
Kim et al., "Sphingosine-1-phosphate inhibits human keratinocyte proliferation via Akt/protein kinase B inactivation," Cellular Signalling, 2004, 16:89-95.
Kimura et al., "Essential Roles of Sphingosine 1-Phosphate/S1P1 Receptor Axis in the Migration of Neural Stem Cells Toward a Site of Spinal Cord Injury," Stem Cells, 2007, 25:115-124.
Kitabayashi et al., "FTY720 Prevents Development of Experimental Autoimmune Myocarditis Through Reduction of Circulating Lymphocytes," J. Cardiovasc. Pharmacol., 2000, 35:410-416.
Kohno et al., "A Novel Immunomodulator, FTY720, Prevents Development of Experimental Autoimmune Myasthenia Gravis in C57BL/6 Mice," Biological & Pharmaceutical Bulletin, 2005, 28(4):736-739.
Kohno et al., "A Novel Immunomodulator, FTY720, Prevents Spontaneous Dermatitis in NC/Nga Mice," Biological & Pharmaceutical Bulletin, 2004, 27(9): 1392-1396.
Koreck et al., "The Role of Innate Immunity in the Pathogensis of Acne," Dermatology, 2003, 206:96-105.
Kurose et al., "Effects of FTY720, a novel immunosuppressant, on experimental autoimmune uveoretinitis in rats," Exp. Eye Res., 2000, 70:7-15.
Lala et al., "Role of nitric oxide in tumor progression: Lessons from experimental tumors," Cancer Metastasis Rev., 1998, 17:91-106.
LaMontagne et al., "Antagonism of Sphingosine-1-Phosphate Receptors by FTY720 Inhibits Angiogenesis and Tumor Vascularization," Cancer Res., 2006, 66:221-231.
Le Bas et al., "Radioiodinated Analogs of EP 00652218 for the Exploration of the Tachykinin NK1 Receptor by Spect," J. Labelled Compl. Radiopharm., 2001, 44:S280-S282.
Lee et al., "FTY720: A Promising Agent for Treatment of Metastatic Hepatocellular Carcinoma," Clin. Cancer Res., 2005, 11:8458-8466.
Lima et al., "FTY720 Treatment Prolongs Skin Graft Survival in a Completely Incompatible Strain Combination," Transplant Proc., 2004, 36:1015-1017.
Liu et al., "Long-Term Effect of FTY720 on Lymphocyte Count and Islet Allograft Survival in Mice," Microsurgery, 2007, 27:300-304.
Lleo et al., "Etiopathogenesis of primary biliary cirrhosis," World Journal of Gastroenterology, Jun. 2008, 14(21):3328-3337.
Madhusudan et al., "Tyrosine kinase inhibitors in cancer therapy," Clinical Biochem., 2004, 37:618-635.
Maki et al., "Prevention and Cure of Autoimmune Diabetes in Nonobese Diabetic Mice by Continuous Administration of FTY720," Transplantation, 2005, 79:1051-1055.
Maki et al., "Prevention of autoimmune diabetes by FTY720 in Nonobese diabetic mice," Transplantation, Dec. 2002, 74(12): 1684-1686.
Martini et al., "Current perspectives on FTY720," Expert Opin. Investig. Drugs, 2007, 16:505-518.
Martini et al., "S1P modulator FTY720 limits matrix expansion in acute anti-thy 1 mesangioproliferative glomerulonephritis," Am. J. Physiol. Renal Physiol., 2007, 292:F1761-F1770.
Matloubian et al., "Lymphocyte egress from thymus and peripheral lymphoid organs in dependent on S1P receptor 1," Nature, Jan. 2004, 427:355-360.
Matsuura et al., "Effect of FTY720, a novel immunosuppressant, on adjuvant- and collagen-induced arthritis in rats," Int. J. Immunopharmacol., 2000, 22:323-331.
Matsuura et al., "Effect of FTY720, a novel immunosuppressant, on adjuvant-induced arthritis in rats," Inflamm. Res. 2000, 49:404-410.
Miron et al., "FTY720 Modulates Human Oligodendrocyte Progenitor Process Extension and Survival," Ann. Neurol., 2008, 63:61-71.

(56) References Cited

OTHER PUBLICATIONS

Miyamoto et al., "Therapeutic Effects of FTY720, a New Immunosuppressive Agent, in a Murine Model of Acute Viral Myocarditis," J. Am. Coll. Cardiol., 2001, 37(6): 1713-1718.
Mizushima et al., "Therapeutic Effects of a New Lymphocyte Homing Reagent FTY720 in Interleukin-10 Gene-deficient Mice with Colitis," Inflamm. Bowel Dis., May 2004, 10(3): 182-192.
Morissette, et al., "High-Throughput Crystallization: Polymorphs, Salts, Co-Crystals and Solvates of Pharmaceutical Solids", Adv. Drug Delivery Rev., 2004, 56:275-300.
Nakashima et al., "Impaired Initiation of Contact Hypersensitivity by FTY720," J. Investigative Dermatology, 2008, 128:2833-2841.
Neurath et al., "Antibodies to Interleukin 12 Abrogate Established Experimental Colitis in Mice," J. Exp. Med. 1995, 182:1281-1290.
Newman et al., "Solid-state analysis of active pharmaceutical ingredient in drug products," DDT, Oct. 2003, 8(19):898-905.
Nofer et al., "FTY720, a Synthetic Sphingosine 1 Phosphate Analogue, Inhibits Development of Atherosclerosis in Low-Density Lipoprotein Receptor Deficient Mice," Circulation, 2007, 115:501-508.
Ogawa et al., "A novel sphingosine-1-phosphate receptor agonist KRP-203 attenuates rate autoimmune myocarditis," Biochem, Biophys. Res. Commun., 2007, 361:621-628.
Okayasu et al., "A Novel Method in the Induction of Reliable Experimental Acute and Chronic Ulcerative Colitis in Mice," Gastroenterology, 1990, 98:694-702.
Okazaki et al., "Effects of FTY720 in MRL-Ipr/Ipr mice: therapeutic potential in systemic lupus erythematosus," J. Rheumatol., 2002, 29:707-716.
Oo et al., "Immunosuppressive and Anti-angiogenic Sphingosine 1-Phosphate Receptor-1 Agonists Induce Ubiquitinylation and Proteasomal Degradation of the Receptor," J. Biol. Chem., 2007, 282(12):9082-9089.
Pan et al., "A Monoselective Sphingosine-1-Phosphate Receptor-1 Agonist Prevents Allograft Rejection in a Stringent Rat Heart Transplantation Model," Chemistry & Biology, 2006, 13:1227-1234.
Pfeilschifter et al., "Treatment with immunomodulator FTY720 does not promote spontaneous bacterial infections after experimental stroke mice," Experimental Translational Stroke Med., 2011, 3(2), 6 pages.
Premenko-Lanier et al., "Transient FTY720 treatment promotes immune-mediated clearance of a chronic viral infection," Nature, Aug. 2008, 454:894-899.
Rausch et al., "Predictability of FTY720 Efficacy in Experimental Autoimmune Encephalomyelitis by In Vivo Macrophage Tracking: Clinical Implications for Ultrasmall Superparamagnetic Iron Oxide-Enhanced Magnetic Resonance Imaging," J. Magn. Reson. Imaging, 2004, 20:16-24.
Raveney et al., "Fingolimod (FTY720) as an Acute Rescue Therapy for Intraocular Inflammatory Disease," Arch. Ophthalmol., 2008, 126(10): 1390-1395.
Rosen et al., "Egress: a receptor-regulated step in lymphocyte trafficking," Immunol. Rev., 2003, 195:160-177.
Sakagawa et al., "Rejection following donor or recipient preoperative treatment with FTY720 in rat small bowel transplantation," Transpl. Immunol., 2004, 13:161-168.
Sanchez et al., "Phosphorylation and Action of the Immunomodulator FTY720 Inhibits Vascular Endothelial Cell Growth Factor-induced Vascular Permeability," J. Biol. Chem., 2003, 278(47):47281-47290.
Sanna et al., "Enhancement of capillary leakage and restoration of lymphocyte egress by a chiral S1P1 antagonist in vivo," Nature Chem. Biol., Aug. 2006, 2(8):434-441.
Sanna et al., "Sphingosine 1-Phosphate (S1P) Receptor Subtypes S1P1 and S1P3, Respectively, Regulate Lymphocyte Recirculation and Heart Rate," J. Biol Chem., 2004, 279(14): 13839-13848.
Sauer et al., "Involvement of Smad Signlaing in Sphingosine 1-Phosphate-mediated Biological Responses of Keratinocytes," J. Biol. Chem., 2004, 279:38471-38479.

Sawicka et al., "Inhibition of Th1- and Th2-Mediated Airway Inflammation by the Sphingosine 1-Phosphate Receptor Agonist FTY720," J. Immunol., 2003, 171:6206-6214.
Schmid et al., "The Immunosuppressant FTY720 inhibits tumor Angiogenesis via the Sphingosine 1-Phosphate Receptor 1," J. Cell Biochem., 2007, 101:259-270.
Schwab et al., "Finding a way out: lymphocyte egress from lymphoid organs," Nature Immunol., Dec. 2007, 8(12): 1295-1301.
ScienceDaily.com [online], "Avoiding Fatal Responses to Flu Infection," Sep. 15, 2011, retrieved from URL <http://www.sciencedaily.com/releases/2011/09/110915134410.htm> , 2 pages.
Shafiee et al., "An efficent enzyme-catalyzed kinetic resolution: large-scale preparation of an enantiomerically pure indole-ethyl ester derivative, a key component for the synthesis of a prostaglandin D2 receptor antagonist, an anti-allergic rhinitis drug candidate," Tetrahedron: Asymmetry, Sep. 2005, 16:3094-3098.
Shimizu et al., "KRP-203, a Novel Synthetic Immunosuppressant, Prolongs Graft Survival and Attenuates Chronic Rejection in Rat Skin and Heart Allografts," Circulation, 2005, 111:222-229.
Stachulski et al., "Glucuronides from metabolites to medicines: a survey of the in vivo generation, chemical synthesis and properties of glucuronides," Natural Product Reports, 2013, 30(6):806-848.
Stahly, "Diversity in Single- and Multiple-Component Crystals. The Search for and Prevalence of Polymorphs and Cocrystals," Crystal Growth & Design, 2007, 7(6): 1007-1026.
STN Search Report dated May 22, 2017, 9 pages (RN 380350-42-5, STN/CAPLUS (Year: 2002).
Storey, et al., "Automation of Solid Form Screening Procedures in the Pharmaceutical Industry—How to Avoid the Bottlenecks," Crystallography Reviews, 2004, 10(1):45-46.
Sturino et al., "Discovery of a Potent and Selective Prostaglandin D2 Receptor Antagonist, [(3R)-4-(4-Chloro- benzyl)-7-fluoro-5-(methylsulfonyl)-1,2,3,4-tetrahydrocyclopenta[b]indol-3-yl]-acetic Acid (MK-0524)," Journal of Medicinal Chemistry, 2007, 50(4):794-806.
Suzuki et al., "Efficacy of Mycophenolic Acid Combined with KRP-203, a Novel Immunomodulator, in a Rat Heart Transplantation Model," J. Heart Lung Transplant, 2006, 25:302-309.
Suzuki et al., "Immunosuppressive effect of anew drug, FTY720, on lymphocyte responses in vitro and cardiac allograft survival in rats," Transplant Immunol., 1996, 4:252-255.
Taylor et al., "Insights into the mechanism of FTY720 and compatibility with regulatory T cells for the inhibition of graft-versus-host disease (GVHD)," Blood, 2007, 110:3480-3488.
Truong et al., "Human Islet Function is not Impaired by the Sphingosine-1-Phosphate Receptor Modulator FTY720," American Journal of Transplantation, 2007, 7:2031-203 8.
Truppo et al., "Optimization and Scale-Up of a Lipase-Catalyzed Enzymatic Resolution of an Indole Ester Intermediate for a Prostaglandin D2 (DP) Receptor Antagonist Targeting Allergic Rhinitis," Organic Process Research and Development, Feb. 2006, 10(3):592-598.
Vachal et al., "Highly selective and potent agonists of sphinogosin-1-phosphate 1 (S1P1) receptor," Bioorganic Med. Chem. Lett., Jul. 2006, 16(14):3684-3687.
Valdimarsson et al., "Psoriasis—as an autoimmune disease caused by molecular mimicry," Trends in Immunology, Oct. 2009, 30(10):494-501.
Villullas et al., "Characterisation of a Sphingosine 1-Phosphate-Activated Ca2+ Signalling Pathway in Human Neuroblastoma Cells," J. Neurosci. Res, 2003, 73:215-226.
Vippagunta et al., "Crystalline Solids," Adv. Drug Delivery Rev., 2001, 48:3-26.
Webb et al., "Sphingosine 1-phosphate receptors agonists attenuate relapsing—remitting experimental autoimmune encephalitis in SJL mice," J. Neuroimmunol., 2004, 153:108-121.
WebMD.com [online], "Most Common Types of Arthritis," 2012, retrieved from URL <http://www.webmd.com/rheumatoid-arthritis/guide/most-common-arthritis-types>, 2 pages.
Webster, "The Pathophysiology of Acne," Cutis, 2005, 76(suppl. 2):4-7.
Whetzel et al.,"Sphingosine-1 Phosphate Prevents Monocyte/Endothelial Interactions in Type 1 Diabetic NOD Mice Through Activation of the S1P1 Receptor," Circ. Res., 2006, 99:731-739.

(56) References Cited

OTHER PUBLICATIONS

Wikipedia.org [online], "Fingolimod," available on or before Sep. 13, 2006, retrieved on Jul. 22, 2014, retrieved from URL <http://en.wikipedia.org/wiki/Fingolimod>, 6 pages.

Yan et al., "Discovery of 3-arylpropionic acids as potent agonists of sphingosine-1-phosphate receptor-1 (S1P1) with high selectivity against all other known S1P receptor subtypes," Bioorg, & Med. Chem. Lett., 2006, 16:3679-3683.

Yanagawa et al., "FTY720, a novel immunosuppressant, induces sequestration of circulating mature lymphocytes by acceleration of lymphocyte homing in rats. II. FTY720 prolongs skin allograft survival by decreasing T cell infiltration into grafts but not cytokine production in vivo," J. Immunol., 1998, 160:5493-5499.

Yang et al., "The immune modulator FYT720 prevents autoimmune diabetes in nonobese diabetic mice," Clinical Immunology, 2003, 107:30-35.

Zhang et al., "FTY720 attenuates accumulation of EMAP-11+ and MHC-II+ monocytes in early lesions of rat traumatic brain injury," J. Cell. Mol. Med., 2007, 11(2):307-314.

Zhang et al., "FTY720: A Most Promising Immunosuppressant Modulating Immune Cell Functions," Mini-Reviews in Medicinal Chemistry, 2007, 7:845-850.

Zhu et al, "Synthesis and Mode of Action of 125I-and 3H-Labeled Thieno[2,3-c]pyridine Antagonists of Cell Adhesion Molecule Expression," J. Org. Chem., 2002, 67:943-948.

\* cited by examiner

COMPOUNDS USEFUL IN THE TREATMENT OF AUTOIMMUNE AND INFLAMMATORY DISORDERS

FIELD OF THE INVENTION

The present invention relates to certain compounds of Formula (Ia) and pharmaceutically acceptable salts thereof, which exhibit useful pharmacological properties, for example, as agonists of the S1P1 receptor. Also provided by the present invention are pharmaceutical compositions containing compounds of the invention, and methods of using the compounds and compositions of the invention in the treatment of S1P1 receptor-associated disorders, for example, a disease or disorder mediated by lymphocytes, an autoimmune disease or disorder, an inflammatory disease or disorder, an inflammatory skin disease or disorder, cancer, psoriasis, atopic dermatitis, rheumatoid arthritis, Crohn's disease, transplant rejection, multiple sclerosis, systemic lupus erythematosus, ulcerative colitis, type I diabetes, and acne, microbial infections or diseases and viral infections or diseases.

BACKGROUND OF THE INVENTION

The present invention relates to compounds that are S1P1 receptor agonists having at least immunosuppressive, anti-inflammatory and/or hemostatic activities, e.g. by virtue of modulating leukocyte trafficking, sequestering lymphocytes in secondary lymphoid tissues, and/or enhancing vascular integrity.

The present application is in part focused on addressing an unmet need for immunosuppressive agents such as may be orally available which have therapeutic efficacy for at least autoimmune diseases and disorders, inflammatory diseases and disorders (e.g., acute and chronic inflammatory conditions), transplant rejection, cancer, and/or conditions that have an underlying defect in vascular integrity or that are associated with angiogenesis such as may be pathologic (e.g., as may occur in inflammation, tumor development and atherosclerosis) with fewer side effects such as the impairment of immune responses to systemic infection.

SIP receptor agonists having agonist activity on the S1P1 receptor have been shown to rapidly and reversibly induce lymphopenia (also referred to as peripheral lymphocyte lowering (PLL); Hale et al., *Bioorg. Med. Chem. Lett.*, 14:3351-3355, 2004). This is attended by clinically useful immunosuppression by sequestering T- and B-cells in secondary lymphoid tissue (lymph nodes and Peyer's patches) and thus apart from sites of inflammation and organ grafts (Rosen et al., *Immunol. Rev.*, 195:160-177, 2003; Schwab et al., *Nature Immunol.*, 8:1295-1301, 2007). This lymphocyte sequestration, for example in lymph nodes, is thought to be a consequence of concurrent agonist-driven functional antagonism of the S1P1 receptor on T-cells (whereby the ability of SIP to mobilize T-cell egress from lymph nodes is reduced) and persistent agonism of the S1P1 receptor on lymph node endothelium (such that barrier function opposing transmigration of lymphocytes is increased) (Matloubian et al., *Nature*, 427:355-360, 2004; Baumruker et al., *Expert Opin. Investig. Drugs*, 16:283-289, 2007). It has been reported that agonism of the S1P1 receptor alone is sufficient to achieve lymphocyte sequestration (Sanna et al., *J Biol Chem.*, 279:13839-13848, 2004) and that this occurs without impairment of immune responses to systemic infection (Brinkmann et al., *Transplantation*, 72:764-769, 2001; Brinkmann et al., *Transplant Proc.*, 33:530-531, 2001).

That agonism of endothelial S1P1 receptors has a broader role in promoting vascular integrity is supported by work implicating the S1P1 receptor in capillary integrity in mouse skin and lung (Sanna et al., *Nat Chem Biol.*, 2:434-441, 2006). Vascular integrity can be compromised by inflammatory processes, for example as may derive from sepsis, major trauma and surgery so as to lead to acute lung injury or respiratory distress syndrome (Johan Groeneveld, *Vascul. Pharmacol.*, 39:247-256, 2003).

An exemplary SIP receptor agonist having agonist activity on the S1P1 receptor is FTY720 (fingolimod), an immunosuppressive agent currently in clinical trials (Martini et al., *Expert Opin. Investig. Drugs*, 16:505-518, 2007). FTY720 acts as a prodrug which is phosphorylated in vivo; the phosphorylated derivative is an agonist for S1P1, S1P3, S1P4 and S1P5 receptors (but not the S1P2 receptor) (Chiba, *Pharmacology & Therapeutics*, 108:308-319, 2005). FTY720 has been shown to rapidly and reversibly induce lymphopenia (also referred to as peripheral lymphocyte lowering (PLL); Hale et al., *Bioorg. Med. Chem. Lett.*, 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., *Immunol. Rev.*, 195:160-177, 2003; Schwab et al., *Nature Immunol.*, 8:1295-1301, 2007).

In clinical trials, FTY720 elicited an adverse event (i.e., transient asymptomatic bradycardia) due to its agonism of the S1P3 receptor (Budde et al., *J. Am. Soc. Nephrol.*, 13:1073-1083, 2002; Sanna et al., *J. Biol. Chem.*, 279: 13839-13848, 2004; Ogawa et al., *BBRC*, 361:621-628, 2007).

FTY720 has been reported to have therapeutic efficacy in at least: a rat model for autoimmune myocarditis and a mouse model for acute viral myocarditis (Kiyabayashi et al., *J. Cardiovasc. Pharmacol.*, 35:410-416, 2000; Miyamoto et al., *J. Am. Coll. Cardiol.*, 37:1713-1718, 2001); mouse models for inflammatory bowel disease including colitis (Mizushima et al., *Inflamm. Bowel Dis.*, 10:182-192, 2004; Deguchi et al., *Oncology Reports*, 16:699-703, 2006; Fujii et al., *Am. J. Physiol. Gastrointest. Liver Physiol.*, 291:G267-G274, 2006; Daniel et al., *J. Immunol.*, 178:2458-2468, 2007); a rat model for progressive mesangioproliferative glomerulonephritis (Martini et al., *Am. J. Physiol. Renal Physiol.*, 292:F1761-F1770, 2007); a mouse model for asthma, suggested to be primarily through the S1P1 receptor on the basis of work using the the S1P1 receptor agonist SEW2871 (Idzko et al, *J. Clin. Invest.*, 116:2935-2944, 2006); a mouse model for airway inflammation and induction of bronchial hyperresponsiveness (Sawicka et al., *J. Immunol.*, 171; 6206-6214, 2003); a mouse model for atopic dermatitis (Kohno et al., *Biol. Pharm. Bull.*, 27:1392-1396, 2004); a mouse model for ischemia-reperfusion injury (Kaudel et al., *Transplant. Proc*, 39:499-502, 2007); a mouse model for systemic lupus erythematosus (SLE) (Okazaki et al., *J. Rheumatol.*, 29:707-716, 2002; Herzinger et al, *Am. J. Clin. Dermatol.*, 8:329-336, 2007); rat models for rheumatoid arthritis (Matsuura et al., *Int. J. Immunopharmacol.*, 22:323-331, 2000; Matsuura et al., *Inflamm. Res.*, 49:404-410, 2000); a rat model for autoimmune uveitis (Kurose et al., *Exp. Eye Res.*, 70:7-15, 2000); mouse models for type I diabetes (Fu et al, *Transplantation*, 73:1425-1430, 2002; Maki et al., *Transplantation*, 74:1684-1686, 2002; Yang et al., *Clinical Immunology*, 107:30-35, 2003; Maki et al., *Transplantation*, 79:1051-1055, 2005); mouse models for atherosclerosis (Nofer et al., *Circulation*, 115:501-508, 2007; Keul et al., *Arterioscler. Thromb. Vasc. Biol.*, 27:607-

613, 2007); a rat model for brain inflammatory reaction following traumatic brain injury (TBI) (Zhang et al., *J. Cell. Mol. Med.*, 11:307-314, 2007); and mouse models for graft coronary artery disease and graft-versus-host disease (GVHD) (Hwang et al., *Circulation*, 100:1322-1329, 1999; Taylor et al., *Blood*, 110:3480-3488, 2007). In vitro results suggest that FTY720 may have therapeutic efficacy for β-amyloid-related inflammatory diseases including Alzheimer's disease (Kaneider et al., *FASEB J.*, 18:309-311, 2004). KRP-203, an SIP receptor agonist having agonist activity on the S1P1 receptor, has been reported to have therapeutic efficacy in a rat model for autoimmune myocarditis (Ogawa et al., *BBRC*, 361:621-628, 2007). Using the S1P1 receptor agonist SEW2871, it has been shown that agonism of endothelial S1P1 receptors prevents proinflammatory monocyte/endothelial interactions in type I diabetic vascular endothelium (Whetzel et al., *Circ. Res.*, 99:731-739, 2006) and protects the vasculature against TNFα-mediated monocyte/endothelial interactions (Bolick et al., *Arterioscler. Thromb. Vasc. Biol.*, 25:976-981, 2005).

Additionally, FTY720 has been reported to have therapeutic efficacy in experimental autoimmune encephalomyelitis (EAE) in rats and mice, a model for human multiple sclerosis (Brinkmann et al., *J. Biol. Chem.*, 277:21453-21457, 2002; Fujino et al., *J. Pharmacol. Exp. Ther.*, 305: 70-77, 2003; Webb et al., *J. Neuroimmunol.*, 153:108-121, 2004; Rausch et al., *J. Magn. Reson. Imaging*, 20:16-24, 2004; Kataoka et al., *Cellular & Molecular Immunology*, 2:439-448, 2005; Brinkmann et al., *Pharmacology & Therapeutics*, 115:84-105, 2007; Baumruker et al., *Expert Opin. Investig. Drugs*, 16:283-289, 2007; Balatoni et al., *Brain Research Bulletin*, 74:307-316, 2007). Furthermore, FTY720 has been found to have therapeutic efficacy for multiple sclerosis in clinical trials. In Phase II clinical trials for relapsing-remitting multiple sclerosis, FTY720 was found to reduce the number of lesions detected by magnetic resonance imaging (MRI) and clinical disease activity in patients with multiple sclerosis (Kappos et al., *N. Engl. J. Med.*, 355:1124-1140, 2006; Martini et al., *Expert Opin. Investig. Drugs*, 16:505-518, 2007; Zhang et al., *Mini-Reviews in Medicinal Chemistry*, 7:845-850, 2007; Brinkmann, *Pharmacology & Therapeutics*, 115:84-105, 2007). FTY720 is currently in Phase III studies of remitting-relapsing multiple sclerosis (Brinkmann, Pharmacology & Therapeutics, 115:84-105, 2007; Baumruker et al., *Expert. Opin.* Investig. Drugs, 16:283-289, 2007; Dev et al., *Pharmacology and Therapeutics*, 117:77-93, 2008).

Recently, FTY720 has been reported to have anti-viral activity. Specific data has been presented in the lymphocytic choriomeningitis virus (LCMV) mouse model, wherein the mice were infected with either the Armstrong or the clone 13 strain of LCMV (Premenko-Lanier et al., Nature, 454, 894, 2008).

FTY720 has been reported to impair migration of dendritic cells infected with *Francisella tularensis* to the mediastinal lymph node, thereby reducing the bacterial colonization of it. *Francisella tularensis* is associated with tularemia, ulceroglandular infection, respiratory infection and a typhoidal disease (E. Bar-Haim et al, *PLoS Pathogens,* 4(11): e1000211. doi:10.1371/journal.ppat.1000211, 2008).

It has also been recently reported that a short-term high dose of FTY720 rapidly reduced ocular infiltrates in experimental autoimmune uveoretinitis. When given in the early stages of ocular inflammation, FTY720 rapidly prevented retinal damage. It was reported to not only prevent infiltration of target organs, but also reduce existing infiltration (Raveney et al., Arch. Ophthalmol. 126(10), 1390, 2008).

It has been reported that treatment with FTY720 relieved ovariectomy-induced osteoporosis in mice by reducing the number of mature osteoclasts attached to the bone surface. The data provided evidence that SIP controlled the migratory behaviour of osteoclast precursors, dynamically regulating bone mineral homeostasis (Ishii et al., Nature, advance online publication, 8 *Feb.* 2009, doi:10.1038/nature07713).

Agonism of the S1P1 receptor has been implicated in enhancement of survival of oligodendrocyte progenitor cells. Survival of oligodendrocyte progenitor cells is a required component of the remyelination process. Remyelination of multiple sclerosis lesions is considered to promote recovery from clinical relapses. (Miron et al., *Ann. Neurol.,* 63:61-71, 2008; Coelho et al., *J. Pharmacol. Exp. Ther.,* 323:626-635, 2007; Dev et al., *Pharmacology and Therapeutics,* 117:77-93, 2008). It also has been shown that the S1P1 receptor plays a role in platelet-derived growth factor (PDGF)-induced oligodendrocyte progenitor cell mitogenesis (Jung et al., Glia, 55:1656-1667, 2007).

Agonism of the S1P1 receptor has also been reported to mediate migration of neural stem cells toward injured areas of the central nervous system (CNS), including in a rat model of spinal cord injury (Kimura et al., *Stem Cells,* 25:115-124, 2007).

Agonism of the S1P1 receptor has been implicated in the inhibition of keratinocyte proliferation (Sauer et al., *J. Biol. Chem.,* 279:38471-38479, 2004), consistent with reports that SIP inhibits keratinocyte proliferation (Kim et al., *Cell Signal,* 16:89-95, 2004). The hyperproliferation of keratinocytes at the entrance to the hair follicle, which can then become blocked, and an associated inflammation are significant pathogenetic factors of acne (Koreck et al., *Dermatology,* 206:96-105, 2003; Webster, *Cutis,* 76:4-7, 2005).

FTY720 has been reported to have therapeutic efficacy in inhibiting pathologic angiogenesis, such as that as may occur in tumor development. Inhibition of angiogenesis by FTY720 is thought to involve agonism of the S1P1 receptor (Oo et al., *J. Biol. Chem.,* 282; 9082-9089, 2007; Schmid et al., *J. Cell Biochem.,* 101:259-270, 2007). FTY720 has been reported to have therapeutic efficacy for inhibiting primary and metastatic tumor growth in a mouse model of melanoma (LaMontagne et al., *Cancer Res.,* 66:221-231, 2006). FTY720 has been reported to have therapeutic efficacy in a mouse model for metastatic hepatocellular carcinoma (Lee et al., *Clin. Cancer Res.,* 11:84588466, 2005).

It has been reported that oral administration of FTY720 to mice potently blocked VEGF-induced vascular permeability, an important process associated with angiogenesis, inflammation, and pathological conditions such as sepsis, hypoxia, and solid tumor growth (T Sanchez et al, *J. Biol. Chem.,* 278(47), 47281-47290, 2003).

Cyclosporin A and FK506 (calcineurin inhibitors) are drugs used to prevent rejection of transplanted organs. Although they are effective in delaying or suppressing transplant rejection, classical immunosuppressants such as cyclosporin A and FK506 are known to cause several undesirable side effects including nephrotoxicity, neurotoxicity, f-cell toxicity and gastrointestinal discomfort. There is an unmet need in organ transplantation for an immunosuppressant without these side effects which is effective as a monotherapy or in combination with a classical immunosuppressant for inhibiting migration of, e.g., alloantigen-reactive T-cells to the grafted tissue, thereby prolonging graft survival.

FTY720 has been shown to have therapeutic efficacy in transplant rejection both as a monotherapy and in synergistic combination with a classical immunosuppressant, including cyclosporin A, FK506 and RAD (an mTOR inhibitor). It has been shown that, unlike the classical immunosuppressants cyclosporin A, FK506 and RAD, FTY720 has efficacy for prolonging graft survival without inducing general immunosuppression, and this difference in drug action is believed to be relevant to the synergism observed for the combination (Brinkmann et al., *Transplant Proc.*, 33:530-531, 2001; Brinkmann et al., *Transplantation*, 72:764-769, 2001).

Agonism of the S1P1 receptor has been reported to have therapeutic efficacy for prolonging allograft survival in mouse and rat skin allograft models (Lima et al., *Transplant Proc.*, 36:1015-1017, 2004; Yan et al., *Bioorg. & Med. Chem. Lett.*, 16:3679-3683, 2006). FTY720 has been reported to have therapeutic efficacy for prolonging allograft survival in a rat cardiac allograft model (Suzuki et al., *Transpl. Immunol.*, 4:252-255, 1996). FTY720 has been reported to act synergistically with cyclosporin A to prolong rat skin allograft survival (Yanagawa et al., *J. Immunol.*, 160:5493-5499, 1998), to act synergistically with cyclosporin A and with FK506 to prolong rat cardiac allograft survival, and to act synergistically with cyclosporin A to prolong canine renal allograft survival and monkey renal allograft survival (Chiba et al., *Cell Mol. Biol.*, 3:11-19, 2006). KRP-203, an SIP receptor agonist has been reported to have therapeutic efficacy for prolonging allograft survival in a rat skin allograft model and both as monotherapy and in synergistic combination with cyclosporin A in a rat cardiac allograft model (Shimizu et al., *Circulation*, 111:222-229, 2005). KRP-203 also has been reported to have therapeutic efficacy in combination with mycophenolate mofetil (MMF; a prodrug for which the active metabolite is mycophenolic acid, an inhibitor of purine biosynthesis) for prolonging allograft survival both in a rat renal allograft model and in a rat cardiac allograft model (Suzuki et al., *J. Heart Lung Transplant*, 25:302-209, 2006; Fujishiro et al., *J. Heart Lung Transplant*, 25:825-833, 2006). It has been reported that an agonist of the S1P1 receptor, AUY954, in combination with a subtherapeutic dose of RAD001 (Certican/Everolimus, an mTOR inhibitor) can prolong rat cardiac allograft survival (Pan et al., *Chemistry & Biology*, 13:1227-1234, 2006). In a rat small bowel allograft model, FTY720 has been reported to act synergistically with cyclosporin A to prolong small bowel allograft survival (Sakagawa et al., *Transpl. Immunol.*, 13:161-168, 2004). FTY720 has been reported to have therapeutic efficacy in a mouse islet graft model (Fu et al., *Transplantation*, 73:1425-1430, 2002; Liu et al., *Microsurgery*, 27:300-304; 2007) and in a study using human islet cells to evidence no detrimental effects on human islet function (Truong et al., *American Journal of Transplantation*, 7:2031-2038, 2007).

FTY720 has been reported to reduce the nociceptive behavior in the spared nerve injury model for neuropathic pain which does not depend on prostaglandin synthesis (O. Costu et al, *Journal of Cellular and Molecular Medicine* 12(3), 995-1004, 2008).

FTY720 has been reported to impair initiation of murine contact hypersensitivity (CHS). Adoptive transfer of immunized lymph node cells from mice treated with FTY720 during the sensitization phase was virtually incapable of inducing CHS response in recipients (D. Nakashima et al., *J. Investigative Dermatology* (128(12), 2833-2841, 2008).

It has been reported that prophylactic oral administration of FTY720 (1 mg/kg, three times a week), completely prevented the development of experimental autoimmune myasthenia gravis (EAMG) in C57BL/6 mice (T. Kohono et al, *Biological & Pharmaceutical Bulletin*, 28(4), 736-739, 2005).

S1P1 receptor agonists are useful to treat or prevent conditions where suppression of the immune system or agonism of the S1P1 receptor is in order, such as diseases and disorders mediated by lymphocytes, transplant rejection, autoimmune diseases and disorders, inflammatory diseases and disorders, and conditions that have an underlying defect in vascular integrity or that relate to angiogenesis such as may be pathologic.

In one embodiment, the present invention encompasses compounds which are agonists of the S1P1 receptor having good overall physical properties and biological activities and having an effectiveness that is substantially at least that of prior compounds with activity at the S1P1 receptor.

Citation of any reference throughout this application is not to be construed as an admission that such reference is prior art to the present application.

SUMMARY OF THE INVENTION

The present invention encompasses compounds of Formula (Ia) and pharmaceutically acceptable salts, solvates, and hydrates thereof:

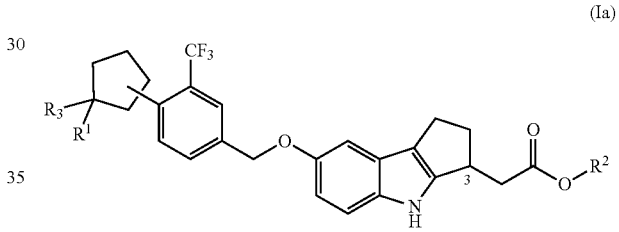

(Ia)

wherein:
$R^1$ is H or OH;
$R^3$ is H; or
$R^1$ and $R^3$ together form an oxo group;
and
$R^2$ is H or the group of Formula (IIa):

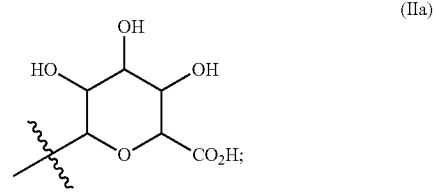

(IIa)

provided that if $R^2$ is H, then $R^1$ and $R^3$ are not both H.

The present invention encompasses compounds which are S1P1 receptor agonists having at least immunosuppressive, anti-inflammatory and/or hemostatic activities, e.g. by modulating leukocyte trafficking, sequestering lymphocytes in secondary lymphoid tissues, and/or enhancing vascular integrity.

S1P1 receptor agonists are useful to treat or prevent conditions where suppression of the immune system or agonism of the S1P1 receptor is in order, such as diseases and disorders mediated by lymphocytes, transplant rejection, autoimmune diseases and disorders, inflammatory diseases and disorders (e.g., acute and chronic inflammatory conditions), cancer, and conditions that have an underlying defect in vascular integrity or that are associated with angiogenesis such as may be pathologic (e.g., as may occur in inflammation, tumor development and atherosclerosis). Such conditions where suppression of the immune system or agonism of the S1P1 receptor is in order include diseases and disorders mediated by lymphocytes, conditions that have an underlying defect in vascular integrity, autoimmune diseases and disorders, inflammatory diseases and disorders (e.g., acute and chronic inflammatory conditions), acute or chronic rejection of cells, tissue or solid organ grafts, arthritis including psoriatic arthritis and rheumatoid arthritis, diabetes including type I diabetes, demyelinating disease including multiple sclerosis, ischemia-reperfusion injury including renal and cardiac ischemia-reperfusion injury, inflammatory skin disease including psoriasis, atopic dermatitis and acne, hyperproliferative skin disease including acne, inflammatory bowel disease including Crohn's disease and ulcerative colitis, systemic lupus erythematosus, asthma, uveitis, myocarditis, allergy, atherosclerosis, brain inflammation including Alzheimer's disease and brain inflammatory reaction following traumatic brain injury, central nervous system disease including spinal cord injury or cerebral infarction, pathologic angiogenesis including as may occur in primary and metastatic tumor growth, rheumatoid arthritis, diabetic retinopathy and atherosclerosis, cancer, chronic pulmonary disease, acute lung injury, acute respiratory disease syndrome, sepsis and the like.

One aspect of the present invention pertains to pharmaceutical compositions comprising a compound of the present invention and a pharmaceutically acceptable carrier. In some embodiments, the pharmaceutical compositions are suitable for oral administration. In some embodiments, the pharmaceutical compositions are suitable for parental administration.

One aspect of the present invention pertains to pharmaceutical compositions comprising a compound of the present invention, a salt, a hydrate or solvate or a crystalline form and a pharmaceutically acceptable carrier. In some embodiments, the pharmaceutical compositions are suitable for oral administration. In some embodiments, the pharmaceutical compositions are suitable for parental administration.

One aspect of the present invention pertains to methods for treating a disorder associated with the S1P1 receptor in an individual comprising administering to the individual in need thereof a therapeutically effective amount of a compound of the present invention or a pharmaceutical composition thereof.

One aspect of the present invention pertains to methods for treating an S1P1 receptor-associated disorder in an individual comprising administering to the individual in need thereof a therapeutically effective amount of a compound of the present invention or a pharmaceutical composition thereof.

One aspect of the present invention pertains to methods for treating an S1P1 receptor-associated disorder associated with the S1P1 receptor in an individual comprising administering to the individual in need thereof a therapeutically effective amount of a compound of the present invention, a salt, a hydrate or solvate, a crystalline form, or a pharmaceutical composition thereof.

One aspect of the present invention pertains to methods for treating a disorder associated with the S1P1 receptor in an individual comprising administering to the individual in need thereof a therapeutically effective amount of a compound of the present invention or a pharmaceutical composition thereof, wherein said disorder associated with the S1P1 receptor is selected from: a disease or disorder mediated by lymphocytes, an autoimmune disease or disorder, an inflammatory disease or disorder, an inflammatory skin disease, cancer, psoriasis, atopic dermatitis, rheumatoid arthritis, Crohn's disease, transplant rejection, multiple sclerosis, systemic lupus erythematosus, ulcerative colitis, type I diabetes, and acne.

One aspect of the present invention pertains to methods for treating a disorder associated with the S1P1 receptor in an individual comprising administering to the individual in need thereof a therapeutically effective amount of a compound of the present invention or a pharmaceutical composition thereof, wherein said disorder associated with the S1P1 receptor is selected from the group consisting of: a disease or disorder mediated by lymphocytes, an autoimmune disease or disorder, an inflammatory disease or disorder, cancer, psoriasis, rheumatoid arthritis, Crohn's disease, transplant rejection, multiple sclerosis, systemic lupus erythematosus, ulcerative colitis, type I diabetes and acne.

One aspect of the present invention pertains to methods for treating a disorder associated with the S1P1 receptor in an individual comprising administering to the individual in need thereof a therapeutically effective amount of a compound of the present invention, a salt, a hydrate or solvate, a crystalline form, or a pharmaceutical composition thereof, wherein said disorder associated with the S1P1 receptor is selected from the group consisting of: a disease or disorder mediated by lymphocytes, an autoimmune disease or disorder, an inflammatory disease or disorder, cancer, psoriasis, rheumatoid arthritis, Crohn's disease, transplant rejection, multiple sclerosis, systemic lupus erythematosus, ulcerative colitis, type I diabetes and acne.

One aspect of the present invention pertains to methods for treating a disease or disorder mediated by lymphocytes in an individual comprising administering to the individual in need thereof a therapeutically effective amount of a compound of the present invention or a pharmaceutical composition thereof.

One aspect of the present invention pertains to methods for treating an autoimmune disease or disorder in an individual comprising administering to the individual in need thereof a therapeutically effective amount of a compound of the present invention or a pharmaceutical composition thereof.

One aspect of the present invention pertains to methods for treating an inflammatory disease or disorder in an individual comprising administering to the individual in need thereof a therapeutically effective amount of a compound of the present invention or a pharmaceutical composition thereof.

One aspect of the present invention pertains to methods for treating cancer in an individual comprising administering to the individual in need thereof a therapeutically effective amount of a compound of the present invention or a pharmaceutical composition thereof.

One aspect of the present invention pertains to methods for treating a disorder in an individual comprising administering to the individual in need thereof a therapeutically effective amount of a compound of the present invention or a pharmaceutical composition thereof, wherein said disorder is selected from the group consisting of psoriasis, rheumatoid arthritis, Crohn's disease, transplant rejection, multiple sclerosis, systemic lupus erythematosus, ulcerative colitis, type I diabetes and acne.

One aspect of the present invention pertains to methods for treating psoriasis in an individual comprising administering to the individual in need thereof a therapeutically effective amount of a compound of the present invention or a pharmaceutical composition thereof.

One aspect of the present invention pertains to methods for treating atopic dermatitis in an individual comprising administering to the individual in need thereof a therapeutically effective amount of a compound of the present invention or a pharmaceutical composition thereof.

One aspect of the present invention pertains to methods for treating rheumatoid arthritis in an individual comprising administering to the individual in need thereof a therapeutically effective amount of a compound of the present invention or a pharmaceutical composition thereof.

One aspect of the present invention pertains to methods for treating Crohn's disease in an individual comprising administering to the individual in need thereof a therapeutically effective amount of a compound of the present invention or a pharmaceutical composition thereof.

One aspect of the present invention pertains to methods for treating transplant rejection in an individual comprising administering to the individual in need thereof a therapeutically effective amount of a compound of the present invention or a pharmaceutical composition thereof.

One aspect of the present invention pertains to methods for treating multiple sclerosis in an individual comprising administering to the individual in need thereof a therapeutically effective amount of a compound of the present invention or a pharmaceutical composition thereof.

One aspect of the present invention pertains to methods for treating systemic lupus erythematosus in an individual comprising administering to the individual in need thereof a therapeutically effective amount of a compound of the present invention or a pharmaceutical composition thereof.

One aspect of the present invention pertains to methods for treating ulcerative colitis in an individual comprising administering to the individual in need thereof a therapeutically effective amount of a compound of the present invention or a pharmaceutical composition thereof.

One aspect of the present invention pertains to methods for treating type I diabetes in an individual comprising administering to the individual in need thereof a therapeutically effective amount of a compound of the present invention or a pharmaceutical composition thereof.

One aspect of the present invention pertains to methods for treating acne in an individual comprising administering to the individual in need thereof a therapeutically effective amount of a compound of the present invention or a pharmaceutical composition thereof.

One aspect of the present invention pertains to methods for treating a disorder associated with the S1P1 receptor in an individual comprising administering to the individual in need thereof a therapeutically effective amount of a compound of the present invention or a pharmaceutical composition thereof, wherein said disorder associated with the S1P1 receptor is a microbial infection or disease or a viral infection or disease.

One aspect of the present invention pertains to methods for treating a disorder associated with the S1P1 receptor in an individual comprising administering to the individual in need thereof a therapeutically effective amount of a compound of the present invention, a salt, a hydrate or solvate, a crystalline form, or a pharmaceutical composition thereof, wherein said disorder associated with the S1P1 receptor is a microbial infection or disease or a viral infection or disease.

One aspect of the present invention pertains to methods for treating gastritis in an individual comprising administering to the individual in need thereof a therapeutically effective amount of a compound of the present invention or a pharmaceutical composition thereof.

One aspect of the present invention pertains to methods for treating polymyositis in an individual comprising administering to the individual in need thereof a therapeutically effective amount of a compound of the present invention or a pharmaceutical composition thereof.

One aspect of the present invention pertains to methods for treating thyroiditis in an individual comprising administering to the individual in need thereof a therapeutically effective amount of a compound of the present invention or a pharmaceutical composition thereof.

One aspect of the present invention pertains to methods for treating vitiligo in an individual comprising administering to the individual in need thereof a therapeutically effective amount of a compound of the present invention or a pharmaceutical composition thereof.

One aspect of the present invention pertains to methods for treating hepatitis in an individual comprising administering to the individual in need thereof a therapeutically effective amount of a compound of the present invention or a pharmaceutical composition thereof.

One aspect of the present invention pertains to methods for treating biliary cirrhosis in an individual comprising administering to the individual in need thereof a therapeutically effective amount of a compound of the present invention or a pharmaceutical composition thereof.

One aspect of the present invention pertains to the use of compounds of the present invention in the manufacture of a medicament for the treatment of an S1P1 receptor-associated disorder.

One aspect of the present invention pertains to the use of compounds of the present invention, a salt, a hydrate or solvate, a crystalline form, or a pharmaceutical composition in the manufacture of a medicament for the treatment of an S1P1 receptor-associated disorder.

One aspect of the present invention pertains to the use of compounds of the present invention in the manufacture of a medicament for the treatment of a S1P1 receptor-associated disorder selected from the group consisting of: a disease or disorder mediated by lymphocytes, an autoimmune disease or disorder, an inflammatory disease or disorder, an inflammatory skin disease, cancer, psoriasis, atopic dermatitis, rheumatoid arthritis, Crohn's disease, transplant rejection, multiple sclerosis, systemic lupus erythematosus, ulcerative colitis, type I diabetes, and acne.

One aspect of the present invention pertains to the use of compounds of the present invention in the manufacture of a medicament for the treatment of a S1P1 receptor-associated disorder selected from the group consisting of: a disease or disorder mediated by lymphocytes, an autoimmune disease or disorder, an inflammatory disease or disorder, cancer, psoriasis, rheumatoid arthritis, Crohn's disease, transplant rejection, multiple sclerosis, systemic lupus erythematosus, ulcerative colitis, type I diabetes and acne.

One aspect of the present invention pertains to the use of compounds of the present invention, a salt, a hydrate or solvate, a crystalline form, or a pharmaceutical composition in the manufacture of a medicament for the treatment of a S1P1 receptor-associated disorder selected from the group consisting of: a disease or disorder mediated by lymphocytes, an autoimmune disease or disorder, an inflammatory disease or disorder, cancer, psoriasis, rheumatoid arthritis, Crohn's disease, transplant rejection, multiple sclerosis, systemic lupus erythematosus, ulcerative colitis, type I diabetes and acne.

One aspect of the present invention pertains to the use of compounds of the present invention in the manufacture of a medicament for the treatment of a disease or disorder mediated by lymphocytes.

One aspect of the present invention pertains to the use of compounds of the present invention in the manufacture of a medicament for the treatment of an autoimmune disease or disorder.

One aspect of the present invention pertains to the use of compounds of the present invention in the manufacture of a medicament for the treatment of an inflammatory disease or disorder.

One aspect of the present invention pertains to the use of compounds of the present invention in the manufacture of a medicament for the treatment of cancer.

One aspect of the present invention pertains to the use of compounds of the present invention in the manufacture of a medicament for the treatment of an S1P1 receptor-associated disorder selected from the group consisting of psoriasis, rheumatoid arthritis, Crohn's disease, transplant rejection, multiple sclerosis, systemic lupus erythematosus, ulcerative colitis, type I diabetes and acne.

One aspect of the present invention pertains to the use of compounds of the present invention in the manufacture of a medicament for the treatment of psoriasis.

One aspect of the present invention pertains to the use of compounds of the present invention in the manufacture of a medicament for the treatment of atopic dermatitis.

One aspect of the present invention pertains to the use of compounds of the present invention in the manufacture of a medicament for the treatment of rheumatoid arthritis.

One aspect of the present invention pertains to the use of compounds of the present invention in the manufacture of a medicament for the treatment of Crohn's disease.

One aspect of the present invention pertains to the use of compounds of the present invention in the manufacture of a medicament for the treatment of transplant rejection.

One aspect of the present invention pertains to the use of compounds of the present invention in the manufacture of a medicament for the treatment of multiple sclerosis.

One aspect of the present invention pertains to the use of compounds of the present invention in the manufacture of a medicament for the treatment of systemic lupus erythematosus.

One aspect of the present invention pertains to the use of compounds of the present invention in the manufacture of a medicament for the treatment of ulcerative colitis.

One aspect of the present invention pertains to the use of compounds of the present invention in the manufacture of a medicament for the treatment of type I diabetes.

One aspect of the present invention pertains to the use of compounds of the present invention in the manufacture of a medicament for the treatment of acne.

One aspect of the present invention pertains to the use of compounds of the present invention in the manufacture of a medicament for the treatment of a S1P1 receptor-associated disorder wherein the S1P1 receptor-associated disorder is a microbial infection or disease or a viral infection or disease.

One aspect of the present invention pertains to the use of compounds of the present invention, a salt, a hydrate or solvate, a crystalline form, or a pharmaceutical composition in the manufacture of a medicament for the treatment of a S1P1 receptor-associated disorder wherein the S1P1 receptor-associated disorder is a microbial infection or disease or a viral infection or disease.

One aspect of the present invention pertains to the use of compounds of the present invention in the manufacture of a medicament for the treatment of gastritis.

One aspect of the present invention pertains to the use of compounds of the present invention in the manufacture of a medicament for the treatment of polymyositis.

One aspect of the present invention pertains to the use of compounds of the present invention in the manufacture of a medicament for the treatment of thyroiditis.

One aspect of the present invention pertains to the use of compounds of the present invention in the manufacture of a medicament for the treatment of vitiligo.

One aspect of the present invention pertains to the use of compounds of the present invention in the manufacture of a medicament for the treatment of hepatitis.

One aspect of the present invention pertains to the use of compounds of the present invention in the manufacture of a medicament for the treatment of biliary cirrhosis.

One aspect of the present invention pertains to compounds of the present invention for use in a method for the treatment of the human or animal body by therapy.

One aspect of the present invention pertains to compounds of the present invention, a salt, a hydrate or solvate, a crystalline form, for use in a method for the treatment of the human or animal body by therapy.

One aspect of the present invention pertains to compounds of the present invention for use in a method for the treatment of an S1P1 receptor-associated disorder.

One aspect of the present invention pertains to compounds of the present invention, a salt, a hydrate or solvate, a crystalline form, for use in a method for the treatment of an S1P1 receptor-associated disorder.

One aspect of the present invention pertains to compounds of the present invention for use in a method for the treatment of a S1P1 receptor-associated disorder selected from the group consisting of: a disease or disorder mediated by lymphocytes, an autoimmune disease or disorder, an inflammatory disease or disorder, an inflammatory skin disease, cancer, psoriasis, atopic dermatitis, rheumatoid arthritis, Crohn's disease, transplant rejection, multiple sclerosis, systemic lupus erythematosus, ulcerative colitis, type I diabetes, and acne.

One aspect of the present invention pertains to compounds of the present invention for use in a method for the treatment of a S1P1 receptor-associated disorder selected from the group consisting of: a disease or disorder mediated by lymphocytes, an autoimmune disease or disorder, an inflammatory disease or disorder, cancer, psoriasis, rheumatoid arthritis, Crohn's disease, transplant rejection, multiple sclerosis, systemic lupus erythematosus, ulcerative colitis, type I diabetes and acne.

One aspect of the present invention pertains to compounds of the present invention, a salt, a hydrate or solvate, a crystalline form, for use in a method for the treatment of a S1P1 receptor-associated disorder selected from the group consisting of: a disease or disorder mediated by lymphocytes, an autoimmune disease or disorder, an inflammatory disease or disorder, cancer, psoriasis, rheumatoid arthritis, Crohn's disease, transplant rejection, multiple sclerosis, systemic lupus erythematosus, ulcerative colitis, type I diabetes and acne.

One aspect of the present invention pertains to compounds of the present invention for use in a method for the treatment of a disease or disorder mediated by lymphocytes.

One aspect of the present invention pertains to compounds of the present invention for use in a method for the treatment of an autoimmune disease or disorder.

One aspect of the present invention pertains to compounds of the present invention for use in a method for the treatment of an inflammatory disease or disorder.

One aspect of the present invention pertains to compounds of the present invention for use in a method for the treatment of cancer.

One aspect of the present invention pertains to compounds of the present invention for use in a method for the treatment of an S1P1 receptor-associated disorder selected from the group consisting of psoriasis, rheumatoid arthritis, Crohn's disease, transplant rejection, multiple sclerosis, systemic lupus erythematosus, ulcerative colitis, type I diabetes and acne.

One aspect of the present invention pertains to compounds of the present invention for use in a method for the treatment of psoriasis.

One aspect of the present invention pertains to compounds of the present invention for use in a method for the treatment of atopic dermatitis.

One aspect of the present invention pertains to compounds of the present invention for use in a method for the treatment of rheumatoid arthritis.

One aspect of the present invention pertains to compounds of the present invention for use in a method for the treatment of Crohn's disease.

One aspect of the present invention pertains to compounds of the present invention for use in a method for the treatment of transplant rejection.

One aspect of the present invention pertains to compounds of the present invention for use in a method for the treatment of multiple sclerosis.

One aspect of the present invention pertains to compounds of the present invention for use in a method for the treatment of systemic lupus erythematosus.

One aspect of the present invention pertains to compounds of the present invention for use in a method for the treatment of ulcerative colitis.

One aspect of the present invention pertains to compounds of the present invention for use in a method for the treatment of type I diabetes.

One aspect of the present invention pertains to compounds of the present invention for use in a method for the treatment of acne.

One aspect of the present invention pertains to compounds of the present invention for use in a method for the treatment of a S1P1 receptor-associated disorder wherein the S1P1 receptor-associated disorder is a microbial infection or disease or a viral infection or disease.

One aspect of the present invention pertains to compounds of the present invention, a salt, a hydrate or solvate, a crystalline form, for use in a method for the treatment of a S1P1 receptor-associated disorder wherein the S1P1 receptor-associated disorder is a microbial infection or disease or a viral infection or disease.

One aspect of the present invention pertains to compounds of the present invention for use in a method for the treatment of gastritis.

One aspect of the present invention pertains to compounds of the present invention for use in a method for the treatment of polymyositis.

One aspect of the present invention pertains to compounds of the present invention for use in a method for the treatment of thyroiditis.

One aspect of the present invention pertains to compounds of the present invention for use in a method for the treatment of vitiligo.

One aspect of the present invention pertains to compounds of the present invention for use in a method for the treatment of hepatitis.

One aspect of the present invention pertains to compounds of the present invention for use in a method for the treatment of biliary cirrhosis.

One aspect of the present invention pertains to processes for preparing compositions comprising admixing a compound of the present invention and a pharmaceutically acceptable carrier. In some embodiments, the pharmaceutical compositions are suitable for oral administration. In some embodiments, the pharmaceutical compositions are suitable for parental administration.

One aspect of the present invention pertains to processes for preparing a composition comprising admixing a compound of the present invention, a salt, a hydrate or solvate, a crystalline form and a pharmaceutically acceptable carrier. In some embodiments, the pharmaceutical compositions are suitable for oral administration. In some embodiments, the pharmaceutical compositions are suitable for parental administration.

These and other aspects of the invention disclosed herein will be set forth in greater detail as the patent disclosure proceeds.

DETAILED DESCRIPTION OF THE INVENTION

Definitions

Figure 1A:
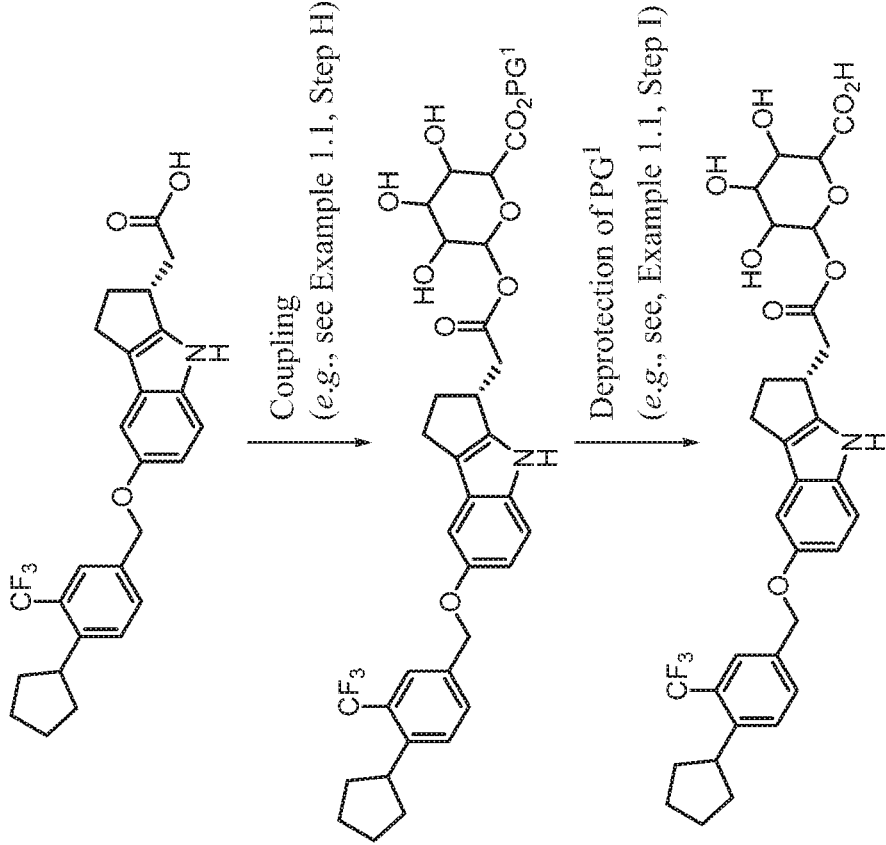
FIG. 1A shows a representative synthetic scheme for the preparation of compounds of the present invention, wherein $PG^1$ is a protecting group (e.g., an allyl group as described in Example 1.1, Step H). See WO2010/011316 and WO2011/094008 for the synthesis of (rac), (R), and (S) isomers of 2-(7-(4-cyclopentyl-3-(trifluoromethyl)benzyloxy)-1,2,3,4-tetrahydrocyclopenta[b]indol-3-yl)acetic acid. It is understood that although (R)-acid is explicitly shown FIG. 1A, the synthesis can be performed starting with (rac)-acid or (S)-acid.

For clarity and consistency, the following definitions will be used throughout this patent document.

The term "$C_1$-$C_6$ alkyl" refers to a straight or branched carbon radical containing 1 to 6 carbons. Some embodiments are 1 to 5 carbons, some embodiments are 1 to 4 carbons, some embodiments are 1 to 3 carbons and some embodiments are 1 or 2 carbons. Examples of an alkyl include, but are not limited to, methyl, ethyl, n-propyl, isopropyl, n-butyl, sec-butyl, isobutyl, tert-butyl, pentyl, isopentyl, tert-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like.

The term "hydrate" as used herein means a compound of the invention or a salt thereof, that further includes a stoichiometric or non-stoichiometric amount of water bound by non-covalent intermolecular forces.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" refers to any animal, including mammals, preferably mice, rats, other rodents, rabbits, dogs, cats, swine, cattle, sheep, horses, or primates and most preferably humans.

The term "inverse agonist" refers to a moiety that binds to the endogenous form of the receptor or to the constitutively activated form of the receptor and which inhibits the baseline intracellular response initiated by the active form of the receptor below the normal base level of activity which is observed in the absence of an agonist or partial agonist, or decreases GTP binding to a membrane. In some embodiments, the baseline intracellular response is inhibited in the presence of the inverse agonist by at least 30%. In some embodiments, the baseline intracellular response is inhibited in the presence of the inverse agonist by at least 50%. In some embodiments, the baseline intracellular response is inhibited in the presence of the inverse agonist by at least 75%, as compared with the baseline response in the absence of the inverse agonist.

The term "modulate or modulating" refers to an increase or decrease in the amount, quality, response or effect of a particular activity, function or molecule.

The term "oxo" refers to the diradical =O (i.e., the oxo group bonded to a carbon is a carbonyl group, as illustrated in Formula (Iu) and Formula (Iz)).

The term "pharmaceutical composition" refers to a composition comprising at least one active ingredient; including but not limited to, salts, solvates, and hydrates of compounds of the present invention, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "therapeutically effective amount" refers to the amount of active compound or pharmaceutical agent that elicits the biological or medicinal response in a tissue, system, animal, individual or human that is being sought by a researcher, veterinarian, medical doctor or other clinician, caregiver or by an individual, which includes one or more of the following:

(1) Preventing the disease, for example, preventing a disease, condition or disorder in an individual that may be predisposed to the disease, condition or disorder but does not yet experience or display the pathology or symptomatology of the disease;

(2) Inhibiting the disease, for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease, for example, ameliorating a disease, condition or disorder in an individual that is experiencing or displaying the pathology or symptomatology of the disease, condition or disorder (i.e., reversing the pathology and/or symptomatology).

Compounds of the Present Invention

One aspect of the present invention pertains to certain compounds of Formula (Ia) and pharmaceutically acceptable salts, solvates, and hydrates thereof:

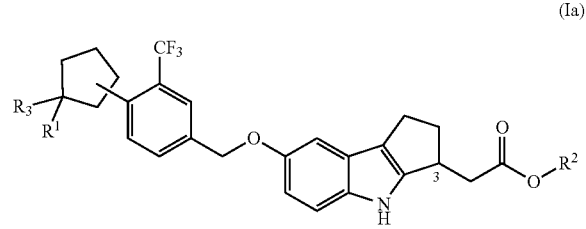

(Ia)

wherein:
$R^1$ is H or OH;
$R^3$ is H; or
$R^1$ and $R^3$ together form an oxo group;
and
$R^2$ is H or the group of Formula (IIa):

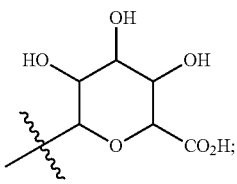

(IIa)

provided that if $R^2$ is H, then $R^1$ and $R^3$ are not both H.

One aspect of the present invention pertains to the following compound and pharmaceutically acceptable salts, solvates, and hydrates thereof:

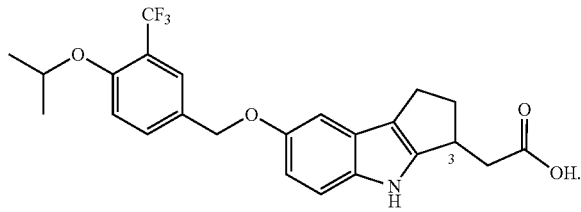 [SMILES: CC(C)Oc1ccc(COc2ccc3[nH]c4c(c3c2)CCC4CC(=O)O)cc1C(F)(F)F]

One aspect of the present invention pertains to compounds of Formula (Ic) and pharmaceutically acceptable salts, solvates and hydrates thereof:

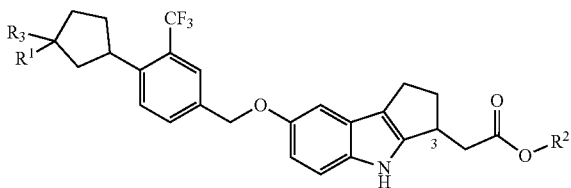

(Ic)

wherein: $R^1$, $R^2$, and $R^3$ have the same definitions as described herein, supra and infra.

One aspect of the present invention pertains to compounds of Formula (Ie) and pharmaceutically acceptable salts, solvates, and hydrates thereof:

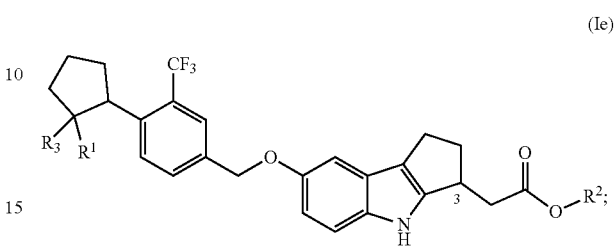

(Ie)

wherein: $R^1$, $R^2$, and $R^3$ have the same definitions as described herein, supra and infra.

In some embodiments, $R^1$ is OH; $R^3$ is H; or $R^1$ and $R^3$ together form an oxo group; and $R^2$ is H.

In some embodiments, $R^1$ is OH.

In some embodiments, $R^1$ is H.

In some embodiments, $R^2$ is H.

In some embodiments, $R^2$ is the group of Formula (IIa).

In some embodiments, $R^1$ and $R^3$ together form an oxo group.

In some embodiments, if $R^2$ is H, then $R^1$ and $R^3$ are not both H.

In some embodiments, $R^1$ and $R^3$ are both not H.

In some embodiments, if $R^1$ is H, then $R^2$ is the group of Formula (IIa).

In some embodiments, $R^1$ is OH; $R^3$ is H; and $R^2$ is H.

In some embodiments, $R^1$ and $R^3$ together form an oxo group; and $R^2$ is H.

In some embodiments, $R^1$ is H; $R^3$ is H; and $R^2$ is the group of Formula (IIa). Another aspect of the present invention pertains to compounds of Formula (Ig) and pharmaceutically acceptable salts, solvates, and hydrates thereof:

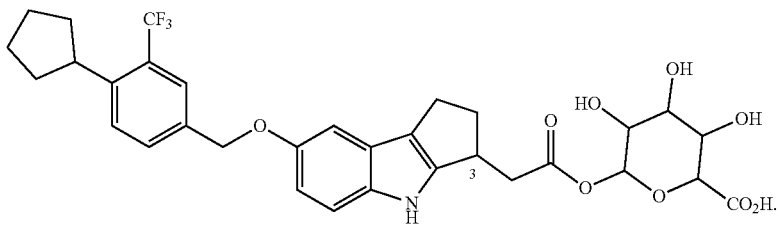

(Ig)

Some embodiments of the present invention pertain to compounds of Formula (Ii) and pharmaceutically acceptable salts, solvates, and hydrates thereof:

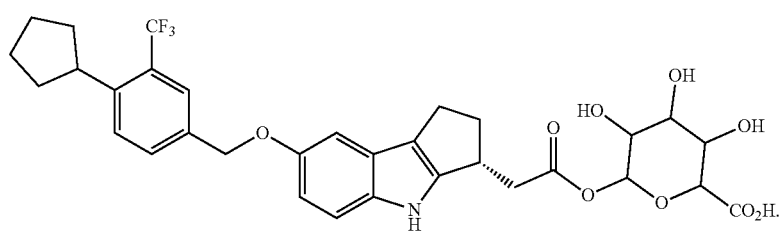

(Ii)

Some embodiments of the present invention pertain to compounds selected from the following compound and pharmaceutically acceptable salts solvates, and hydrates thereof:

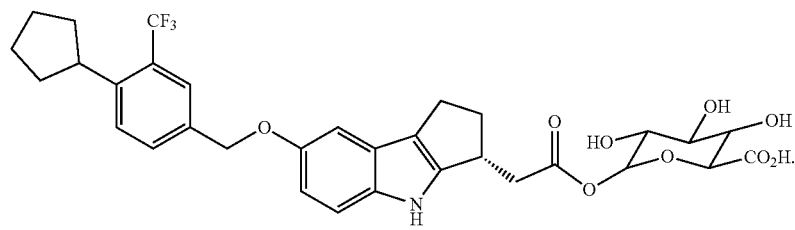

Some embodiments of the present invention pertain to compounds selected from (2S,3S,4S,5R)-6-(2-((R)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid (Compound 1) and pharmaceutically acceptable salts, solvates, and hydrates thereof.

Some embodiments of the present invention pertain to Compound 1.

In some embodiments, the present invention encompasses compounds of Formula (Ik) and pharmaceutically acceptable salts, solvates, and hydrates thereof:

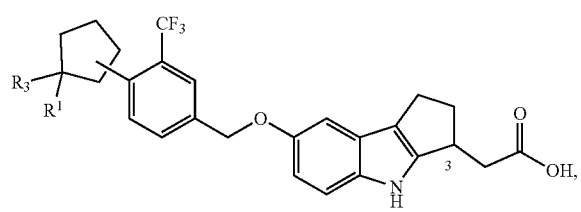
(Ik)

wherein:
$R^1$ is OH; and
$R^3$ is H;
or $R^1$ and $R^3$ together form an oxo group.

In some embodiments, the present invention encompasses compounds of Formula (Im) and pharmaceutically acceptable salts, solvates, and hydrates thereof:

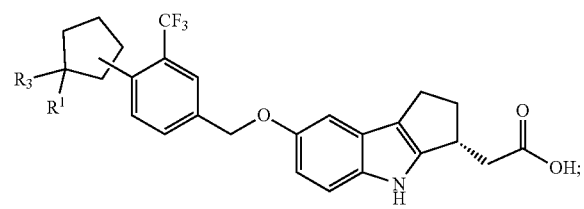
(Im)

wherein: $R^1$ and $R^3$ have the same definitions as described herein, supra and infra.

In some embodiments, the present invention encompasses compounds of Formula (Io) and pharmaceutically acceptable salts, solvates, and hydrates thereof:

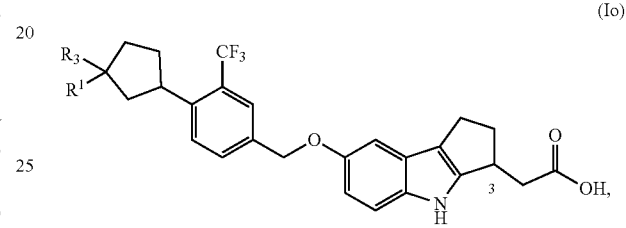
(Io)

wherein:
$R^1$ is H or OH; and
$R^3$ is H;
or $R^1$ and $R^3$ together is oxo.

In some embodiments, the present invention encompasses compounds of Formula (Iq) and pharmaceutically acceptable salts, solvates, and hydrates thereof:

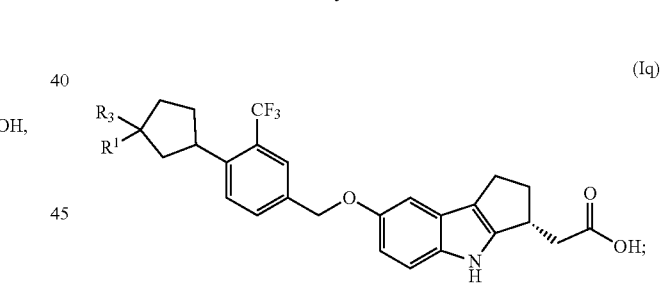
(Iq)

wherein: $R^1$ and $R^3$ have the same definitions as described herein, supra and infra.

In some embodiments, $R^1$ is OH and $R^2$ is H. Another aspect of the present invention pertains to compounds of Formula (Is) and pharmaceutically acceptable salts, solvates, and hydrates thereof:

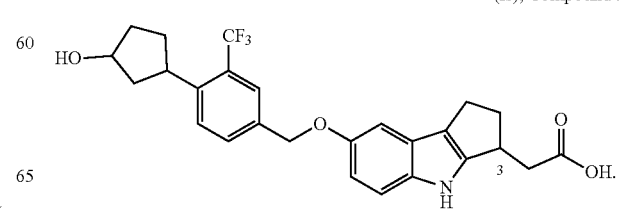
(Is), Compound 2

Some embodiments of the present invention pertain to compounds selected from 2-(7-((4-(3-hydroxycyclopentyl)-3-(trifluoromethyl)benzyl)oxy)-1,2,3,4-tetrahydrocyclopenta[b]indol-3-yl)acetic acid (Compound 2) and pharmaceutically acceptable salts, solvates, and hydrates thereof.

In some embodiments, $R^1$ and $R^2$ together is oxo. Another aspect of the present invention pertains to compounds of Formula (Iu) and pharmaceutically acceptable salts, solvates, and hydrates thereof:

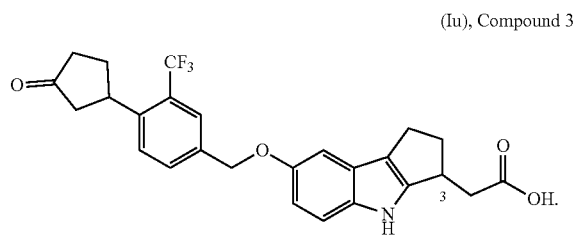 [SMILES: O=C(O)CC1CCc2c1[nH]c1ccc(OCc3ccc(C4CCC(=O)C4)c(C(F)(F)F)c3)cc21]

(Iu), Compound 3

Some embodiments of the present invention pertain to compounds selected from 2-(7-((4-(3-oxocyclopentyl)-3-(trifluoromethyl)benzyl)oxy)-1,2,3,4-tetrahydrocyclopenta[b]indol-3-yl)acetic acid (Compound 3) and pharmaceutically acceptable salts, solvates, and hydrates thereof.

In some embodiments, the present invention encompasses compounds of Formula (Iw) and pharmaceutically acceptable salts, solvates, and hydrates thereof:

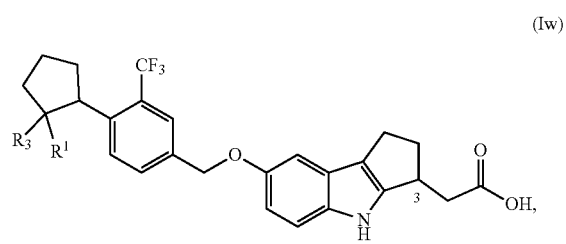

(Iw)

wherein:
$R^1$ is H or OH; and
$R^3$ is H;
or $R^1$ and $R^3$ together is oxo.

In some embodiments, the present invention encompasses compounds of Formula (Ix) and pharmaceutically acceptable salts, solvates, and hydrates thereof:

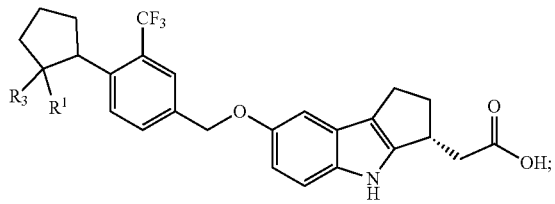

(Ix)

wherein: $R^1$ and $R^3$ have the same definitions as described herein, supra and infra.

In some embodiments, $R^1$ is OH and $R^2$ is H. Another aspect of the present invention pertains to compounds of Formula (Iy) and pharmaceutically acceptable salts, solvates, and hydrates thereof:

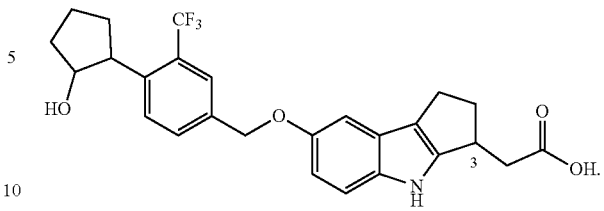

(Iy), Compound 4

Some embodiments of the present invention pertain to compounds selected from 2-(7-((4-(2-hydroxycyclopentyl)-3-(trifluoromethyl)benzyl)oxy)-1,2,3,4-tetrahydrocyclopenta[b]indol-3-yl)acetic acid (Compound 4) and pharmaceutically acceptable salts, solvates, and hydrates thereof.

In some embodiments, $R^1$ and $R^2$ together is oxo. Another aspect of the present invention pertains to compounds of Formula (Iz) and pharmaceutically acceptable salts, solvates, and hydrates thereof:

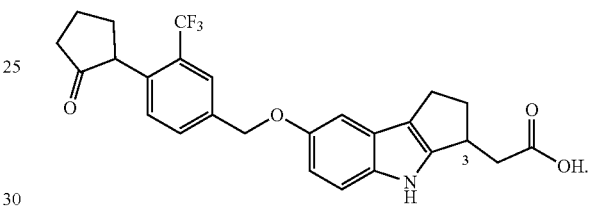

(Iz), Compound 5

Some embodiments of the present invention pertain to compounds selected from 2-(7-((4-(2-oxocyclopentyl)-3-(trifluoromethyl)benzyl)oxy)-1,2,3,4-tetrahydrocyclopenta[b]indol-3-yl)acetic acid (Compound 5) and pharmaceutically acceptable salts, solvates, and hydrates thereof.

For any formulae described herein for which the stereochemistry for a carbon is not specifically shown then it is understood that the carbon can be described to specifically show the stereochemistry as either (R) or (S).

Accordingly, in some embodiments, the stereochemistry for the C(3) carbon, as specifically shown in any of the formulae described herein (supra and infra), of the 1,2,3,4-tetrahydrocyclopenta[b]indol-3-yl group is (R). In some embodiments, the stereochemistry for the C(3) carbon, as specifically shown in any of the formulae described herein (supra and infra), of the 1,2,3,4-tetrahydrocyclopenta[b]indol-3-yl group is (S). The C(3) carbon is specifically identified in Formulae (Ia), (Ic), (Ie), (Ig), (Ii), (Ik), (Im), (Io), (Iq), (Is), (Iu), (Iw), (Ix), (Iy), and (Iz).

For clarity, the complete numbering for the carbon atoms found in the 1,2,3,4-tetrahydrocyclopenta[b]indol-3-yl group is shown below for Formula (Ia):

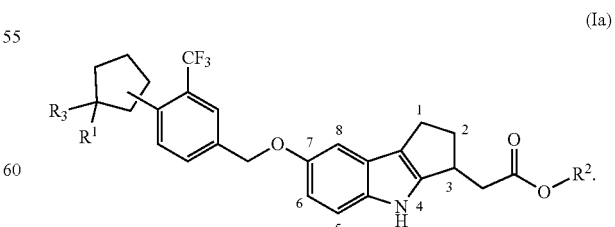

(Ia)

Some embodiments of the present invention include every combination of one or more compounds and pharmaceutically acceptable salts, solvates, and hydrates thereof selected from the following group shown in Table A.

TABLE A

| Cmpd No. | Chemical Structure<br>Chemical Name |
|---|---|
| 1 | 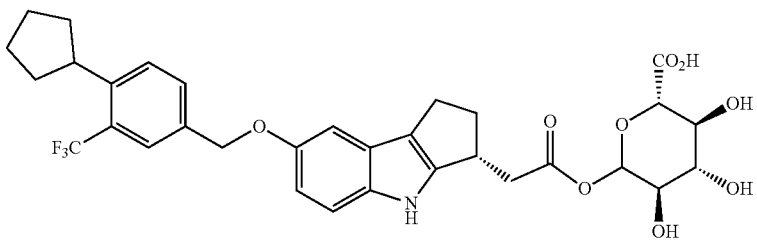<br>(2S,3S,4S,5R)-6-(2-((R)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid |
| 1A | 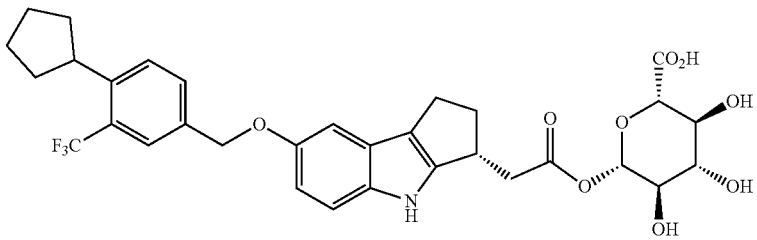<br>(2S,3S,4S,5R,6S)-6-(2-((R)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid |
| 1B | 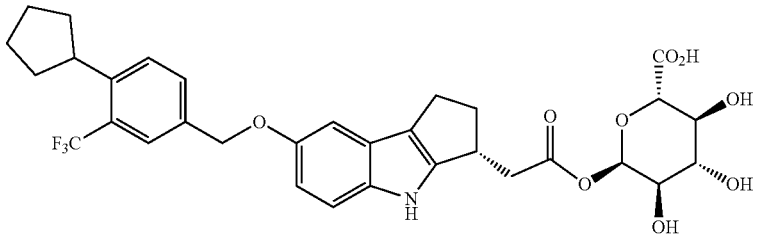<br>(2S,3S,4S,5R,6R)-6-(2-((R)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid |
| 1C | 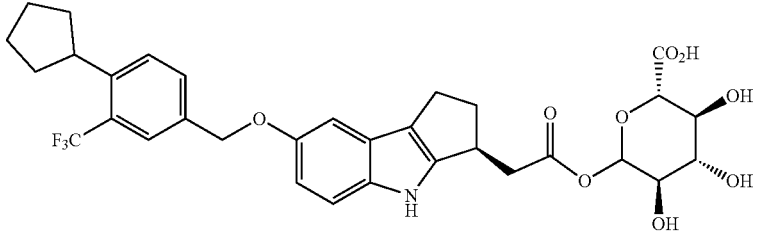<br>(2S,3S,4S,5R)-6-(2-((S)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid |

TABLE A-continued

| Cmpd No. | Chemical Structure<br>Chemical Name |
|---|---|
| 1D | 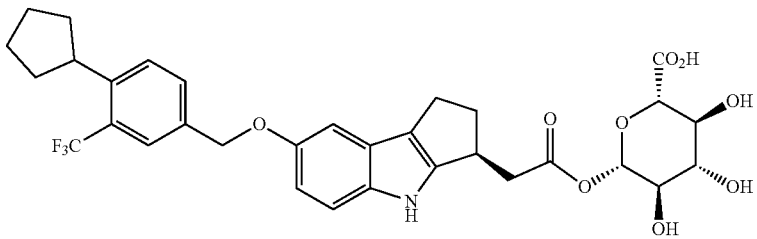<br>(2S,3S,4S,5R,6S)-6-(2-((S)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid |
| 1E | 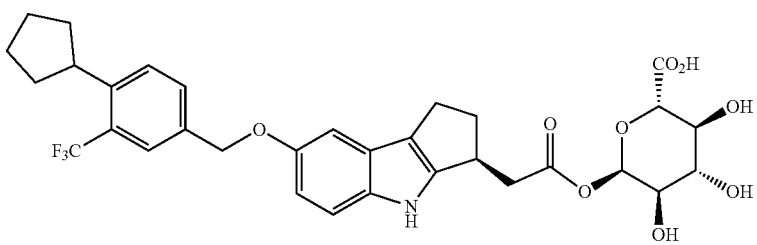<br>(2S,3SS,4S,5R,6R)-6-(2-((S)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid |
| 2 | 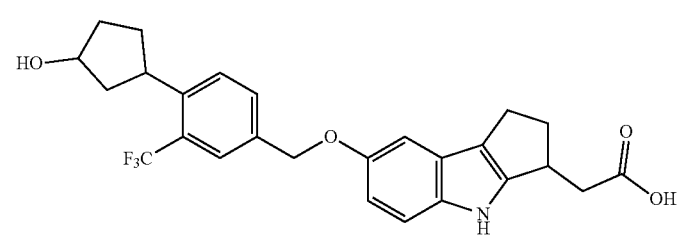<br>2-(7-((4-(3-hydroxycyclopentyl)-3-(trifluoromethyl)benzyl)oxy)-1,2,3,4-tetrahydrocyclopenta[b]indol-3-yl)acetic acid |
| 2A | 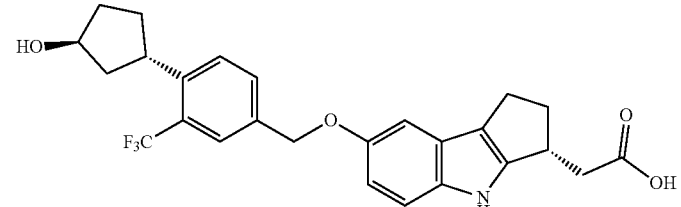<br>2-((R)-7-((4-((1S,3S)-3-hydroxycyclopentyl)-3-(trifluoromethyl)benzyl)oxy)-1,2,3,4-tetrahydrocyclopenta[b]indol-3-yl)acetic acid |
| 2B | 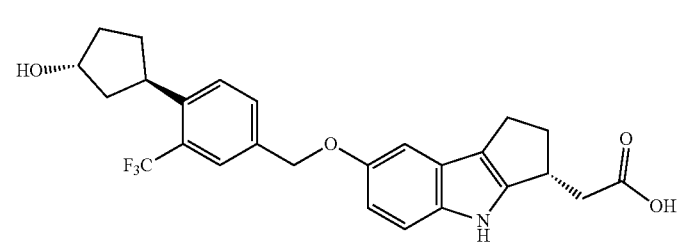<br>2-((R)-7-((4-((1R,3R)-3-hydroxycyclopentyl)-3-(trifluoromethyl)benzyl)oxy)-1,2,3,4-tetrahydrocyclopenta[b]indol-3-yl)acetic acid |

TABLE A-continued

| Cmpd No. | Chemical Structure<br>Chemical Name |
|---|---|
| 2C | 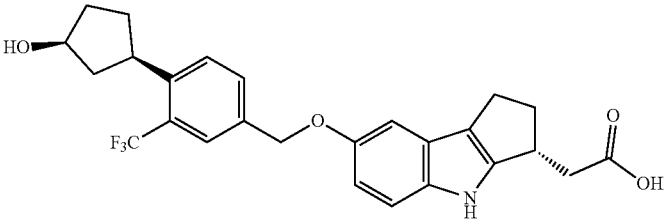<br>2-((R)-7-((4-(((1R,3S)-3-hydroxycyclopentyl)-3-(trifluoromethyl)benzyl)oxy)-1,2,3,4-tetrahydrocyclopenta[b]indol-3-yl)acetic acid |
| 2D | 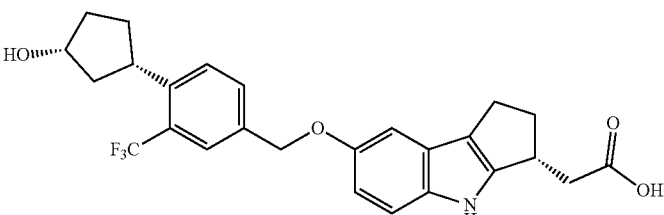<br>2-((R)-7-((4-(((1S,3R)-3-hydroxycyclopentyl)-3-(trifluoromethyl)benzyl)oxy)-1,2,3,4-tetrahydrocyclopenta[b]indol-3-yl)acetic acid |
| 2E | 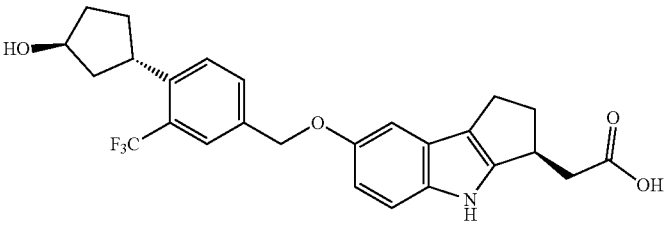<br>2-((S)-7-((4-(((1S,3S)-3-hydroxycyclopentyl)-3-(trifluoromethyl)benzyl)oxy)-1,2,3,4-tetrahydrocyclopenta[b]indol-3-yl)acetic acid |
| 2F | 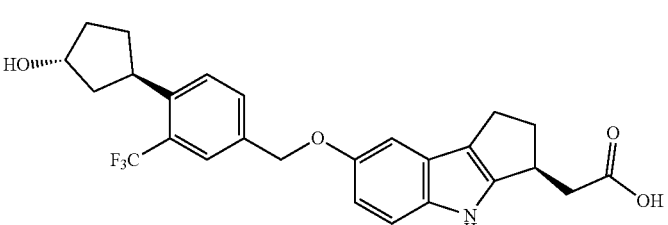<br>2-((S)-7-((4-(((1R,3R)-3-hydroxycyclopentyl)-3-(trifluoromethyl)benzyl)oxy)-1,2,3,4-tetrahydrocyclopenta[b]indol-3-yl)acetic acid |
| 2G | 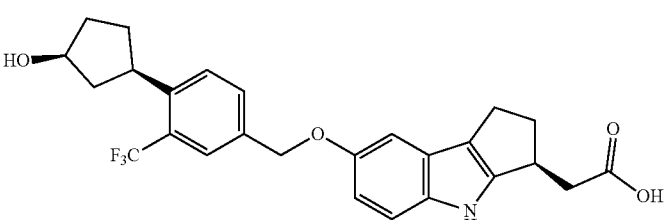<br>2-((S)-7-((4-(((1R,3S)-3-hydroxycyclopentyl)-3-(trifluoromethyl)benzyl)oxy)-1,2,3,4-tetrahydrocyclopenta[b]indol-3-yl)acetic acid |

TABLE A-continued

| Cmpd No. | Chemical Structure<br>Chemical Name |
|---|---|
| 2H | 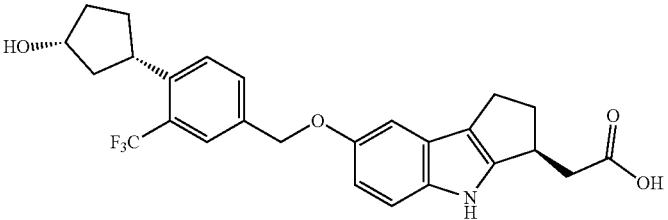<br>2-((S)-7-((4-((1S,3R)-3-hydroxycyclopentyl)-3-(trifluoromethyl)benzyl)oxy)-1,2,3,4-tetrahydrocyclopenta[b]indol-3-yl)acetic acid |
| 3 | 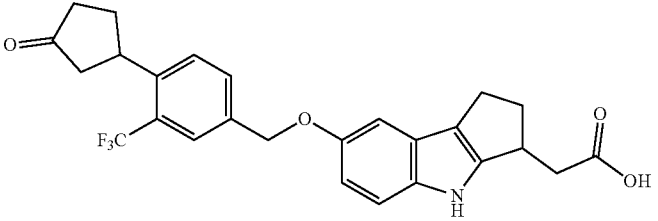<br>2-(7-((4-(3-oxocyclopentyl)-3-(trifluoromethyl)benzyl)oxy)-1,2,3,4-tetrahydrocyclopenta[b]indol-3-yl)acetic acid |
| 3A | 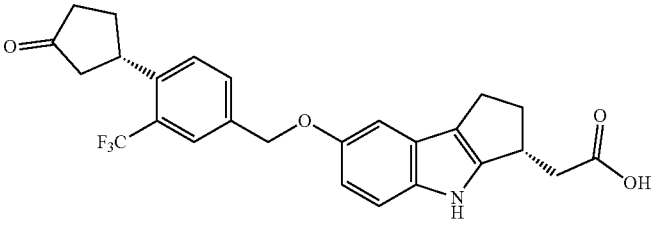<br>2-((R)-7-((4-((S)-3-oxocyclopentyl)-3-(trifluoromethyl)benzyl)oxy)-1,2,3,4-tetrahydrocyclopenta[b]indol-3-yl)acetic acid |
| 3B | 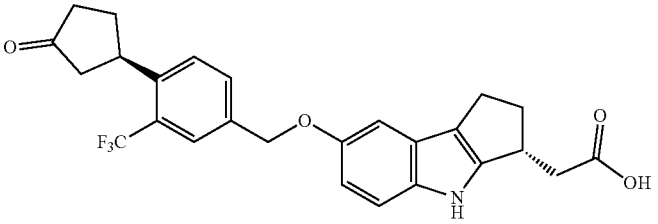<br>2-((R)-7-((4-((R)-3-oxocyclopentyl)-3-(trifluoromethyl)benzyl)oxy)-1,2,3,4-tetrahydrocyclopenta[b]indol-3-yl)acetic acid |
| 3C | 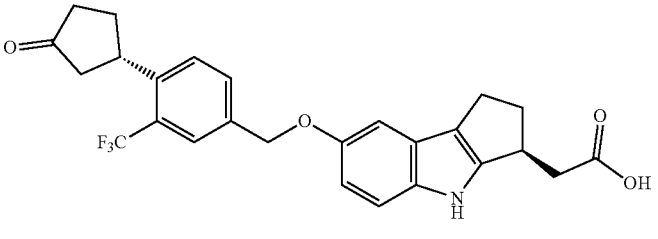<br>2-((S)-7-((4-((S)-3-oxocyclopentyl)-3-(trifluoromethyl)benzyl)oxy)-1,2,3,4-tetrahydrocyclopenta[b]indol-3-yl)acetic acid |

TABLE A-continued

| Cmpd No. | Chemical Structure Chemical Name |
|---|---|
| 3D | 2-((S)-7-((4-((R)-3-oxocyclopentyl)-3-(trifluoromethyl)benzyl)oxy)-1,2,3,4-tetrahydrocyclopenta[b]indol-3-yl)acetic acid |
| 4 | 2-(7-((4-(2-hydroxycyclopentyl)-3-(trifluoromethyl)benzyl)oxy)-1,2,3,4-tetrahydrocyclopenta[b]indol-3-yl)acetic acid |
| 4A | 2-((R)-7-((4-((1R,2S)-2-hydroxycyclopentyl)-3-(trifluoromethyl)benzyl)oxy)-1,2,3,4-tetrahydrocyclopenta[b]indol-3-yl)acetic acid |
| 4B | 2-((R)-7-((4-((1S,2R)-2-hydroxycyclopentyl)-3-(trifluoromethyl)benzyl)oxy)-1,2,3,4-tetrahydrocyclopenta[b]indol-3-yl)acetic acid |
| 4C | 2-((R)-7-((4-((1S,2S)-2-hydroxycyclopentyl)-3-(trifluoromethyl)benzyl)oxy)-1,2,3,4-tetrahydrocyclopenta[b]indol-3-yl)acetic acid |

TABLE A-continued

| Cmpd No. | Chemical Structure Chemical Name |
|---|---|
| 4D | 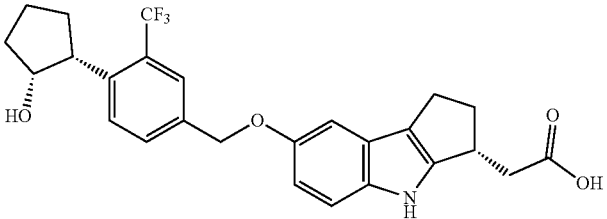<br>2-((R)-7-((4-((1R,2R)-2-hydroxycyclopentyl)-3-(trifluoromethyl)benzyl)oxy)-1,2,3,4-tetrahydrocyclopenta[b]indol-3-yl)acetic acid |
| 4E | 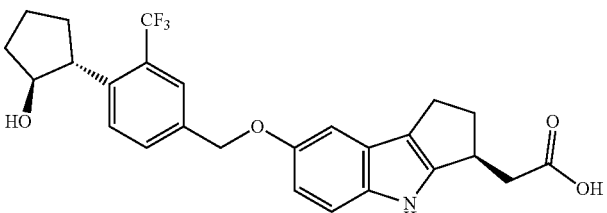<br>2-((S)-7-((4-((1R,2S)-2-hydroxycyclopentyl)-3-(trifluoromethyl)benzyl)oxy)-1,2,3,4-tetrahydrocyclopenta[b]indol-3-yl)acetic acid |
| 4F | 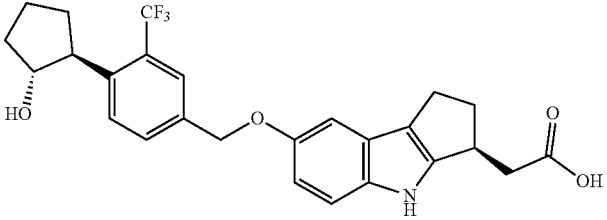<br>2-((S)-7-((4-((1S,2R)-2-hydroxycyclopentyl)-3-(trifluoromethyl)benzyl)oxy)-1,2,3,4-tetrahydrocyclopenta[b]indol-3-yl)acetic acid |
| 4G | 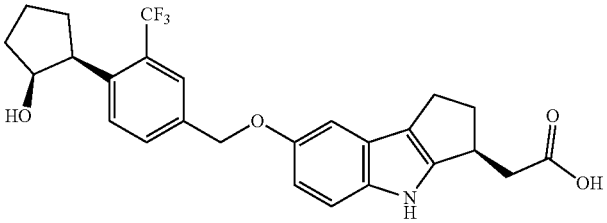<br>2-((S)-7-((4-((1S,2S)-2-hydroxycyclopentyl)-3-(trifluoromethyl)benzyl)oxy)-1,2,3,4-tetrahydrocyclopenta[b]indol-3-yl)acetic acid |
| 4H | 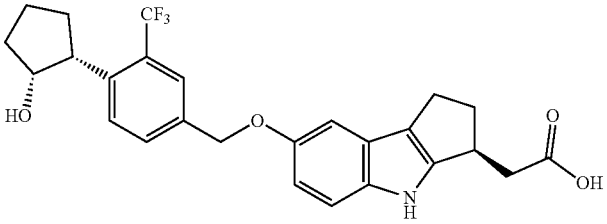<br>2-((S)-7-((4-((1R,2R)-2-hydroxycyclopentyl)-3-(trifluoromethyl)benzyl)oxy)-1,2,3,4-tetrahydrocyclopenta[b]indol-3-yl)acetic acid |

TABLE A-continued

| Cmpd No. | Chemical Structure<br>Chemical Name |
|---|---|
| 5 | 2-(7-((4-(2-oxocyclopentyl)-3-(trifluoromethyl)benzyl)oxy)-1,2,3,4-tetrahydrocyclopenta[b]indol-3-yl)acetic acid |
| 5A | 2-((R)-7-((4-((R)-2-oxocyclopentyl)-3-(trifluoromethyl)benzyl)oxy)-1,2,3,4-tetrahydrocyclopenta[b]indol-3-yl)acetic acid |
| 5B | 2-((R)-7-((4-((S)-2-oxocyclopentyl)-3-(trifluoromethyl)benzyl)oxy)-1,2,3,4-tetrahydrocyclopenta[b]indol-3-yl)acetic acid |
| 5C | 2-((S)-7-((4-((R)-2-oxocyclopentyl)-3-(trifluoromethyl)benzyl)oxy)-1,2,3,4-tetrahydrocyclopenta[b]indol-3-yl)acetic acid |
| 5D | 2-((S)-7-((4-((S)-2-oxocyclopentyl)-3-(trifluoromethyl)benzyl)oxy)-1,2,3,4,-tetrahydrocyclopenta[b]indol-3-yl)acetic acid |

TABLE A-continued

| Cmpd No. | Chemical Structure<br>Chemical Name |
|---|---|
| 6 | 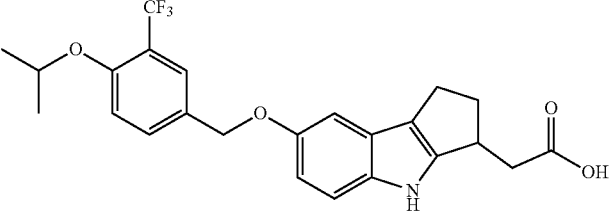<br>2-(7-((4-isopropoxy-3-(trifluoromethyl)benzyl)oxy)-1,2,3,4-tetrahydrocyclopenta[b]indol-3-yl)acetic acid |
| 6A | 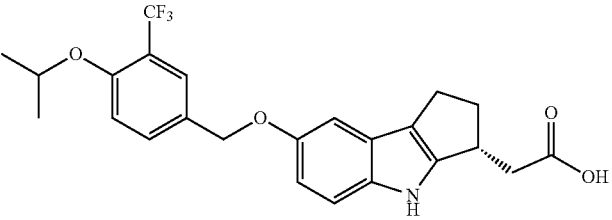<br>(R)-2-(7-((4-isopropoxy-3-(trifluoromethyl)benzyl)oxy)-1,2,3,4-tetrahydrocyclopenta[b]indol-3-yl)acetic acid |
| 6B | 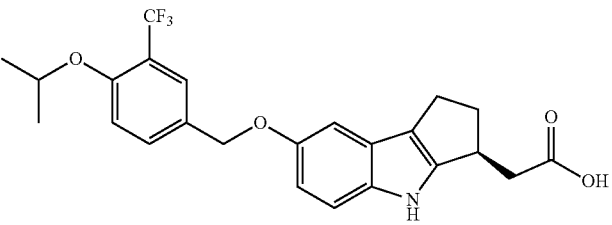<br>(S)-2-(7-((4-isopropoxy-3-(trifluoromethy)benzyl)oxy)-1,2,3,4-tetrahydrocyclopenta[b]indol-3-yl)acetic acid |

Some embodiments of the present invention include every combination of one or more compounds selected from the following compounds and pharmaceutically acceptable salts, solvates, and hydrates thereof:

(2S,3S,4S,5R)-6-(2-((R)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid;

(2S,3S,4S,5R,6S)-6-(2-((R)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid;

(2S,3S,4S,5R,6R)-6-(2-((R)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid;

(2S,3S,4S,5R)-6-(2-((S)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid;

(2S,3S,4S,5R,6S)-6-(2-((S)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid;

(2S,3S,4S,5R,6R)-6-(2-((S)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid;

2-(7-((4-(3-hydroxycyclopentyl)-3-(trifluoromethyl)benzyl)oxy)-1,2,3,4-tetrahydrocyclopenta[b]indol-3-yl)acetic acid;

2-((R)-7-((4-((1S,3S)-3-hydroxycyclopentyl)-3-(trifluoromethyl)benzyl)oxy)-1,2,3,4-tetrahydrocyclopenta[b]indol-3-yl)acetic acid;

2-((R)-7-((4-((1R,3R)-3-hydroxycyclopentyl)-3-(trifluoromethyl)benzyl)oxy)-1,2,3,4-tetrahydrocyclopenta[b]indol-3-yl)acetic acid;

2-((R)-7-((4-((1R,3S)-3-hydroxycyclopentyl)-3-(trifluoromethyl)benzyl)oxy)-1,2,3,4-tetrahydrocyclopenta[b]indol-3-yl)acetic acid;

2-((R)-7-((4-((1S,3R)-3-hydroxycyclopentyl)-3-(trifluoromethyl)benzyl)oxy)-1,2,3,4-tetrahydrocyclopenta[b]indol-3-yl)acetic acid;

2-((S)-7-((4-((1S,3S)-3-hydroxycyclopentyl)-3-(trifluoromethyl)benzyl)oxy)-1,2,3,4-tetrahydrocyclopenta[b]indol-3-yl)acetic acid;

2-((S)-7-((4-((1R,3R)-3-hydroxycyclopentyl)-3-(trifluoromethyl)benzyl)oxy)-1,2,3,4-tetrahydrocyclopenta[b]indol-3-yl)acetic acid;

2-((S)-7-((4-((1R,3S)-3-hydroxycyclopentyl)-3-(trifluoromethyl)benzyl)oxy)-1,2,3,4-tetrahydrocyclopenta[b]indol-3-yl)acetic acid;

2-((S)-7-((4-((1S,3R)-3-hydroxycyclopentyl)-3-(trifluoromethyl)benzyl)oxy)-1,2,3,4-tetrahydrocyclopenta[b]indol-3-yl)acetic acid;

2-(7-((4-(3-oxocyclopentyl)-3-(trifluoromethyl)benzyl)oxy)-1,2,3,4-tetrahydrocyclopenta[b]indol-3-yl)acetic acid;

2-((R)-7-((4-((S)-3-oxocyclopentyl)-3-(trifluoromethyl)benzyl)oxy)-1,2,3,4-tetrahydrocyclopenta[b]indol-3-yl)acetic acid;

2-((R)-7-((4-((R)-3-oxocyclopentyl)-3-(trifluoromethyl)benzyl)oxy)-1,2,3,4-tetrahydrocyclopenta[b]indol-3-yl)acetic acid;

2-((S)-7-((4-((S)-3-oxocyclopentyl)-3-(trifluoromethyl)benzyl)oxy)-1,2,3,4-tetrahydrocyclopenta[b]indol-3-yl)acetic acid;

2-((S)-7-((4-((R)-3-oxocyclopentyl)-3-(trifluoromethyl)benzyl)oxy)-1,2,3,4-tetrahydrocyclopenta[b]indol-3-yl)acetic acid;

2-(7-((4-(2-hydroxycyclopentyl)-3-(trifluoromethyl)benzyl)oxy)-1,2,3,4-tetrahydrocyclopenta[b]indol-3-yl)acetic acid;

2-((R)-7-((4-((1R,2S)-2-hydroxycyclopentyl)-3-(trifluoromethyl)benzyl)oxy)-1,2,3,4-tetrahydrocyclopenta[b]indol-3-yl)acetic acid;

2-((R)-7-((4-((1S,2R)-2-hydroxycyclopentyl)-3-(trifluoromethyl)benzyl)oxy)-1,2,3,4-tetrahydrocyclopenta[b]indol-3-yl)acetic acid;

2-((R)-7-((4-((1S,2S)-2-hydroxycyclopentyl)-3-(trifluoromethyl)benzyl)oxy)-1,2,3,4-tetrahydrocyclopenta[b]indol-3-yl)acetic acid;

2-((R)-7-((4-((1R,2R)-2-hydroxycyclopentyl)-3-(trifluoromethyl)benzyl)oxy)-1,2,3,4-tetrahydrocyclopenta[b]indol-3-yl)acetic acid;

2-((S)-7-((4-((1R,2S)-2-hydroxycyclopentyl)-3-(trifluoromethyl)benzyl)oxy)-1,2,3,4-tetrahydrocyclopenta[b]indol-3-yl)acetic acid;

2-((S)-7-((4-((1S,2R)-2-hydroxycyclopentyl)-3-(trifluoromethyl)benzyl)oxy)-1,2,3,4-tetrahydrocyclopenta[b]indol-3-yl)acetic acid;

2-((S)-7-((4-((1S,2S)-2-hydroxycyclopentyl)-3-(trifluoromethyl)benzyl)oxy)-1,2,3,4-tetrahydrocyclopenta[b]indol-3-yl)acetic acid;

2-((S)-7-((4-((1R,2R)-2-hydroxycyclopentyl)-3-(trifluoromethyl)benzyl)oxy)-1,2,3,4-tetrahydrocyclopenta[b]indol-3-yl)acetic acid;

2-(7-((4-(2-oxocyclopentyl)-3-(trifluoromethyl)benzyl)oxy)-1,2,3,4-tetrahydrocyclopenta[b]indol-3-yl)acetic acid;

2-((R)-7-((4-((R)-2-oxocyclopentyl)-3-(trifluoromethyl)benzyl)oxy)-1,2,3,4-tetrahydrocyclopenta[b]indol-3-yl)acetic acid;

2-((R)-7-((4-((S)-2-oxocyclopentyl)-3-(trifluoromethyl)benzyl)oxy)-1,2,3,4-tetrahydrocyclopenta[b]indol-3-yl)acetic acid;

2-((S)-7-((4-((R)-2-oxocyclopentyl)-3-(trifluoromethyl)benzyl)oxy)-1,2,3,4-tetrahydrocyclopenta[b]indol-3-yl)acetic acid;

2-((S)-7-((4-((S)-2-oxocyclopentyl)-3-(trifluoromethyl)benzyl)oxy)-1,2,3,4-tetrahydrocyclopenta[b]indol-3-yl)acetic acid;

2-(7-((4-isopropoxy-3-(trifluoromethyl)benzyl)oxy)-1,2,3,4-tetrahydrocyclopenta[b]indol-3-yl)acetic acid;

(R)-2-(7-((4-isopropoxy-3-(trifluoromethyl)benzyl)oxy)-1,2,3,4-tetrahydrocyclopenta[b]indol-3-yl)acetic acid; and (S)-2-(7-((4-isopropoxy-3-(trifluoromethyl)benzyl)oxy)-1,2,3,4-tetrahydrocyclopenta[b]indol-3-yl)acetic acid.

Additionally, individual compounds and those compounds of Formulae (Ia), (Ic), (Ie), (Ig), (Ii), (Ik), (Im), (Io), (Iq), (Is), (Iu), (Iw), (Ix), (Iy), and/or (Iz) including diastereomers and enantiomers thereof, encompass all pharmaceutically acceptable salts, solvates, and hydrates, thereof.

It is understood that the present invention embraces each diastereomer, each enantiomer and mixtures thereof of each compound of Formulae (Ia), (Ic), (Ie), (Ig), (Ii), (Ik), (Im), (Io), (Iq), (Is), (Iu), (Iw), (Ix), (Iy), and/or (Iz) disclosed herein just as if they were each individually disclosed with the specific stereochemical designation for each chiral carbon. Separation of the individual isomers (such as, by chiral HPLC, recrystallization of diastereomeric mixtures and the like) or selective synthesis (such as, by enantiomeric selective syntheses and the like) of the individual isomers is accomplished by application of various methods which are well known to practitioners in the art.

The compounds of the Formulae (Ia), (Ic), (Ie), (Ig), (Ii), (Ik), (Im), (Io), (Iq), (Is), (Iu), (Iw), (Ix), (Iy), and/or (Iz) of the present invention may be prepared according to relevant published literature procedures that are used by one skilled in the art. Exemplary reagents and procedures for these reactions appear hereinafter in the working examples. Protection and deprotection, as needed, may be carried out by procedures generally known in the art (see, for example, Greene, T. W. and Wuts, P. G. M., *Protecting Groups in Organic Synthesis*, 3$^{rd}$ Edition, 1999 [Wiley]; incorporated herein by reference in its entirety).

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.)

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt, solvate, hydrate or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use; in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or suspensions, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a salt, solvate, hydrate or physiologically functional derivative thereof can be used as active ingredients in pharmaceutical compositions, specifically as S1P1 receptor modulators. The term "active ingredient" is defined in the context of a "pharmaceutical composition" and refers to a component of a pharmaceutical composition that provides the primary pharmacological effect, as opposed to an "inactive ingredient" which would generally be recognized as providing no pharmaceutical benefit.

The dose when using the compounds of the present invention can vary within wide limits and as is customary and known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate by the patient's physician or caregiver it may be necessary to deviate upward or downward from the doses described herein.

The amount of active ingredient or an active salt, solvate or hydrate derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in one model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, whether an acute or chronic disease state is being treated or prophylaxis is conducted or whether further active compounds are administered in addition to the compounds of the present invention and as part of a drug combination. The dosage regimen for treating a disease condition with the compounds and/or compositions of this invention is selected in accordance with a variety factors including those cited above. Thus, the actual dosage regimen employed may vary widely and therefore may deviate from a preferred dosage regimen and one skilled in the art will recognize that dosage and dosage regimens outside these typical ranges can be tested and, where appropriate, may be used in the methods of this invention.

The desired dose may conveniently be presented in a single dose or as divided doses administered at appropriate intervals, for example, as 2, 3, 4 or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4-part administrations. If appropriate, depending on individual behavior, it may be necessary to deviate upward or downward from the daily dose indicated.

For preparing pharmaceutical compositions from the compounds of the present invention, the suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or encapsulating materials.

In powders, the carrier is a finely divided solid which is in a mixture with the finely divided active component.

In tablets, the active component is mixed with the carrier having the necessary binding capacity in suitable proportions and compacted to the desired shape and size.

The powders and tablets may contain varying percentage amounts of the active compound. A representative amount in a powder or tablet may be from 0.5 to about 90 percent of the active compound. However, an artisan would know when amounts outside of this range are necessary. Suitable carriers for powders and tablets include magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein (e.g., by stirring). The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising the active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols (e.g., nasal aerosols, by inhalation), this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. Solutions or dispersions of the compounds of the present invention or a pharmaceutically acceptable salt, solvate, hydrate or derivative thereof in water, water/alcohol mixtures or suitable saline solutions, for example, can be employed using customary additives (e.g., benzyl alcohol or other suitable preservatives), absorption enhancers for increasing the bioavailability, solubilizers, dispersants and others and, if appropriate, customary propellants (e.g., carbon dioxide, CFCs, such as, dichlorodifluoromethane, trichlorofluoromethane, dichlorotetrafluoroethane and the like). The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively, the active ingredients may be provided in the form of a dry powder (e.g., a powder mix of the compound in a suitable powder base such as lactose, starch, starch derivatives such as hydroxypropylmethyl cellulose and polyvinylpyrrolidone (PVP)). Conveniently the powder carrier will form a gel in the nasal cavity. The powder composition may be presented in unit dose form (e.g., capsules, cartridges) as for gelatin or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

In some embodiments, the compositions are tablets or capsules for oral administration.

In some embodiments, the compositions are liquids for intravenous administration.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like, such as those pharmaceutically acceptable salts listed by Berge et al., *Journal of Pharmaceutical Sciences*, 66:1-19 (1977), incorporated herein by reference in its entirety.

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and that when administered into an individual undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when S1P1 receptor agonists are utilized as active ingredients in a pharmaceutical composition, these are not intended for use only in humans, but in other non-human mammals as well. Indeed, recent advances in the area of animal health-care mandate that consideration be given for the use of active agents, such as S1P1 receptor agonists, for the treatment of an S1P1 receptor-associated disease or disorder in companionship animals (e.g., cats, dogs, etc.) and in livestock animals (e.g., cows, chickens, fish, etc.). Those of ordinary skill in the art are readily credited with understanding the utility of such compounds in such settings.

Hydrates and Solvates

It is understood that when the phrase "pharmaceutically acceptable salts, solvates, and hydrates" is used in reference to a particular formula herein, it is intended to embrace solvates and/or hydrates of compounds of the particular formula, pharmaceutically acceptable salts of compounds of the particular formula as well as solvates and/or hydrates of pharmaceutically acceptable salts of compounds of the particular formula. It is also understood by a person of ordinary skill in the art that hydrates are a subgenus of solvates.

The compounds of the present invention can be administrated in a wide variety of oral and parenteral dosage forms. It will be apparent to those skilled in the art that the following dosage forms may comprise, as the active component, either a compound of the invention or a pharmaceutically acceptable salt or as a solvate or hydrate thereof. Moreover, various hydrates and solvates of the compounds of the invention and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: *Polymorphism in Pharmaceutical Solids*, ed. Harry G. Brittan, Vol. 95, Marcel Dekker, Inc., New York, 1999, incorporated herein by reference in its entirety. Accordingly, one aspect of the present invention pertains to hydrates and solvates of compounds of the present invention and/or their pharmaceutical acceptable salts, as described herein, that can be isolated and characterized by methods known in the art, such as, thermogravimetric analysis (TGA), TGA-mass spectroscopy, TGA-Infrared spectroscopy, powder X-ray diffraction (PXRD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

Other Utilities

Another object of the present invention relates to radiolabeled compounds of the present invention that are useful not only in radio-imaging but also in assays, both in vitro and in vivo, for localizing and quantitating the S1P1 receptor in tissue samples, including human and for identifying S1P1 receptor ligands by inhibition binding of a radiolabeled compound. It is a further object of this invention to develop novel S1P1 receptor assays which comprise such radiolabeled compounds.

The present invention embraces isotopically-labeled compounds of the present invention. Isotopically or radiolabeled compounds are those which are identical to compounds disclosed herein, but for the fact that one or more atoms are replaced or substituted by an atom having an atomic mass or mass number different from the atomic mass or mass number most commonly found in nature. Suitable radionuclides that may be incorporated in compounds of the present invention include, but are not limited, to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{75}$Br, $^{76}$Br, $^{77}$Br, $^{82}$Br, $^{123}$I, $^{124}$I, $^{125}$I and $^{131}$I. The radionuclide that is incorporated in the instant radiolabeled compounds will depend on the specific application of that radiolabeled compound. For example, for in vitro S1P1 receptor labeling and competition assays, compounds that incorporate 3H, $^{14}$C, $^{82}$Br, $^{125}$I, $^{131}$I or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radiolabeled" or "labeled compound" is a compound of Formulae (Ia), (Ic), (Ie), (Ig), (Ii), (Ik), (Im), (Io), (Iq), (Is), (Iu), (Iw), (Ix), (Iy), and/or (Iz) containing at least one radionuclide. In some embodiments the radionuclide is selected from the group consisting of $^3$H, $^{14}$C, $^{125}$I, $^{35}$S and $^{82}$Br.

Certain isotopically-labeled compounds of the present invention are useful in compound and/or substrate tissue distribution assays. In some embodiments the radionuclide $^3$H and/or $^{14}$C isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in FIGS. 1A, 1B, and/or 1C and examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or a scarcer radio-isotope or nonradioactive isotope.

Synthetic methods for incorporating radio-isotopes into organic compounds are applicable to compounds of the invention and are well known in the art. Certain synthetic methods, for example, for incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3$H]: This procedure is rather inexpensive and requires precursors containing reducible functional groups such as aldehydes, ketones, lactones, esters and the like.

C. Reduction with Lithium Aluminum Hydride [$^3$H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

A radiolabeled S1P1 receptor compound of Formulae (Ia), (Ic), (Ie), (Ig), (Ii), (Ik), (Im), (Io), (Iq), (Is), (Iu), (Iw), (Ix), (Iy), and/or (Iz) can be used in a screening assay to identify/evaluate compounds. In general terms, a newly synthesized or identified compound (i.e., test compound) can be evaluated for its ability to reduce binding of the "radiolabeled compound of Formulae (Ia), (Ic), (Ie), (Ig), (Ii), (Ik), (Im), (Io), (Iq), (Is), (Iu), (Iw), (Ix), (Iy), and/or (Iz) to the S1P1 receptor. Accordingly, the ability of a test compound to compete with the "radiolabeled compound of Formulae (Ia), (Ic), (Ie), (Ig), (Ii), (Ik), (Im), (Io), (Iq), (Is), (Iu), (Iw), (Ix), (Iy), and/or (Iz) for the binding to the S1P1 receptor directly correlates to its binding affinity.

The labeled compounds of the present invention bind to the S1P1 receptor. In one embodiment the labeled compound has an IC$_{50}$ less than about 500 µM, in another embodiment the labeled compound has an IC$_{50}$ less than about 100 µM, in yet another embodiment the labeled compound has an IC$_{50}$ less than about 10 µM, in yet another embodiment the labeled compound has an IC$_{50}$ less than about 1 µM and in still yet another embodiment the labeled inhibitor has an IC$_{50}$ less than about 0.1 µM.

Other uses of the disclosed receptors and methods will become apparent to those of skill in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1: Syntheses of Compounds of the Present Invention

Figure 1B:
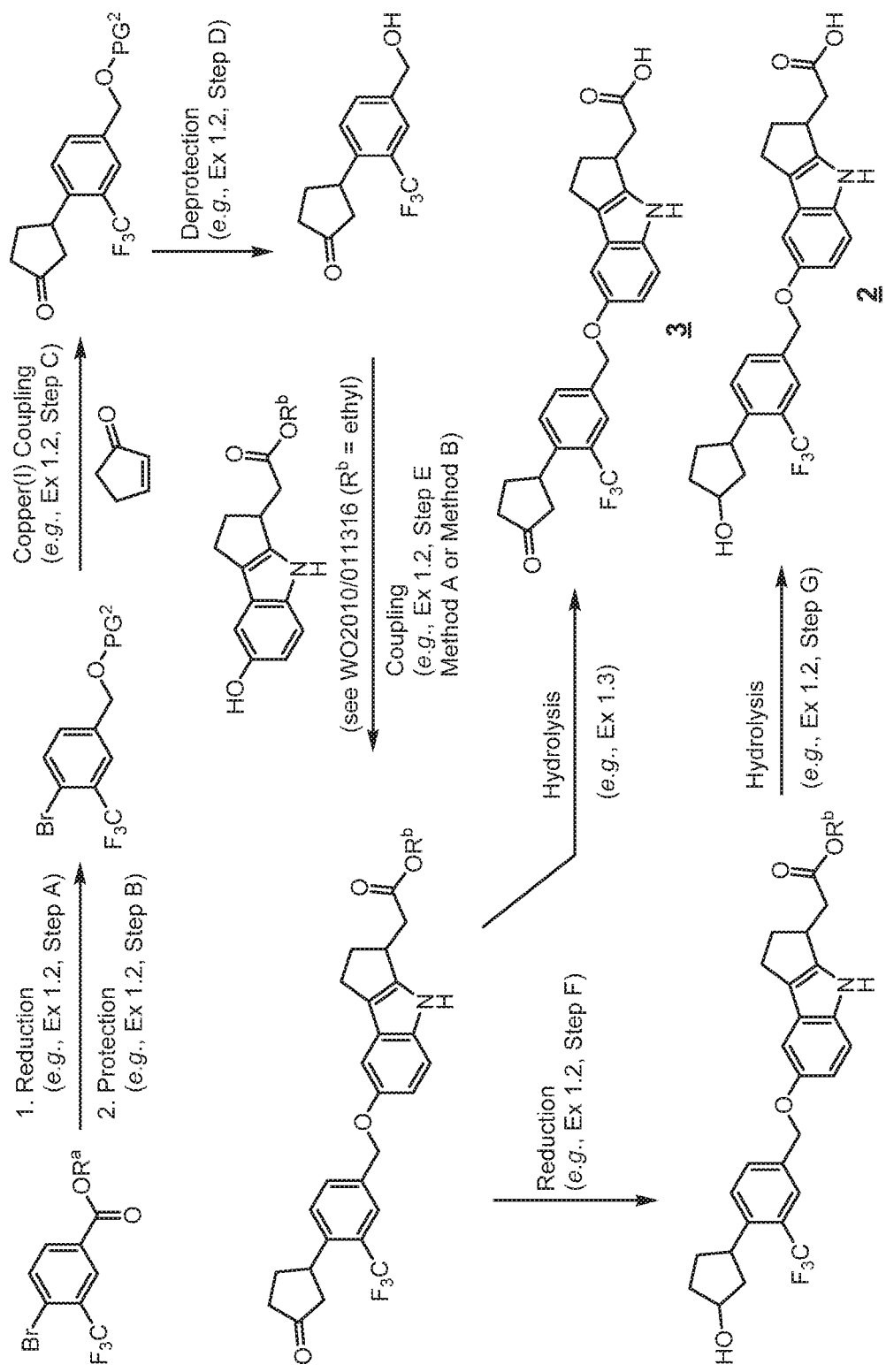
FIG. 1B shows a representative synthetic scheme for the preparation of compounds of the present invention, such as Compound 2 and Compound 3, wherein Ra and $R^b$ are independently $C_1$-$C_6$ alkyl and $PG^2$ is a protecting group (e.g., tert-butyldimethylsilyl group as described in Example 1.2, Step B). See WO2010/011316 for the synthesis of ethyl 2-(7-hydroxy-1,2,3,4-tetrahydrocyclopenta[b]indol-3-yl)acetate ($R^b$ is ethyl).
Figure 1C:
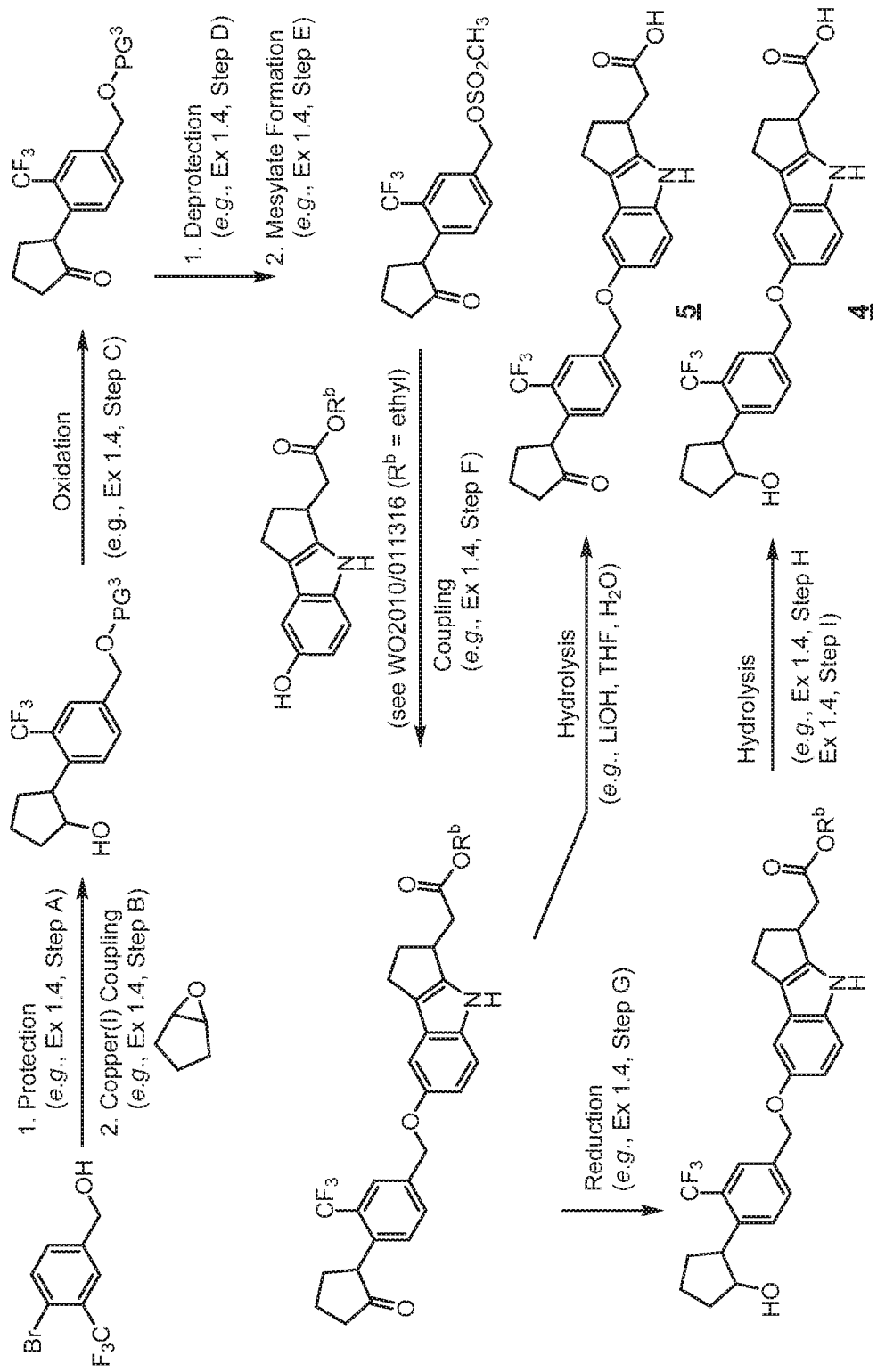
FIG. 1C shows a representative synthetic scheme for the preparation of compounds of the present invention, such as Compound 4 and Compound 5, wherein $R^b$ is $C_1$-$C_6$ alkyl (e.g., ethyl) and $PG^3$ is a protecting group (e.g., tert-butyldimethylsilyl group as described in Example 1.4, Step A). See WO2010/011316 for the synthesis of ethyl 2-(7-hydroxy-1,2,3,4-tetrahydrocyclopenta[b]indol-3-yl)acetate ($R^b$ is ethyl).

Illustrated syntheses for compounds of the present invention are shown in FIGS. 1A, 1B, and 1C.

The compounds of the invention and their syntheses are further illustrated by the following examples. The following examples are provided to further define the invention without, however, limiting the invention to the particulars of these examples. The compounds described herein, supra and infra, are named according to ChemDraw® Professional (Version 17.0.0.206). In certain instances, common names are used, and it is understood that these common names would be recognized by those skilled in the art.

Chemistry: Proton nuclear magnetic resonance ($^1$H NMR) spectra were recorded on a Bruker Avance-400 equipped with a QNP (Quad Nucleus Probe) or a BBI (Broad Band Inverse) and z-gradient. Proton nuclear magnetic resonance ($^1$H NMR) spectra were also recorded on a Bruker Avance-500 equipped a BBI (Broad Band Inverse) and z-gradient. Chemical shifts are given in parts per million (ppm) with the residual solvent signal used as reference. NMR abbreviations are used as follows: s=singlet, d=doublet, dd=doublet of doublets, t=triplet, q=quartet, m=multiplet, bs=broad singlet. Microwave irradiations were carried out using a Smith Synthesizer™ or an Emrys Optimizer™ (Biotage). Thin-layer chromatography (TLC) was performed on silica gel 60 $F_{254}$ (Merck), preparatory thin-layer chromatography (prep TLC) was preformed on PK6F silica gel 60 A 1 mm plates (Whatman) and column chromatography was carried out on a silica gel column using Kieselgel 60, 0.063-0.200 mm (Merck). Evaporation was done under reduced pressure on a Büchi rotary evaporator. Celite® 545 was used for filtration of palladium.

LCMS spec: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2.

Example 1.1: Preparation of (2S,3S,4S,5R)-6-(2-((R)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid (Compound 1)

Step A: Preparation of 1-Cyclopentyl-2-(trifluoromethyl)benzene

To a 50 L three-neck round-bottom flask equipped with a mechanical stirrer, thermocouple, and nitrogen inlet, was added dry THF (35 L) and cooled to 0-5° C. To the flask was added Iron (III) chloride (2.7 kg, 0.15 eq) portion wise over 30-60 min. and stirred for 15-30 min. resulting in a clear greenish solution. Under a nitrogen atmosphere in a dry 100-gallon glass lined reactor was added THF (87.5 L) and magnesium turnings (4.05 kg, 1.5 eq), and cooled to 0-5° C. To the THF and magnesium mixture was added the solution of $FeCl_3$ in THF at a rate to maintain the internal temperature below 10° C. To the resulting yellow/green mixture was added TMEDA (15.5 kg, 1.2 eq) at a rate to maintain the internal temperature below 20° C. The resulting reaction mixture was heated to 40-45° C. for 1 hour and a mixture of 1 bromo-2-(trifluoromethyl) benzene (25 kg, 1.0 eq) and bromocyclopentane (19.9 kg, 1.2 eq) was added to the reaction mixture at a rate to maintain an internal temperature below 25° C. The resulting reaction mixture was allowed to stir at room temperature overnight and subsequently cooled to an internal temperature of 0-5° C. To the resulting mixture was added 6 N HCl (100 L, 1.5 h) at such a rate as to maintain the internal temperature below 15° C. (caution, very exothermic). After the quench, MTBE (200 L) was added and the reactor contents was stirred for 30 min. The phases were separated, and the aqueous layer back extracted with MTBE (75 L). The combined organic layers were washed with $H_2O$ (50 L), brine (50 L) and dried ($MgSO_4$). The mixture was filtered through an in-line (1 micron) filter cartridge followed by an additional in-line (0.45 micron) filter cartridge into a clean dry reactor. The solvent was evaporated under vacuum (jacket ≤30° C.) and co-evaporated with heptanes (2×25 L) to provide a viscous liquid. The viscous liquid was dissolved in heptanes (100 L) and passed through a silica plug (25 kg). The silica plug was eluted with heptanes (TLC, $R_f$-0.8, silica gel, heptanes) and the fractions containing the product were evaporated to provide the title compound as a yellow liquid, 11.7 kg (49.2%), purity as determined by HPLC was 94.1%. $^1H$ NMR conforms to reference standard.

Step B: Preparation of 4-(Chloromethyl)-1-cyclopentyl-2-(trifluoromethyl)benzene To a 100-gallon glass lined reactor equipped with a stirrer was added concentrated sulphuric acid (48.6 L) and cooled to an internal temperature between about −5 to −10° C. under an atmosphere of $N_2$. To the sulfuric acid was added thionyl chloride (26.99 kg, 2 eq) at a rate to maintain the internal temperature below −5° C. To the resulting mixture 1,3,5-trioxane (15.3 kg, 1.5 eq) was added portion wise at a rate to maintain the internal temperature below −5° C. After the addition of 1,3,5-trioxane, 1-cyclopentyl-2-(trifluoromethyl) benzene (24.0 kg) was added drop wise over a period of approximately 2-3 hours. The reaction mixture was stirred at 0° C. for approximately 3-4 hours, allowed to warm to room temperature overnight and subsequently cooled to an internal temperature of 0-5° C. To the resulting mixture was added water (316 L) drop wise over a period of approximately 5-6 hours (Note: Very exothermic). After the quench with water, the resulting aqueous mixture was extracted with MTBE (243 L and 123 L). The combined organics were washed with saturated $NaHCO_3$ (100 L), brine (100 L), water (100 L), brine (100 L), and dried ($MgSO_4$). The mixture was filtered through an in-line (1 micron) filter cartridge followed by an additional in-line (0.45 micron) filter cartridge into a clean dry reactor. The solvent was evaporated under vacuum (jacket ≤30° C.) and further evaporated under vacuum at 35-40° C. The resulting oil was distilled under high vacuum to provide the title compound as a yellow liquid, 24.8 kg (83%), purity as determined by HPLC was 99.47%. $^1H$ NMR conforms to reference standard.

Step C: Preparation of Ethyl 2-(2-Morpholinocyclopent-2-enylidene) Acetate

Cyclopentanone (22.00 kg), morpholine (22.88 kg) and cyclohexane (43.78 kg) were charged to a 400 L glass-lined reactor equipped with overhead agitation, jacket temperature control, a nitrogen inlet, and a Dean-Stark trap. The reactor contents were heated to about 85° C. to 95° C. for approximately 26 h while removing water using the Dean-Stark trap. The reaction to form the enamine (i.e., 4-(cyclopent-1-en-1-yl)morpholine) is deemed complete when the morpholine amount is verified to be 3% by GC peak area.

The reactor contents were cooled to about 60° C. and ethyl glyoxalate; 58.74 kg, 50% solution in toluene) was added to the mixture slowly so as to maintain an internal temperature of ≤80° C. The reactor contents were heated to about 85° C. to 95° C. for at least 25 hours while removing water using the Dean-Stark trap. The reaction was deemed complete when the eneamine (i.e., 4-cyclopentenylmorpholine) amount by GC was verified to be less than 0.5% by GC peak area. The cyclohexane/toluene mixture was distilled under vacuum, ethanol (261.80 kg) was charged to the reactor, and the resulting solution was again distilled under vacuum. Ethanol (34.76 kg) and water 44.00 kg) were charged to the reactor and the reactor contents stirred at 25° C. The mixture was stirred further for 6 h at about 0-5° C.

The resulting product slurry was collected by filtration, washed with aqueous ethanol (34.76 kg ethanol dissolved in 176.00 kg water). The filter-cake was further washed with water (110.00 kg), dried initially at approximately 36° C. for 1 hour under vacuum and subsequently at approximately 50° C. under vacuum for 17 h. The title compound was obtained as a tan solid (23.48 kg, 37.8% yield).

Step D: Preparation of E/Z Ethyl 2-(7-(Benzyloxy)-1,2-dihydrocyclopenta[b]indol-3(4H)-ylidene)acetate To a 400 L glass-lined reactor equipped with overhead agitation, jacket temperature control, and a nitrogen inlet was added (4-(benzyloxy)phenyl)hydrazine hydrochloride (21.08 kg, 1.000 mole equiv.), ethyl 2-(2-morpholinocyclopent-2-enylidene)acetate (22.02 kg, 1.104 mole equiv.), ethanol (51.2 kg, 2.429 mass equiv.), and acetic acid (36.8 kg, 1.746 mass eq.). After the reactor contents are allowed to stand for 10 minutes, agitation and then heating to 60° C. to 65° C. (60° C. target) was started. While stirring at that temperature, samples of the reaction mixture were taken over intervals of approximately 30 minutes and analyzed by HPLC for (4-(benzyloxy)phenyl)hydrazine, ethyl 2-(2-morpholinocyclopent-2-enylidene)acetate, and hydrazone content. When (4-(benzyloxy)phenyl)hydrazine HPLC % area was <1, TFA (11.6 kg, 101.7 mol, 1.200 mole equiv., 0.550 mass equiv.) was charged over approximately 1 hour while the stirred reaction mixture was maintained at 60° C.±5° C. with reactor jacket cooling. As stirring at 60° C. to 65° C. was continued, the hydrazone and imine content of the reaction mixture was monitored by HPLC. After stirring at 60° C. to 65° C. for at least 12 hours the imine content of the reaction mixture was <5% area by HPLC, and the stirred reaction mixture was cooled to 20° C. to 25° C. over approximately 3 hours. Stirring was maintained at that temperature to allow isomerization of the Z isomer to the desired E isomer. The E isomer crystallizes from the reaction mixture. The Z isomer and E isomer % area content of the reaction mixture was monitored by HPLC during this period of stirring at 20° C. to 25° C., which was continued until the Z-isomer content of the reaction mixture was <15% area by HPLC.

The stirred reaction mixture was cooled (0° C. to 5° C.) over at least 2 hours and then filtered. The reactor was charged with ethanol (27.4 kg, 1.300 mass equiv.), which was stirred and chilled to 0° C. to 5° C. and then used in two approximately equal portions to slurry-wash the product filter cake twice. The reactor was charged with ethanol (13.8 kg, 0.655 mass equiv.), which was stirred and chilled to 0° C. to 5° C. and then used to wash the product filter cake by displacement. The reactor was charged with USP purified water (100 kg, 4.744 mass equiv.), and the temperature was adjusted to 20° C. to 25° C. The USP purified water was then used in three approximately equal portions to wash the product filter cake three times, the first two by reslurrying and the third by displacement. The reactor was charged with ethanol (16.4 kg, 0.778 mass equiv.), stirred and chilled to 0° C. to 5° C., and then used to wash the product filter cake by displacement. The washed product filter cake was dried under full vacuum first with a jacket temperature of 35° C. for 1 hour and then with a jacket temperature of 50° C. While drying continues with a jacket temperature of 50° C., the product solids are turned over every 1 hour to 3 hours, and product samples are analyzed for loss on drying (LOD) every ≥4 hours. When LOD was <1%, the product was cooled to <30° C. The yield of the title compound was 13.06 kg (37.59 mol, 44.7%).

Step E: Preparation of Ethyl 2-(7-Hydroxy-1,2,3,4-tetrahydrocyclopenta[b]indol-3-yl)acetate To a 200 liter Hastelloy reactor was added ethyl 2-(7-(benzyloxy)-1,2-dihydrocyclopenta[b]indol-3(4H)-ylidene) acetate (E/Z mixture, 12 kg), 10% Pd/C (50% wet with H$_2$O; 1.80 kg) and ethyl acetate (108 kg). The suspension was degassed 3× with N$_2$ and triethylamine (1.76 kg) was added. To the resulting mixture was added formic acid (3.34 kg) while maintaining the internal temperature at below 35° C. The reaction progression was followed by HPLC to monitor the complete consumption of starting material (i.e., E/Z mixture of ethyl 2-(7-(benzyloxy)-1,2-dihydrocyclopenta[b] indol-3(4H)-ylidene)acetate) and the debenzylated intermediate. After approximately 30 minutes an additional amount of formic acid (0.50 kg) was added and the combined peak area of ethyl 2-(7-(benzyloxy)-1,2-dihydrocyclopenta[b]indol-3(4H)-ylidene)acetate and the related debenzylated intermediate was determined to be <1% area by HPLC. The reactor contents were filtered through a 1.2 μm cartridge filter followed by an in-line 0.2 μm inline polishing filter. To the filtrate was added water (60 kg) and the biphasic mixture was partitioned. The organics were separated and concentrated under vacuum at approximately 60° C.±5° C. to a minimum stir volume, ethyl acetate (21.6 kg) was added and the mixture was further concentrated under vacuum to a minimum stir volume. Once again ethyl acetate (16.8 kg) was charged to the crude mixture and the resulting solution was heated to approximately 60° C. Heptanes (37.2 kg) were charged maintaining the internal temperature at 60° C. The solution was slowly cooled to approximately 0 to 5° C. and approximately 2-3 hr to facilitate crystallization. The slurry was filtered, the filter cake was reslurried in heptanes (27.12 kg) and ethyl acetate (7.08 kg). The resulting suspension was filtered, and the solids dried under vacuum at approximately 40±5° C. (until the loss on drying (LOD) is <1%) to afford the title compound (6.23 kg, 70.3% yield) as a solid.

Step F: Preparation of (R/S)-Ethyl 2-(7-(4-Cyclopentyl-3-(trifluoromethyl)benzyloxy)-1,2,3,4-tetrahydrocyclopenta[b]indol-3-yl)acetate To a 50 liter glass reactor containing ethyl 2-(7-hydroxy-1,2,3,4-tetrahydrocyclopenta[b]indol-3-yl)acetate (2.000 kg, 1.000 equiv.) was added cesium carbonate (3.266 kg, 1.300 equiv.) and acetonitrile (15.720 kg) under nitrogen. To the resulting mixture was added 4-(chloromethyl)-1-cyclopentyl-2-(trifluoromethyl)benzene (2.228 kg, 1.100 equiv.) over approximately one hour while maintaining the stirred reactor contents at 40° C.±5° C. After the addition of 4-(chloromethyl)-1-cyclopentyl-2-(trifluoromethyl)benzene the reactor contents were heated to 65° C.±5° C. with stirring until the concentration of ethyl 2-(7-hydroxy-1,2,3,4-tetrahydrocyclopenta[b]indol-3-yl)acetate in the reaction mixture was less than 2.0% area by HPLC. The reaction mixture was cooled to 50° C.±5° C. and filtered under nitrogen through a fine filter cloth with suction to remove cesium salts (Note: ethyl 2-(7-(4-cyclopentyl-3-(trifluoromethyl)benzyloxy)-1,2,3,4-tetrahydrocyclopenta[b]indol-3-yl)acetate may precipitate below 30° C.). The filter cake was washed with fresh hot (50° C.±5° C.) acetonitrile (5.658 kg divided in approximately three equal portions). The filtrates were returned to the reactor. The combined filtrates were concentrated by vacuum distillation with a jacket temperature of 60° C.±10° C. To the reactor was added ethyl alcohol (3.156 kg) and once again concentrated with stirring by vacuum distillation with a jacket temperature of 60° C.±10° C. Once again, ethyl alcohol (3.156 kg) was added to the reactor and the contents were concentrated by vacuum distillation with a jacket temperature of 60° C.±10° C. to a reactor volume of approximately 14 L. The stirred reactor contents were cooled to 0° C.±5° C. and the temperature maintained for 4 hours to facilitate the crystallization of the product. The resulting slurry was filtered. The filter cake was washed with cold 0° C.±5° C. ethyl alcohol (2×3.156 kg). The filter cake was dried under vacuum at 35° C.±5° C. until the weight loss over ≥1 hour was ≤2% to provide 3.0943 kg (81.0% yield) of the title compound as a solid.

Step G: Preparation of (R)-2-(7-(4-Cyclopentyl-3-(trifluoromethyl)benzyloxy)-1,2,3,4-tetrahydrocyclopenta[b]indol-3-yl)acetic Acid A 1.0 M buffer solution was prepared containing potassium phosphate monobasic (29.1 g, 0.0335 equiv.) in USP purified water (213 g) and potassium phosphate dibasic (368.2 g, 0.331 equiv.) in USP purified water (2.107 g). To a 50 liter glass reactor was added ethyl 2-(7-(4-cyclopentyl-3-(trifluoromethyl)benzyloxy)-1,2,3,4-tetrahydrocyclopenta[b]indol-3-yl)acetate (3.094 kg, 1.000 equiv.), Lipase B, Candida antarctica, immobilized (88.18 g, 293250 units/kg of ethyl ester starting material) and acetonitrile (22.32 kg). To the stirred contents of the reactor was added the previously prepared 1.0 M potassium phosphate buffer. The resulting mixture was stirred under nitrogen at a temperature of 40° C.±5° C. until the (R)-2-(7-(4-cyclopentyl-3-(trifluoromethyl)benzyloxy)-1,2,3,4-tetrahydrocyclopenta[b]indol-3-yl)acetic acid concentration was ≥35% area as determined by HPLC (Note: although the reaction usually is complete after about 10 hours, the reaction mixture may be held at 40° C.±5° C. overnight). The stirred reactor contents were cooled to 25° C.±5° C. and the pH was adjusted to between 4 and 5 by addition of a solution of citric acid (278.5 g, 0.228 equiv.) dissolved in USP purified water (1.454 kg). The reactor contents were filtered to remove immobilized lipase and phosphate and citrate salts. The reactor and solids were washed with acetonitrile (4.827 kg) and the combined filtrates were added backed into the reactor. The stirred reactor contents were concentrated to a volume of 1.0 L to 2.0 L by vacuum distillation at a jacket temperature of 55° C.±5° C. To the reactor was added ethyl acetate (5.582 kg) and USP purified water (6.188 kg). The contents were stirred at 20° C.±5° C. for at least 10 minutes and a solution of sodium chloride (1 kg) in USP purified water (1 kg) was added to facilitate phase separation. After phase separation was complete, the lower aqueous layer was drained. A solution of sodium chloride (5.569 kg) in USP purified water (12.38 kg) was divided in two approximately equal portions and the ethyl acetate phase was washed (2×). The ethyl acetate phase was transferred into a carboy and the reactor was rinsed with ethyl acetate (838.5 g) and added to the carboy containing the ethyl acetate phase. The reactor was washed sequentially with USP purified water (12.38 kg), acetone (4.907 kg), and ethyl acetate (838.5 g) and the ethyl acetate mixture from the carboy was transferred back to the reactor and concentrated with stirring to a volume of 1 L to 2 L by vacuum distillation at a jacket temperature of 55° C.±5° C. To the reactor was added 2-propanol (14.67 kg) and after stirring the resulting mixture was concentrated to a volume of 1 L to 2 L by vacuum distillation at a jacket temperature of 55° C.±5° C. To the reactor was added 2-propanol (7.333 kg) and heated with stirring at 60° C.±5° C. until the contents dissolved. The stirred reactor contents were cooled to 20° C.±5° C. and filtered through a medium-porosity fritted-glass filter to remove any inorganic solids to provide a 2-propanol solution containing 1.3188 kg of the title compound.

Step H: Preparation of Allyl (2S,3S,4S,5R)-6-(2-((R)-7-((4-Cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylate Allyl 3,4,5,6-tetrahydroxytetrahydro-2H-pyran-2-carboxylate (0.183 g, 0.783 mmol) and (R)-2-(7-(4-cyclopentyl-3-(trifluoromethyl)benzyloxy)-1,2,3,4-tetrahydrocyclopenta[b]indol-3-yl)acetic acid (0.358 g, 0.783 mmol) were weighed into an oven dried round bottomed flask equipped with septa and stir bar. MeCN (7.825 mL) was added, followed by 4-methylmorpholine (0.172 mL, 1.565 mmol) and Reactant 2 (0.298 g, 0.783 mmol). The solution took on a pale amber appearance. The reaction was stirred at rt under nitrogen for 3 h. LCMS complete. The reaction was concentrated to dryness and purified by column chromatography (silica gel, 5-10% EtOH in DCM) to afford 257 mg of the desired compound (clear, colorless film that eventually solidified upon standing). $^1$H NMR is consistent with the beta-isomer, LCMS m/z=674.4 [M+H]$^+$. The alpha-isomer is the less polar eluting reaction product.

Step I: Preparation of (2S,3S,4S,5R)-6-(2-((R)-7-((4-Cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic Acid (Compound 1)

Figure 2:
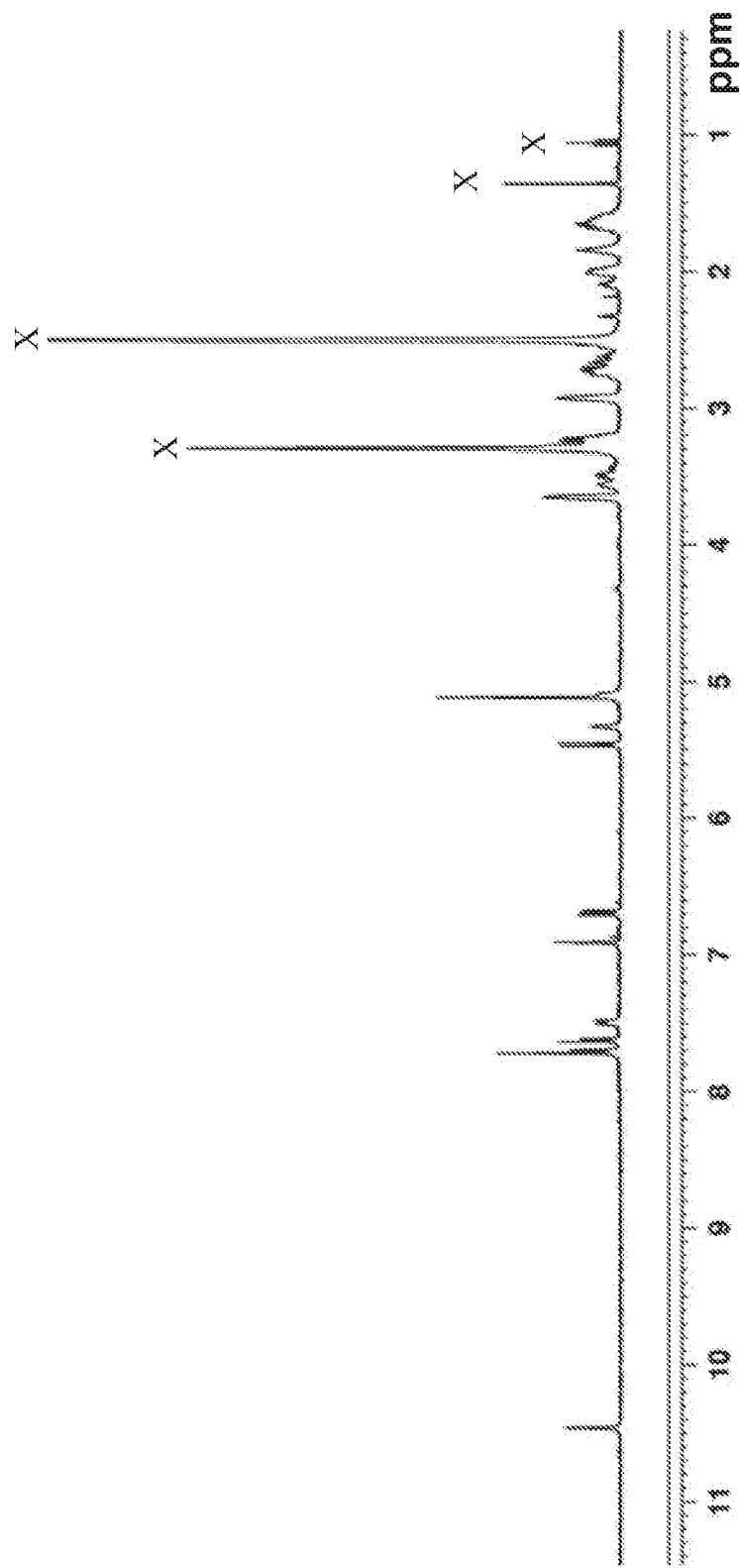
FIG. 2 shows a representative $^1$H NMR spectrum for Compound 1, where "X" refers to NMR solvent and/or residual solvent peaks.

Tetrakis(triphenylphosphine)palladium, polymer bound (1.0 g, Aldrich, Lot #0001371338, loading ~ 0.06 mmol/g) was stirred in THF (5 mL) for 16 h at room temperature. The THF was decanted off and morpholine (33.37 μL, 0.381 mmol) and a solution of allyl (2S,3S,4S,5R)-6-(2-((R)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylate (0.257 g, 0.381 mmol) in THF (5 mL) was added. The reaction was stirred at room temperature under nitrogen for 1 h. LCMS shows complete conversion to desired compound. The resin was removed by filtration and washed with THF, EtOAc, DCM, and DCM/EtOH (1:1 ratio). The washings were concentrated to a semi-solid and taken up in DCM and EtOH. Concentration of this mixture caused a precipitate to form (batch 1). The supernatant was removed and ppt 1 was dried under high vac to afford 49.6 mg of an off-white solid. The supernatant was further concentrated to afford a second batch (batch 2) which was recovered in the same manner to afford 16 mg of desired compound. Total amount of Compound 1 isolated was 65.6 mg. LCMS m/z=634.4 [M+H]$^+$; the $^1$H NMR can be found in FIG. 2.

Example 1.2: Preparation of 2-(7-((4-(3-Hydroxycyclopentyl)-3-(trifluoromethyl)benzyl)oxy)-1,2,3,4-tetrahydrocyclopenta[b]indol-3-yl)acetic Acid (Compounds 2-1 and Compounds 2-2)

Step A: Preparation of (4-Bromo-3-(trifluoromethyl)phenyl)methanol

To a solution of methyl 4-bromo-3-(trifluoromethyl)benzoate (10 g, 35.33 mmol) in THF (100 mL) under nitrogen was added 2 M lithium borohydride in THF (2.309 g, 106.0 mmol). The mixture was heated at reflux. The mixture was cooled to 0° C. and carefully quenched with 6 N HCl (aq) (about 20 mL or less) (vigorous in the beginning 3-5 mL) up to pH 3. The mixture was diluted with water (25 mL) and extracted with EtOAc (2×). The combined organics were dried over anhydrous Na$_2$SO$_4$ and filtered. The filtrate was concentrated in vacuo to dryness to afford the crude (4-bromo-3-(trifluoromethyl)phenyl)methanol as a brown solid.

Step B: Preparation of ((4-Bromo-3-(trifluoromethyl)benzyl)oxy)(tert-butyl)dimethylsilane To a solution of (4-bromo-3-(trifluoromethyl)phenyl) methanol (from Step A) in DCM (100.00 mL) under nitrogen was added 1H-imidazole (2.886 g, 42.40 mmol) and the mixture was cooled to 0° C. To this was added tert-butylchlorodimethylsilane (5.858 g, 38.86 mmol) and the mixture was stirred at RT for 2 hr. The reaction was not complete and thus more 1H-imidazole (2.886 g, 42.40 mmol) and tert-butylchlorodimethylsilane (5.858 g, 38.86 mmol) were added at 0° C. and the reaction was continued to stir at RT overnight. The mixture was quenched with water and the organic layer was separated. The organic layer was concentrated in vacuo to dryness and the residue was purified by silica gel column chromatography to afford ((4-bromo-3-(trifluoromethyl)benzyl)oxy)(tert-butyl)dimethylsilane (12.2359 g, 33.13 mmol, 93.8%) as a light yellow oil.

Step C: Preparation of 3-(4-(((tert-Butyldimethylsilyl)oxy)methyl)-2-(trifluoromethyl)phenyl)cyclopentanone To a solution of ((4-bromo-3-(trifluoromethyl)benzyl) oxy)(tert-butyl)dimethylsilane (1 g, 2.708 mmol) in THF (5 mL) at −78° C. under nitrogen was added isopropylmagnesium chloride (4.062 mL, 8.124 mmol). The mixture was stirred at RT overnight. To the resulting mixture was added copper(I) iodide (0.258 g, 1.354 mmol). After stirring at RT for 1 min, cyclopent-2-enone (0.272 mL, 3.249 mmol) was added. The mixture was stirred at RT for 10 min. The mixture was quenched with saturated NH$_4$Cl (aq) and extracted with EtOAc (2×). The combined organics were concentrated in vacuo to dryness and the residue was purified by silica gel column chromatography to afford 3-(4-(((tert-butyldimethylsilyl)oxy)methyl)-2-(trifluoromethyl)phenyl)cyclopentanone (0.4851 g, 1.302 mmol, 48.1%) as a faint yellow oil; LCMS m/z=282.4 [M+H]+.

Step D: Preparation of 3-(4-(Hydroxymethyl)-2-(trifluoromethyl)phenyl)cyclopentanone To a solution of 3-(4-(((tert-butyldimethylsilyl)oxy) methyl)-2-(trifluoromethyl)phenyl)cyclopentanone (0.4617 g, 1.239 mmol) in THF (5 mL) at RT under nitrogen was added 1 M tetrabutylammonium fluoride in THF (1.859 mL, 1.859 mmol). The mixture was stirred at RT for 30 min. The mixture was quenched with water and extracted with EtOAc (2×). The combined organics were concentrated in vacuo to dryness and the residue was purified by silica gel column chromatography to afford 3-(4-(hydroxymethyl)-2-(trifluoromethyl)phenyl)cyclopentanone (0.2894 g, 1.121 mmol, 90.4%) as an off-white oil.

Step E: Preparation of Ethyl 2-(7-((4-(3-Oxocyclopentyl)-3-(trifluoromethyl)benzyl)oxy)-1,2,3,4-tetrahydrocyclopenta[b]indol-3-yl)acetate Method A
To a solution of 3-(4-(hydroxymethyl)-2-(trifluoromethyl)phenyl)cyclopentanone (100 mg, 0.387 mmol), ethyl 2-(7-hydroxy-1,2,3,4-tetrahydrocyclopenta[b]indol-3-yl)acetate (0.100 g, 0.387 mmol), and triphenylphosphine (0.122 g, 0.465 mmol) in THF (5 mL) under nitrogen at 0° C. was added triethylamine (64.77 μl, 0.465 mmol), then followed by slow addition of (E)-diisopropyl diazene-1,2-dicarboxylate (91.76 μl, 0.465 mmol). The mixture was stirred at RT overnight (16 hr). The mixture was concentrated in vacuo to dryness and purified by prep HPLC. Pure fractions were combined, neutralized with saturated NaHCO$_3$ (aq), and concentrated in vacuo to remove MeCN. The aqueous residue was extracted with DCM (2×) and the combined organics were dried over anhydrous Na2SO4 and filtered. The filtrate was concentrated in vacuo to dryness to afford ethyl 2-(7-((4-(3-oxocyclopentyl)-3-(trifluoromethyl)benzyl)oxy)-1,2,3,4-tetrahydrocyclopenta[b]indol-3-yl)acetate (39 mg, 78.07 μmol, 20.2%) as a colorless gum; LCMS m/z=500.2 [M+H]+.

Method B
To a solution of 3-(4-(hydroxymethyl)-2-(trifluoromethyl)phenyl)cyclopentanone (134 mg, 0.519 mmol) in DCM (5 mL) under nitrogen at 0° C. was added N-ethyl-N-isopropylpropan-2-amine (0.108 mL, 0.623 mmol) and methanesulfonyl chloride (48.20 μl, 0.623 mmol). The mixture was stirred at 0° C. for 30 min. The reaction was quenched with water and the organic layer was separated and concentrated in vacuo to dryness. The residue was purified by silica gel column chromatography to afford 4-(3-oxocyclopentyl)-3-(trifluoromethyl)benzyl methanesulfonate (162.8 mg, 0.484 mmol, 93.3%) as an off-white oil.

To a mixture of 4-(3-oxocyclopentyl)-3-(trifluoromethyl) benzyl methanesulfonate (161.8 mg, 0.481 mmol), ethyl 2-(7-hydroxy-1,2,3,4-tetrahydrocyclopenta[b]indol-3-yl)acetate (0.187 g, 0.722 mmol), and cesium carbonate (0.313 g, 0.962 mmol) under nitrogen at RT was added DMF (5 mL). The mixture was stirred at RT overnight. The mixture was filtered and purified by prep HPLC. Pure fractions were combined, neutralized with saturated NaHCO$_3$ (aq), and concentrated in vacuo to remove MeCN. The aqueous residue was extracted with DCM (2×) and the combined organics were dried over anhydrous Na$_2$SO$_4$ and filtered. The filtrate was concentrated in vacuo to dryness to afford ethyl 2-(7-((4-(3-oxocyclopentyl)-3-(trifluoromethyl)benzyl)oxy)-1,2,3,4-tetrahydrocyclopenta[b]indol-3-yl)acetate (181.4 mg, 0.363 mmol, 75.5%) as an off-white gum; LCMS m/z=500.2 [M+H]+.

Step F: Preparation of Ethyl 2-(7-((4-(3-Hydroxycyclopentyl)-3-(trifluoromethyl)benzyl)oxy)-1,2,3,4-tetrahydrocyclopenta[b]indol-3-yl)acetate To a solution of ethyl 2-(7-((4-(3-oxocyclopentyl)-3-(trifluoromethyl)benzyl)oxy)-1,2,3,4-tetrahydrocyclopenta[b] indol-3-yl)acetate (250.5 mg, 0.501 mmol) in MeOH (50 mL) at 0° C. was added sodium borohydride (37.94 mg, 1.003 mmol). The mixture was stirred at 0° C. for 40 min. The mixture was quenched with saturated ammonium chloride (aq) (30 mL) and extracted with DCM (2×). The combined organics were concentrated in vacuo and purified by silica gel column chromatography to afford ethyl 2-(7-((4-(3-hydroxycyclopentyl)-3-(trifluoromethyl)benzyl) oxy)-1,2,3,4-tetrahydrocyclopenta[b]indol-3-yl)acetate (224.7 mg, 0.448 mmol, 89.3%) as an off-white gum; LCMS m/z=502.2 [M+H]+.

Step G: Preparation of 2-(7-((4-(3-Hydroxycyclopentyl)-3-(trifluoromethyl)benzyl)oxy)-1,2,3,4-tetrahydrocyclopenta[b]indol-3-yl)acetic Acid (Compounds 2-1 and Compounds 2-2)

To a solution of ethyl 2-(7-((4-(3-hydroxycyclopentyl)-3-(trifluoromethyl)benzyl)oxy)-1,2,3,4-tetrahydrocyclopenta[b]indol-3-yl)acetate (222.4 mg, 0.443 mmol) in a mixed solvent of MeOH (9 mL), THF (3.0 mL), and H$_2$O (3.0 mL) at RT was added lithium hydroxide hydrate (65.13 mg, 1.552 mmol). The mixture was stirred at RT over the weekend. The mixture was quenched with 1 M citric acid (1.6 mL), diluted with brine, and extracted with EtOAc (1×). The organic layer was concentrated in vacuo to dryness. The residue was purified by prep HPLC to provide two sets of isomers (Set 1: Fractions 4 & 5; and Set 2: Fractions 7 & 8). Each fraction was lyophilized separately.

Figure 4:
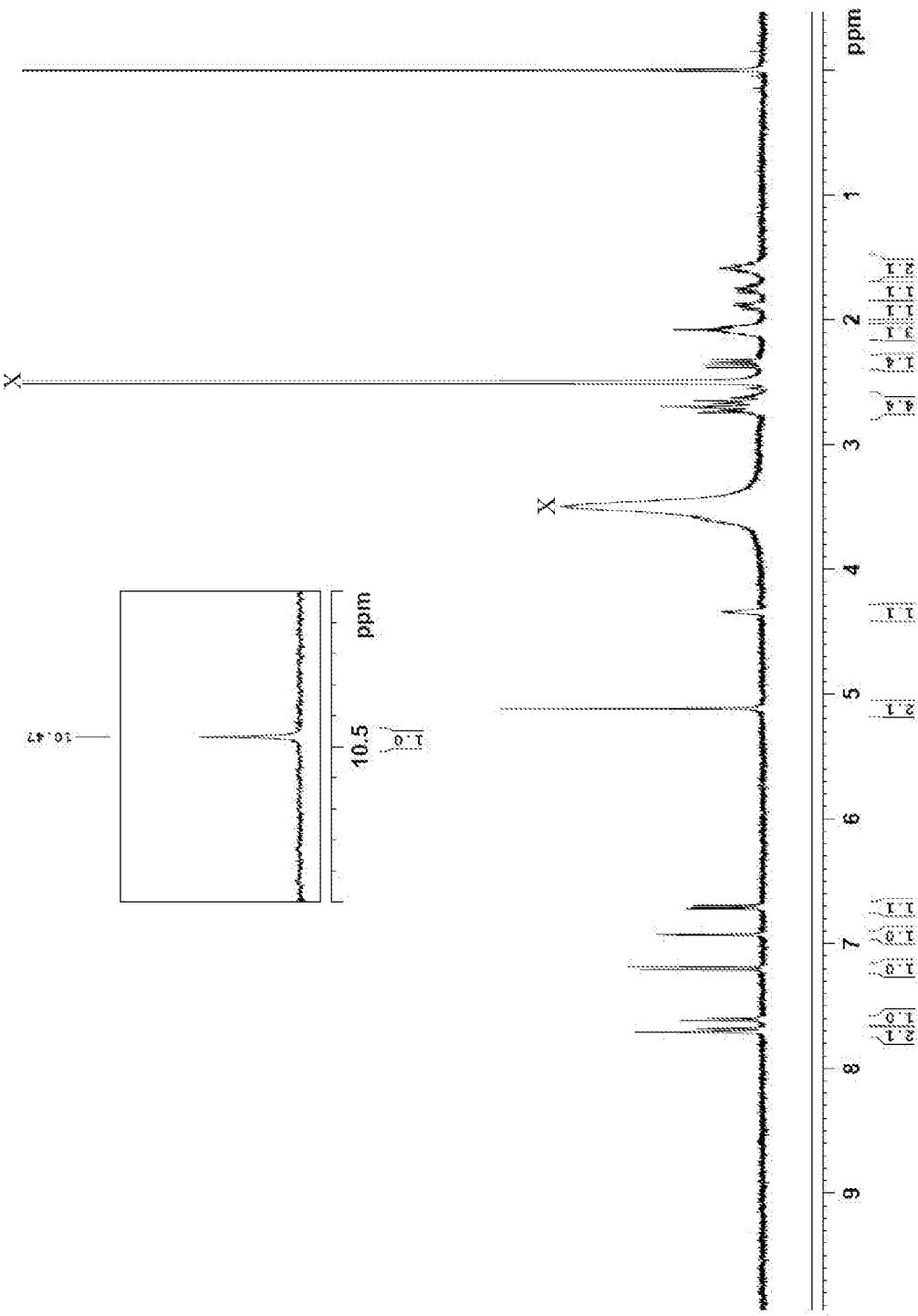
FIG. 4 shows a representative $^1$H NMR spectrum for Compound 2-1, where "X" refers to NMR solvent and/or residual solvent peaks. See Example 1.2, Step G (Fractions 4 and 5) for details.

Fraction 4 (34.3 mg) and Fraction 5 (51.1 mg), each showed similar NMR spectrum (Compound 2-1; 85.4 mg, 0.180 mmol, 40.7%); the EC$_{50}$ was determined (see Example 2)); LCMS m/z=474.2 [M+H]+; the $^1$H NMR can be found in FIG. 4.

Figure 5:
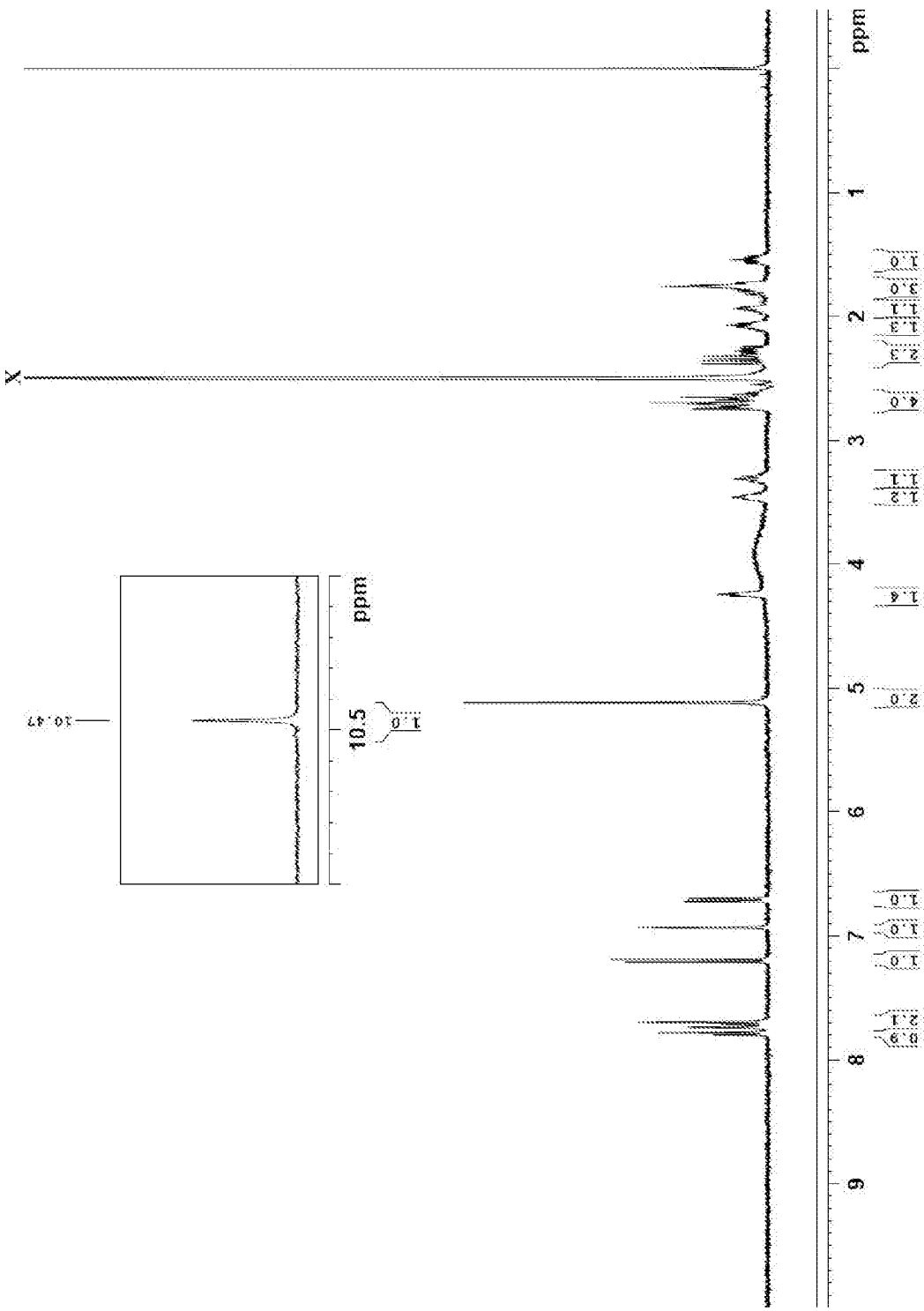
FIG. 5 shows a representative $^1$H NMR spectrum for Compound 2-2, where "X" refers to NMR solvent and/or residual solvent peaks. See Example 1.2, Step G (Fractions 7 and 8) for details.

Fraction 7 (68.6 mg) and Fraction 8 (9.4 mg), each showed similar NMR spectrum (Compound 2-2, 78 mg, 0.165 mmol, 37.1%, the EC$_{50}$ was determined (see Example 2)); LCMS m/z=474.2 [M+H]+; the $^1$H NMR can be found in FIG. 5.

Example 1.3: Preparation of 2-(7-((4-(3-Oxocyclopentyl)-3-(trifluoromethyl)benzyl)oxy)-1,2,3,4-tetrahydrocyclopenta[b]indol-3-yl)acetic Acid (Compound 3)

Figure 6:
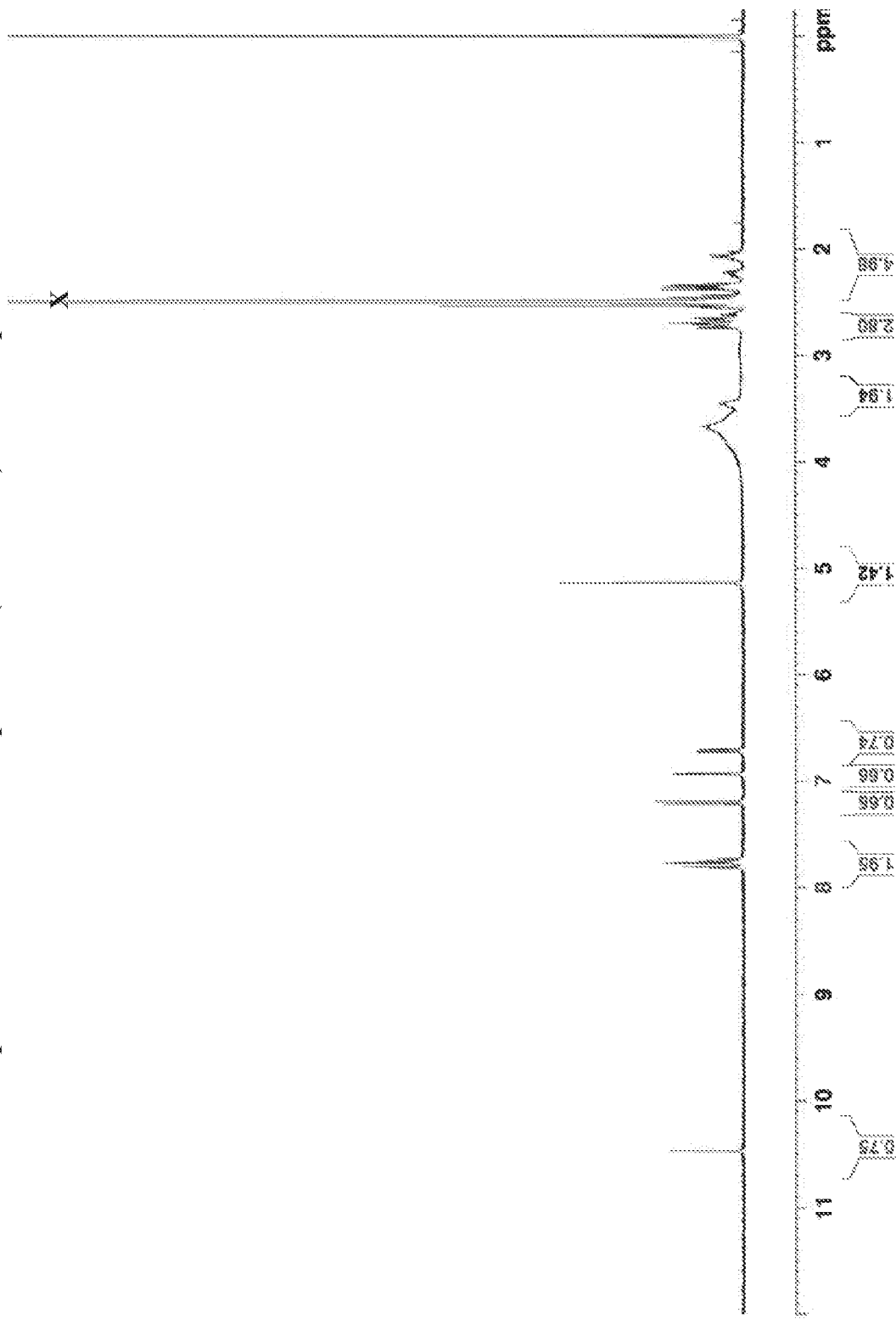
FIG. 6 shows a representative $^1$H NMR spectrum for Compound 3, where "X" refers to NMR solvent and/or residual solvent peaks. See Example 1.3 for details.

To a 50 mL round bottom flask were added ethyl 2-(7-((4-(3-oxocyclopentyl)-3-(trifluoromethyl)benzyl)oxy)-1,2,3,4-tetrahydrocyclopenta[b]indol-3-yl)acetate (0.120 g, 0.240 mmol, prepared in a similar as described above in Example 1.2, Step E, Method B), MeOH (10 mL), and H$_2$O (1 mL) under N$_2$ at room temperature. To the mixture was added lithium hydroxide (0.161 g, 6.726 mmol) and stirred overnight. An aliquot was sampled for LC/MS and the mixture was concentrated to almost dryness. To the resulting mixture was added charged H$_2$O (10 mL) and acidified with 2 N HCl (3.25 mL, ~ pH=2-3). The slurry was filtered, and the filter cake was washed with H$_2$O (5 mL). The filter cake was collected and dried under vacuum at 45° C. overnight. The crude product was purified by HPLC (20-95% MeCN/water, 0.1% TFA) to provide the title compound over six fractions. The fractions were frozen and lyophilized to provide the title compound (27.9 mg). LCMS m/z=472.6 [M+H]$^+$; the $^1$H NMR can be found in FIG. 6.

Example 1.4: Preparation of 2-(7-((4-(2-Hydroxycyclopentyl)-3-(trifluoromethyl)benzyl)oxy)-1,2,3,4-tetrahydrocyclopenta[b]indol-3-yl)acetic Acid (Compound 4)

Step A: Preparation of ((4-Bromo-3-(trifluoromethyl)benzyl)oxy)(tert-butyl) dimethylsilane To a mixture of (4-bromo-3-(trifluoromethyl)phenyl)methanol (7.969 g, 31.25 mmol) and 1H-imidazole (2.553 g, 37.50 mmol) in dichloromethane (DCM, 39.9 mL, 31.25 mmol) at RT under nitrogen was added tert-butylchlorodimethylsilane (5.181 g, 34.37 mmol). The resulting mixture was stirred for 1 h and quenched with sat. aq. NaHCO$_3$ (20 mL) added drop wise (pH 7). The layers were separated, and the aqueous layer extracted with DCM (2×10 mL). The DCM layers were combined, dried over Na$_2$SO$_4$, filtered, and concentrated. The resulting liquid was dried under vacuum at rt overnight to give a light orange liquid (11.74 g); $^1$H NMR (CDCl$_3$) δ ppm 1.11 (s, 6H), 0.95 (s, 9H), 4.72 (s, 2H), 7.34 (bd, 1H), 7.64-7.68 (m, 2H).

Step B: Preparation of 2-(4-(((tert-Butyldimethylsilyl)oxy)methyl)-2-(trifluoromethyl)phenyl)cyclopentanol To a solution of ((4-bromo-3-(trifluoromethyl)benzyl)oxy)(tert-butyl)dimethylsilane (5.637 g, 15.26 mmol) in tetrahydrofuran (50 mL, 15.26 mmol) in a 100 mL round bottom flask at −78° C. under N$_2$ was added isopropylmagnesium chloride (7.632 mL, 15.26 mmol) dropwise. The cold bath was removed, and the resulting mixture stirred at rt for 1 h. To the mixture was sequentially added copper(I) iodide (0.291 g, 1.526 mmol) followed by 6-oxabicyclo[3.1.0]hexane (2.645 mL, 30.53 mmol). The mixture was maintained with stirring under nitrogen at RT overnight. To the mixture was added copper(I) iodide (0.291 g, 1.526 mmol) and 6-oxabicyclo[3.1.0]hexane (1.322 mL, 15.26 mmol) at rt and maintained for ~4 h.

The mixture was quenched with sat NH$_4$Cl (11.5 mL) to give a brown suspension. EtOAc (28 mL) and water (5 mL) were added and the resulting layers were separated. The aqueous layer was extracted with EtOAc (2×28 mL). The organics were combined, dried over Na$_2$SO$_4$, filtered, and concentrated under vacuum. The resulting liquid was dried at RT under high vacuum to give a liquid. The liquid was purified (silica gel, hexanes/EtOAc) to give an orange oil (4.019 g).

Step C: Preparation of 2-(4-(((tert-Butyldimethylsilyl)oxy)methyl)-2-(trifluoromethyl)phenyl)cyclopentanone To a 500 mL round bottom flask was added 2-(4-(((tert-butyldimethylsilyl)oxy)methyl)-2-(trifluoromethyl)phenyl) cyclopentanol (3.745 g, 10.000 mmol), Dess-Martin periodinane (6.357 g, 14.99 mmol) and dichloromethane (61 mL). To the stirred mixture was added slowly at rt over 50 minutes a mixture of water (0.198 mL, 10.99 mmol) in dichloromethane (198 mL). The resulting suspension was diluted with MTBE (100 mL) and concentrated to give a wet white residue. To the residue was added MTBE (600 mL) and washed sequentially with 10% NaS$_2$O$_3$/saturated aqueous NaHCO$_3$ (1:1, 300 mL), H$_2$O (300 mL), and brine (300 mL). The resulting organic layer was dried over anhydr. Na$_2$SO$_4$, filtered, and evaporated. The resulting oil was dried under high vacuum at RT to give an orange thick oil (3.71 g).

Step D: Preparation of 2-(4-(Hydroxymethyl)-2-(trifluoromethyl)phenyl)cyclo-pentanone To a solution of 2-(4-(((tert-butyldimethylsilyl)oxy)methyl)-2-(trifluoromethyl)phenyl) cyclopentanone (3.570 g, 9.584 mmol) in tetrahydrofuran (THF, 36 mL, 9.584 mmol) in a 200 mL round bottom flask under nitrogen was added tetrabutylammonium fluoride in THF (14.38 mL, 14.38 mmol). The resulting solution was stirred for 30 min. The resulting mixture was quenched with water (5 mL) and concentrated to give a dark orange solution ~10 mL. The solution was diluted with EtOAc (200 mL) and water (50 mL), and the layers were separated. The aqueous layer was extracted with EtOAc (2×100 mL) and the organics combined. The organics were washed with brine (2×200 mL), dried over $Na_2SO_4$, and filtered. The solution was concentrated and dried under high vacuum to give a liquid (3.91 g). The resulting orange liquid was purified using a Biotage system (silica gel, hexanes/EtOAc). The purified fractions were combined, concentrated, and dried under high vacuum to give a light orange, thick oil (2.07 g); $^1$H NMR ($CD_2Cl_2$) δ ppm 1.90-2.04 (m, 2H), 2.12-2.22 (m, 1H), 2.26-2.37 (m, 1H), 2.46-2.60 (m, 2H), 3.65 (dd, $J_1$=11.0, $J_2$=8.0, 1H), 4.71 (s, 2H), 7.12 (brd, J=8.0, 1H), 7.53 (brd, J=8.0, 1H), 7.66 (brs, 1H).

Step E: Preparation of 4-(2-Oxocyclopentyl)-3-(trifluoromethyl)benzyl methanesulfonate To a solution of 2-(4-(hydroxymethyl)-2-(trifluoromethyl)phenyl)cyclopentanone (1.000 g, 3.872 mmol) and N-ethyl-N-isopropylpropan-2-amine (0.809 mL, 4.647 mmol) in dichloromethane (20 mL, 3.872 mmol) at 0° C. under nitrogen was slowly added methanesulfonyl chloride (0.360 mL, 4.647 mmol). An internal temperature of approximately 0° C. to 1.5° C. was maintained during the addition (~20 minutes). The mixture was stirred at 0° C. for 1 h and quenched with $H_2O$ (4 mL) while maintaining the internal temperature at approximately 0° C. The layers were separated and the aqueous layer and extracted with EtOAc (2×5 mL). The organics were combined, washed with saturated NaCl solution (2×15 mL), and dried over $Na_2SO_4$ over night. The mixture was filtered, concentrated, and dried under vacuum to give a brown residue (1.26 g); $^1$H NMR ($CD_2Cl_2$) δ ppm 1.95-2.05 (m, 2H), 2.15-2.25 (m, 1H), 2.26-2.38 (m, 1H), 2.46-2.62 (m, 2H), 3.00 (s, 3H) 3.66-3.73 (brdd, 1H), 5.24 (s, 2H), 7.20 (d, J=8.0, 1H), 7.60 (dd, $J_1$=8.0, $J_2$=2.0, 1H), 7.71 (d, J=2.0, 1H).

Step F: Preparation of Ethyl 2-(7-((4-(2-Oxocyclopentyl)-3-(trifluoromethyl)benzyl)oxy)-1,2,3,4-tetrahydrocyclopenta[b]indol-3-yl)acetate To a solution of ethyl 2-(7-hydroxy-1,2,3,4-tetrahydrocyclopenta[b]indol-3-yl)acetate (0.705 g, 2.721 mmol) and cesium carbonate (1.182 g, 3.627 mmol) in acetonitrile (ACN, 27 mL) in a 100 mL round bottom flask under nitrogen at RT was added dropwise a solution of 4-(2-oxocyclopentyl)-3-(trifluoromethyl)benzyl methanesulfonate (0.610 g, 1.814 mmol) in acetonitrile (12 mL). The mixture was stirred at RT for 1 h. The resulting mixture was filtered through a pad of celite under nitrogen. The celite pad was washed with ACN (3×20 mL) and the pH of the organics was adjusted to pH 6-7 with 1N HCl (700 μl). The mixture was concentrated and dried under vacuum at rt overnight. The mixture was purified by prep HPLC and the fractions were lyophilized to give the title compound as an orange red solid (227.0 mg); LCMS m/z=500.4 [M+H]+.

Step G: Preparation of Ethyl 2-(7-((4-(2-Hydroxycyclopentyl)-3-(trifluoromethyl)benzyl)oxy)-1,2,3,4-tetrahydrocyclopenta[b]indol-3-yl)acetate To a solution of ethyl 2-(7-((4-(2-oxocyclopentyl)-3-(trifluoromethyl)benzyl)oxy)-1,2,3,4-tetrahydrocyclopenta[b]indol-3-yl)acetate (0.227 g, 0.454 mmol) in methanol (45 mL, 0.454 mmol) at 0° C. was added sodium borohydride (34.38 mg, 0.909 mmol). After 40 min at 0° C. the mixture was quenched with saturated ammonium chloride (40 mL), followed by water (10 mL), and concentrated. The resulting aqueous mixture (~50 mL) was extracted with EtOAc (3×50 mL), the combined organics dried (anhydrous $Na_2SO_4$), filtered, and concentrated under vacuum. The resulting residue was further dried under vacuum overnight and purified by prep HPLC to provide two sets of diastereomers. The pure fractions were combined and lyophilized to provide an orange fluffy powder (102 mg, major diastereomers; LCMS m/z=502.2 [M+H]+) and an orange fluffy powder (60 mg, minor diastereomers; LCMS m/z=502.6 [M+H]+).

Step H: Preparation of 2-(7-((4-(2-Hydroxycyclopentyl)-3-(trifluoromethyl)benzyl)oxy)-1,2,3,4-tetrahydrocyclopenta[b]indol-3-yl)acetic Acid (Compound 4-1)

Figure 7:
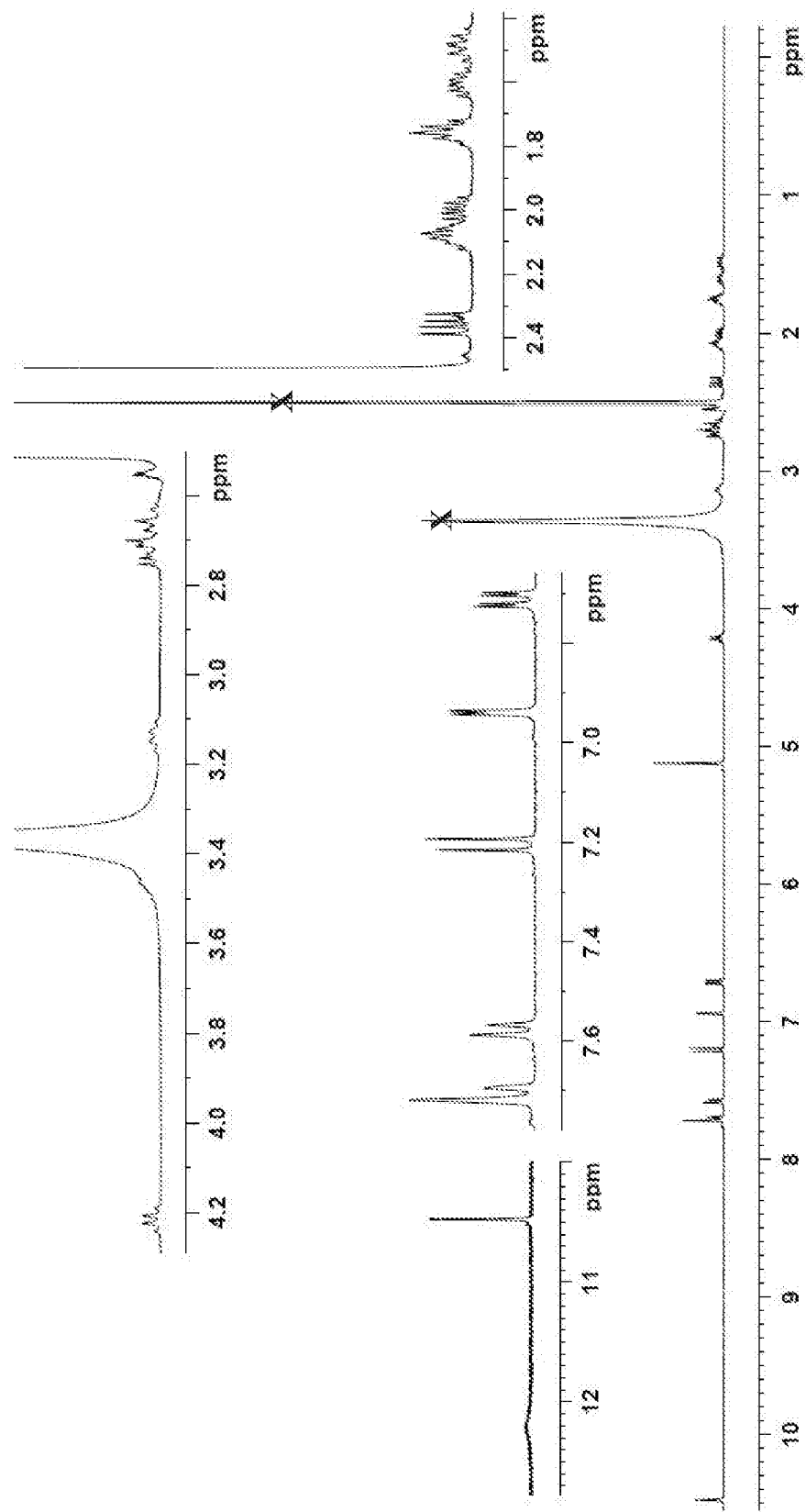
FIG. 7 shows a representative $^1$H NMR spectrum for Compound 4-1, where "X" refers to NMR solvent and/or residual solvent peaks. See Example 1.4, Step H for details.

To a solution of ethyl 2-(7-((4-(2-hydroxycyclopentyl)-3-(trifluoromethyl)benzyl)oxy)-1,2,3,4-tetrahydrocyclopenta[b]indol-3-yl)acetate (0.100 g, 0.199 mmol, major diastereomers from Step G) in tetrahydrofuran (3.5 mL) and water (3.5 mL) in a 20 mL scintillation vial under nitrogen at RT was added lithium hydroxide hydrate (29.28 mg, 0.698 mmol). The resulting mixture was allowed to stir at RT for about 5.5 h, quenched with HCl (1.0 N, 0.72 mL) to adjust pH 3 to 4, and concentrated under vacuum to remove most of the THF. The aqueous mixture was extracted with EtOAc (3×10 mL), the combined organics were dried over anhydrous $Na_2SO_4$, filtered. The resulting solution was filtered and dried under vacuum overnight. The residue was purified by semi-prep HPLC and the fractions with the expected [M+H]$^+$ were lyophilized. The fractions were combined to provide the title compound as a solid; 67.6. mg, Compound 4-1 (diastereomers); LCMS m/z=474.4 [M+H]$^+$; the $^1$H NMR can be found in FIG. 7.

Step I: Preparation of 2-(7-((4-(2-Hydroxycyclopentyl)-3-(trifluoromethyl)benzyl)oxy)-1,2,3,4-tetrahydrocyclopenta[b]indol-3-yl)acetic Acid (Compound 4-2)

Figure 8:
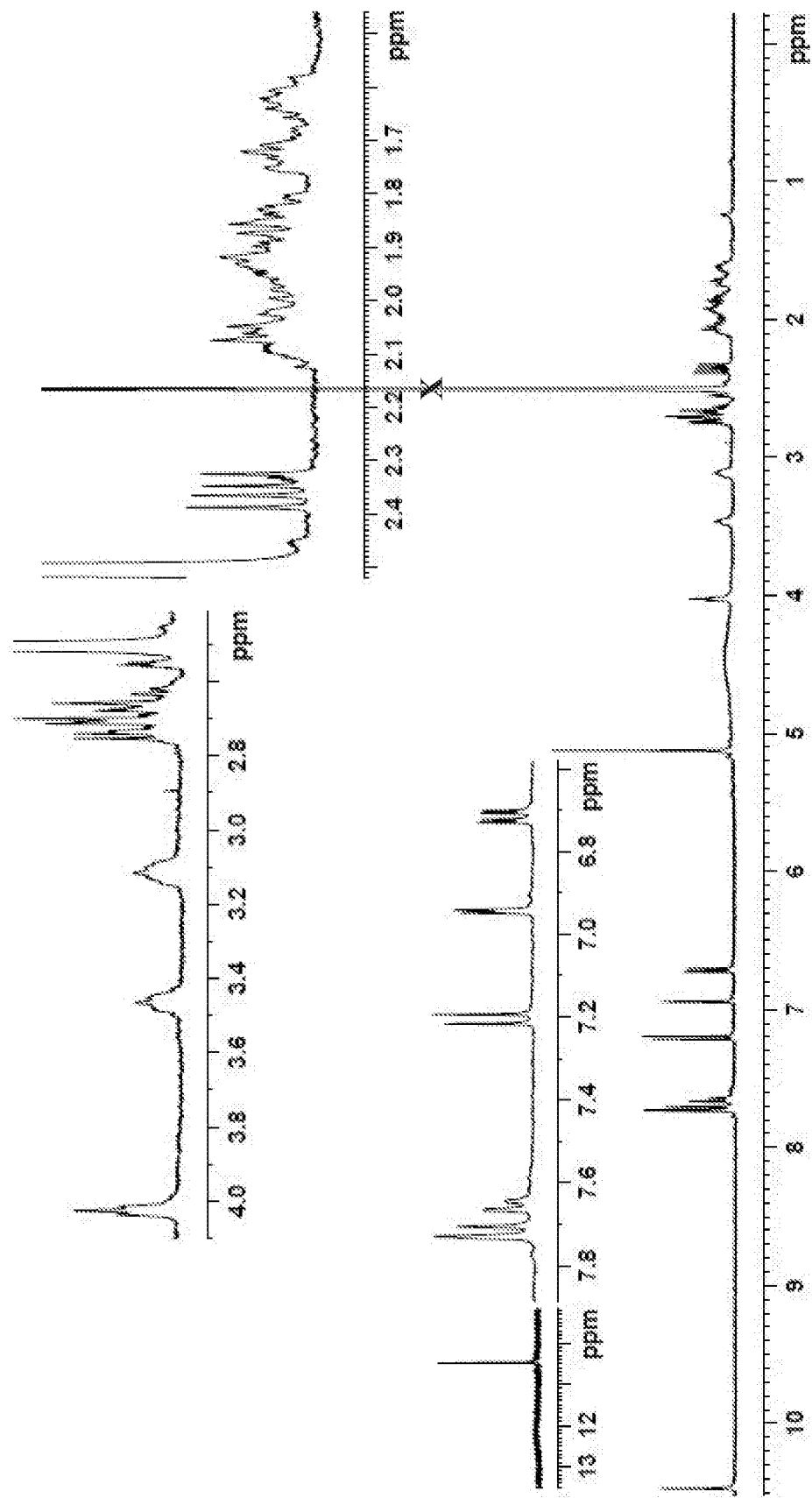
FIG. 8 shows a representative $^1$H NMR spectrum for Compound 4-2, where "X" refers to NMR solvent and/or residual solvent peaks. See Example 1.4, Step I for details.

To a solution of ethyl 2-(7-((4-(2-hydroxycyclopentyl)-3-(trifluoromethyl)benzyl)oxy)-1,2,3,4-tetrahydrocyclopenta[b]indol-3-yl)acetate (0.060 mg, 0.120 mmol, minor diastereomers from Step G) in tetrahydrofuran (2.1 mL) and water (2.1 mL) in a 20 mL scintillation vial under nitrogen at RT was added lithium hydroxide hydrate (17.57 mg, 0.419 mmol). The resulting mixture was allowed to stir at RT for about 3 h, quenched with HCl (1.0 N, 0.42 mL) to adjust pH 3 to 4, and concentrated under vacuum to remove most of the THF. The aqueous mixture was extracted with EtOAc (3×10 mL), the combined organics were dried over anhydrous $Na_2SO_4$, filtered. The resulting solution was filtered and dried under vacuum overnight. The residue was purified by semi-prep HPLC and the fractions with the expected [M+H]$^+$ were lyophilized. The fractions were combined to provide the title compound as a solid; 34.9 mg, Compound 4-2 (diastereomers); LCMS m/z=474.4 [M+H]$^+$; the $^1$H NMR can be found in FIG. 8.

Example 1.5: Preparation of 2-(7-((4-Isopropoxy-3-(trifluoromethyl)benzyl)oxy)-1,2,3,4-tetrahydrocyclopenta[b]indol-3-yl)acetic acid (Compound 6)

Step A: Preparation of Isopropyl 4-isopropoxy-3-(trifluoromethyl)benzoate

To a mixture of 4-hydroxy-3-(trifluoromethyl)benzoic acid (14.55 mmol) and cesium carbonate (43.7 mmol) in DMA (60 mL) was added 2-bromopropane (36.4 mmol). The reaction was stirred at 80° C. for 16 h. The mixture was filtered through celite and concentrated under vacuum. The residue was dissolved in EtOAc and washed with water, then brine, then dried over MgSO$_4$, and filtered. The solvent was removed under vacuum to give the title compound as a light yellow oil (13.1 mmol). $^1$H NMR (400 MHz, CDCl$_3$) δ ppm 1.36 (d, J=6.32 Hz, 6H), 1.39 (d, J=6.06 Hz, 6H), 4.72 (septet, J=6.06 Hz, 1H), 5.24 (septet, J=6.25 Hz, 1H), 7.00 (d, J=8.84 Hz, 1H), 7.26 (s, OH), 8.15 (dd, J=8.72, 2.15 Hz, 1H), 8.23 (d, J=2.15 Hz, 1H).

Step B: Preparation of (4-Isopropoxy-3-(trifluoromethyl)phenyl)methanol

To a cooled (−78° C.) solution of 4-isopropoxy-3-(trifluoromethyl)benzoate (13.1 mmol) in DCM (85 mL) under nitrogen was added 2.0 M solution of LAH (19.0 mmol) by a syringe. The reaction was allowed to return to room temperature and stirred for 16 h. The reaction was cooled to 0° C. and quenched with water (0.95 mL) and 10% NaOH (aq) (1.90 mL). The mixture was filtered through Celite®. The filtrate was concentrated under vacuum to give the title compound as an oil (11.27 mmol). $^1$H NMR (400 MHz, DMSO-d$_6$) δ ppm 1.27 (d, J=6.06 Hz, 6H), 4.46 (d, J=5.81 Hz, 2H), 4.75 (septet, J=6.02 Hz, 1H), 5.20 (t, J=5.75 Hz, 1H), 7.23 (d, J=8.46 Hz, 1H), 7.47-7.56 (m, 2H).

Step C: Preparation of 4-(Chloromethyl)-1-isopropoxy-2-(trifluoromethyl)benzene

To a solution of (4-isopropoxy-3-(trifluoromethyl)phenyl)methanol (11.27 mmol) in toluene (20 mL) was added thionyl chloride (67.7 mmol). The reaction was stirred at 75° C. for 3 h. The mixture was diluted with hexanes, washed with water (twice), saturated NaHCO$_3$, dried over MgSO$_4$, and filtered. The solvent was removed under vacuum to give the title compound as an oil (10.4 mmol). $^1$H NMR (400 MHz, DMSO-d$_6$) δ ppm 1.29 (d, J=6.06 Hz, 6H), 4.75-4.85 (m, 3H), 7.30 (d, J=8.46 Hz, 1H), 7.63-7.70 (m, 2H).

Step D: Preparation of 2-(7-((4-Isopropoxy-3-(trifluoromethyl)benzyl)oxy)-1,2,3,4-tetrahydrocyclopenta[b]indol-3-yl)acetic acid (Compound 6)

Figure 9:
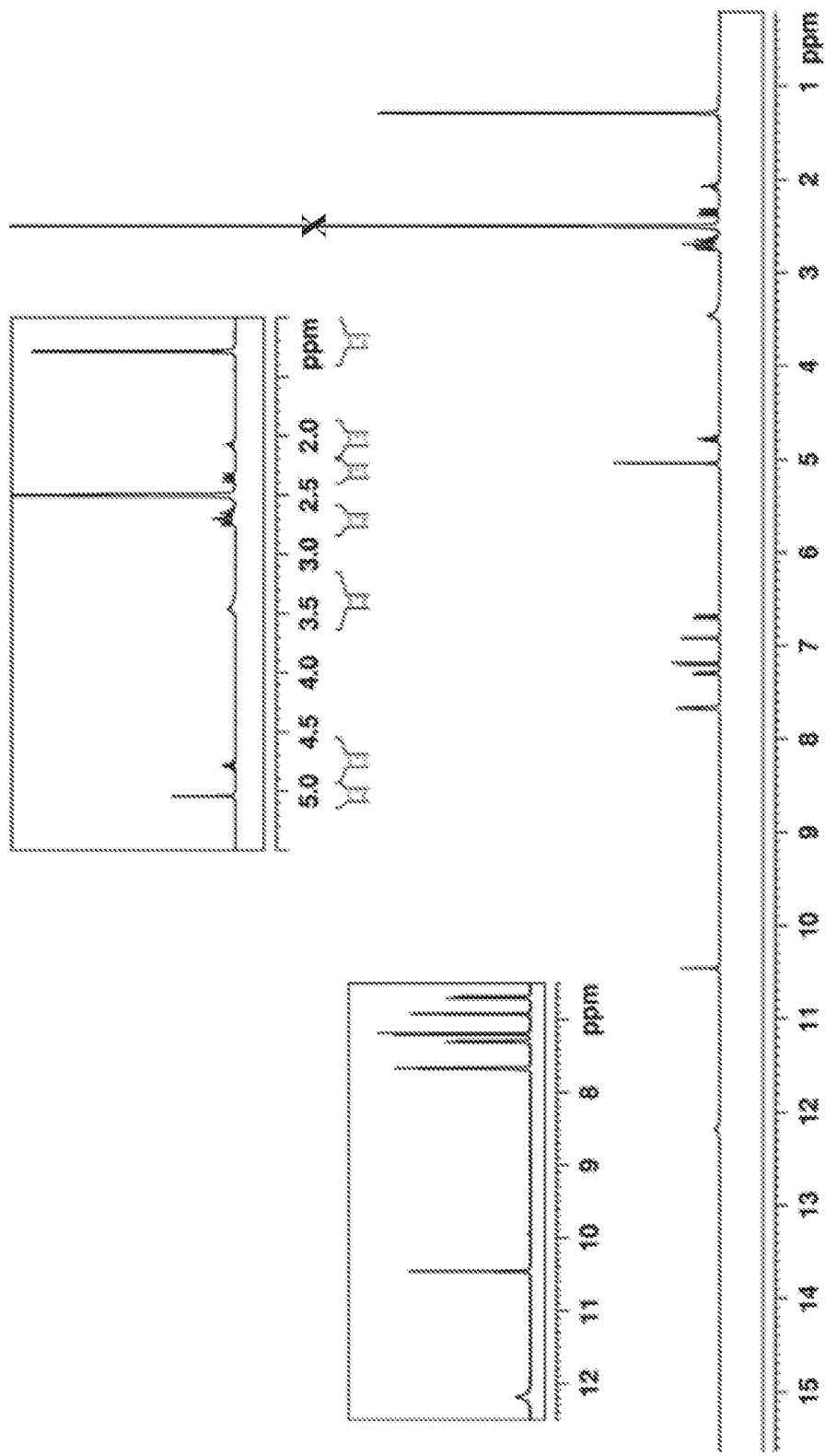
FIG. 9 shows a representative $^1$H NMR spectrum for Compound 6, where "X" refers to NMR solvent and/or residual solvent peaks. See Example 1.5, Step D for details.

To a solution of ethyl 2-(7-hydroxy-1,2,3,4-tetrahydrocyclopenta[b]indol-3-yl)acetate (0.2 g, 0.771 mmol, see WO2010/011316) and DMA (2 ml) was added cesium carbonate (0.302 g, 0.926 mmol) and 4-(chloromethyl)-1-isopropoxy-2-(trifluoromethyl)benzene (0.214 g, 0.848 mmol). The mixture was stirred for 24 h at rt and then diluted with water causing a precipitate to form. The DMA/water was decanted off and the remaining solids were taken up in dioxane (6 mL) and 1M aq. LiOH (2.0 mL) was added. The reaction was stirred for 24 h at rt and then acidified with 0.5M aq. citric acid. The crude product was extracted twice with EtOAc, and the combined extracts were dried with sodium sulfate, filtered, and concentrated. The concentrate was recrystallized from EtOAc/hexanes. The solids were filtered and dried to give the Compound 6 (0.345 g); LCMS m/z=448.3 [M+H]*; the $^1$H NMR can be found in FIG. 9.

Example 2: Beta Arrestin Assay

The in vitro S1P1 activity was determined in the beta arrestin assay. The EC$_{50}$ values for certain compounds of the present invention are shown in the table below.

| Compound No. | EC$_{50}$ S1P1 (beta-arrestin) |
|---|---|
| 1 [A] | 3.9 nM (n = 3) |
| 2-1 | 52.1 nM (n = 7) |
| 2-2 | 85.6 nM (n = 7) |
| 4 [B] | 3.66 nM (n = 7) |
| 4-1 | 16.7 nM (n = 7) |

Figure 3:
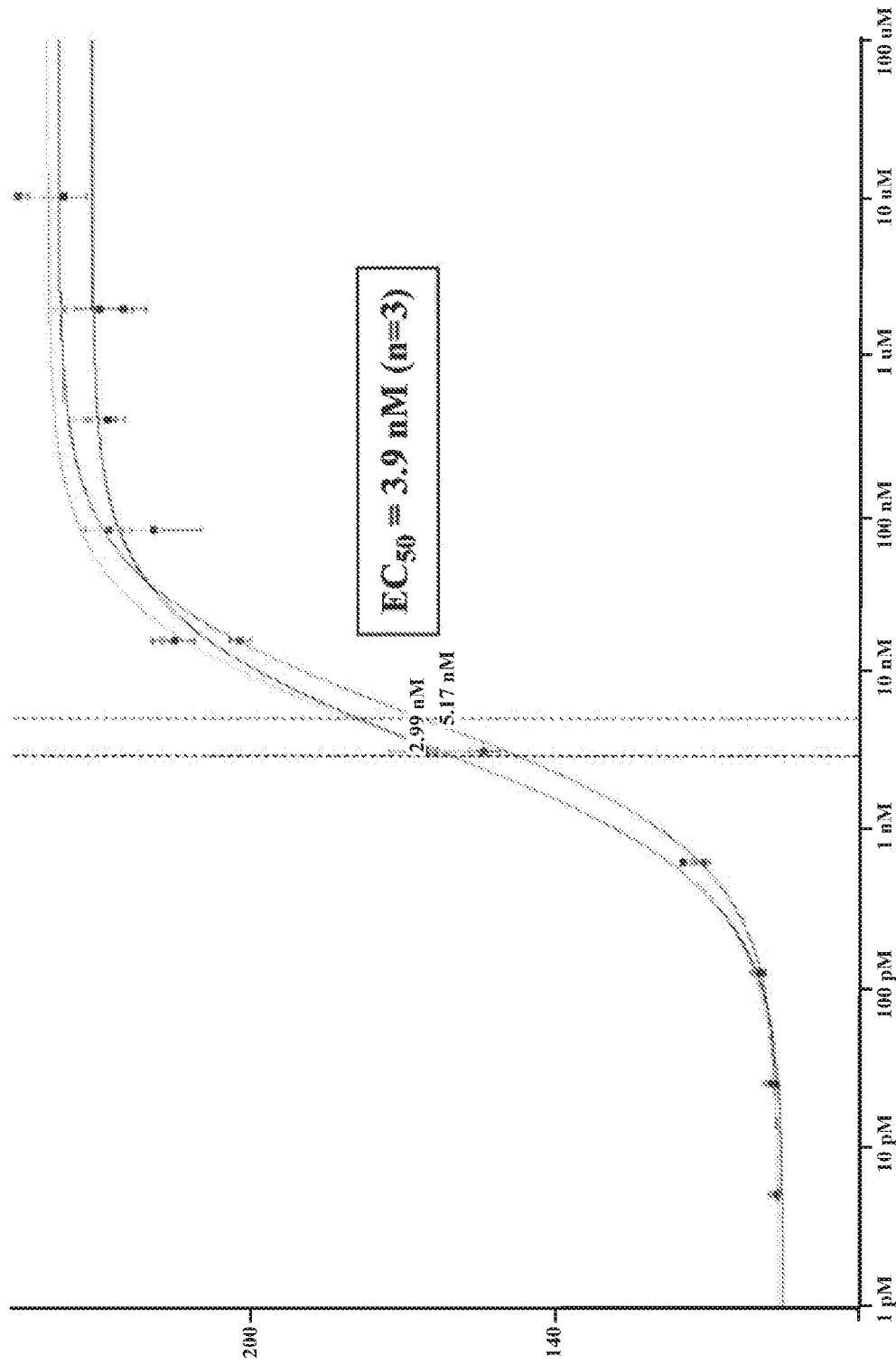
FIG. 3 shows representative in vitro beta-arrestin agonist assay curves (n=3) for Compound 1.

[A] The assay curves of Compound 1 are shown in FIG. 3.
[B] Compound 4 is a mixture of all stereoisomers.

Those skilled in the art will recognize that various modifications, additions, substitutions and variations to the illustrative examples set forth herein can be made without departing from the spirit of the invention and are, therefore, considered within the scope of the invention. All documents referenced above, including, but not limited to, printed publications and provisional and regular patent applications, are incorporated herein by reference in their entirety.

What is claimed is:

1. A compound selected from the compounds of Formula (Ia) and pharmaceutically acceptable salts, solvates, and hydrates thereof:

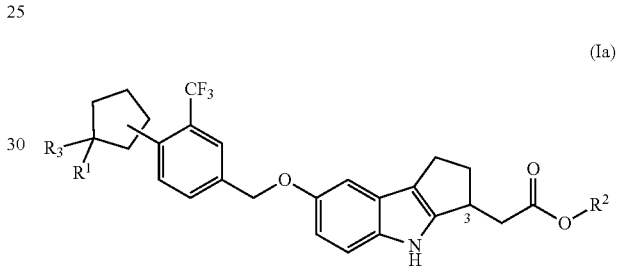

(Ia)

wherein:

R$^1$ is H or OH;

R$^3$ is H; or

R$^1$ and R$^3$ together form an oxo group;

and

R$^2$ is H or the group of Formula (IIa):

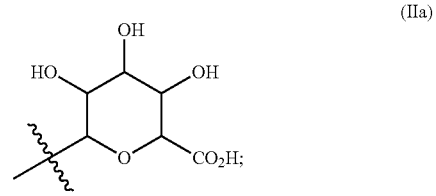 [SMILES: *C1OC(C(=O)O)C(O)C(O)C1O]

(IIa)

provided that if R$^2$ is H, then R$^1$ and R$^3$ are not both H.

2. The compound according to claim 1, wherein R$^1$ is OH; R$^3$ is H; and R$^2$ is H.

3. The compound according to claim 1, wherein R$^1$ and R$^3$ together form an oxo group; and R$^2$ is H.

4. The compound according to claim 1, wherein R$^1$ is H; R$^3$ is H; and R$^2$ is the group of Formula (IIa).

5. The compound according to claim 1, wherein the compound is selected from the compounds of Formula (Io) and pharmaceutically acceptable salts, solvates, and hydrates thereof:

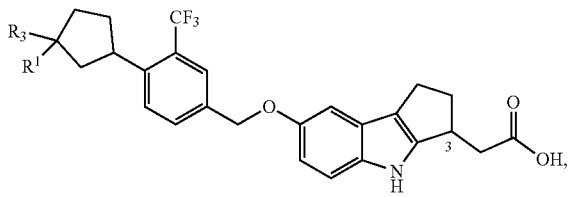

wherein:
R¹ is OH; and
R³ is H;
or R¹ and R³ together form an oxo group.

6. The compound according to claim 1, wherein the compound is selected from the compounds of Formula (Iw) and pharmaceutically acceptable salts, solvates, and hydrates thereof:

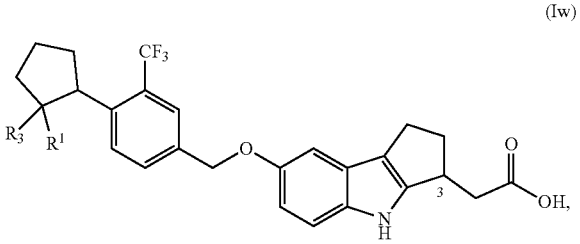

wherein:
R¹ is OH; and
R³ is H;
or R¹ and R³ together form an oxo group.

7. The compound according to claim 5, wherein R¹ is OH; and R³ is H.

8. The compound according to claim 5, wherein R¹ and R³ together form an oxo group.

9. The compound according to any one of claim 1, wherein the stereochemistry for the C(3) carbon of the 1,2,3,4-tetrahydrocyclopenta[b]indol-3-yl group is (R).

10. The compound according to any one of claim 1, wherein the stereochemistry for the C(3) carbon of the 1,2,3,4-tetrahydrocyclopenta[b]indol-3-yl group is (S).

11. A compound selected from the following compounds and pharmaceutically acceptable salts, solvates, and hydrates thereof:

(2S,3S,4S,5R)-6-(2-((R)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid;

(2S,3S,4S,5R,6S)-6-(2-((R)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid;

(2S,3S,4S,5R,6R)-6-(2-((R)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid;

(2S,3S,4S,5R)-6-(2-((S)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid;

(2S,3S,4S,5R,6S)-6-(2-((S)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid;

(2S,3S,4S,5R,6R)-6-(2-((S)-7-((4-cyclopentyl-3-(trifluoromethyl)benzyl)oxy)-1,2,3,4-tetrahydrocyclopenta[b]indol-3-yl)acetoxy)-3,4,5-trihydroxytetrahydro-2H-pyran-2-carboxylic acid;

2-(7-((4-(3-hydroxycyclopentyl)-3-(trifluoromethyl)benzyl)oxy)-1,2,3,4-tetrahydrocyclopenta[b]indol-3-yl)acetic acid;

2-((R)-7-((4-((1S,3S)-3-hydroxycyclopentyl)-3-(trifluoromethyl)benzyl)oxy)-1,2,3,4-tetrahydrocyclopenta[b]indol-3-yl)acetic acid;

2-((R)-7-((4-((1R,3R)-3-hydroxycyclopentyl)-3-(trifluoromethyl)benzyl)oxy)-1,2,3,4-tetrahydrocyclopenta[b]indol-3-yl)acetic acid;

2-((R)-7-((4-((1R,3S)-3-hydroxycyclopentyl)-3-(trifluoromethyl)benzyl)oxy)-1,2,3,4-tetrahydrocyclopenta[b]indol-3-yl)acetic acid;

2-((R)-7-((4-((1S,3R)-3-hydroxycyclopentyl)-3-(trifluoromethyl)benzyl)oxy)-1,2,3,4-tetrahydrocyclopenta[b]indol-3-yl)acetic acid;

2-((S)-7-((4-((1S,3S)-3-hydroxycyclopentyl)-3-(trifluoromethyl)benzyl)oxy)-1,2,3,4-tetrahydrocyclopenta[b]indol-3-yl)acetic acid;

2-((S)-7-((4-((1R,3R)-3-hydroxycyclopentyl)-3-(trifluoromethyl)benzyl)oxy)-1,2,3,4-tetrahydrocyclopenta[b]indol-3-yl)acetic acid;

2-((S)-7-((4-((1R,3S)-3-hydroxycyclopentyl)-3-(trifluoromethyl)benzyl)oxy)-1,2,3,4-tetrahydrocyclopenta[b]indol-3-yl)acetic acid;

2-((S)-7-((4-((1S,3R)-3-hydroxycyclopentyl)-3-(trifluoromethyl)benzyl)oxy)-1,2,3,4-tetrahydrocyclopenta[b]indol-3-yl)acetic acid;

2-(7-((4-(3-oxocyclopentyl)-3-(trifluoromethyl)benzyl)oxy)-1,2,3,4-tetrahydrocyclopenta[b]indol-3-yl)acetic acid;

2-((R)-7-((4-((S)-3-oxocyclopentyl)-3-(trifluoromethyl)benzyl)oxy)-1,2,3,4-tetrahydrocyclopenta[b]indol-3-yl)acetic acid;

2-((R)-7-((4-((R)-3-oxocyclopentyl)-3-(trifluoromethyl)benzyl)oxy)-1,2,3,4-tetrahydrocyclopenta[b]indol-3-yl)acetic acid;

2-((S)-7-((4-((S)-3-oxocyclopentyl)-3-(trifluoromethyl)benzyl)oxy)-1,2,3,4-tetrahydrocyclopenta[b]indol-3-yl)acetic acid;

2-((S)-7-((4-((R)-3-oxocyclopentyl)-3-(trifluoromethyl)benzyl)oxy)-1,2,3,4-tetrahydrocyclopenta[b]indol-3-yl)acetic acid;

2-(7-((4-(2-hydroxycyclopentyl)-3-(trifluoromethyl)benzyl)oxy)-1,2,3,4-tetrahydrocyclopenta[b]indol-3-yl)acetic acid;

2-((R)-7-((4-((1R,2S)-2-hydroxycyclopentyl)-3-(trifluoromethyl)benzyl)oxy)-1,2,3,4-tetrahydrocyclopenta[b]indol-3-yl)acetic acid;

2-((R)-7-((4-((1S,2R)-2-hydroxycyclopentyl)-3-(trifluoromethyl)benzyl)oxy)-1,2,3,4-tetrahydrocyclopenta[b]indol-3-yl)acetic acid;

2-((R)-7-((4-((1S,2S)-2-hydroxycyclopentyl)-3-(trifluoromethyl)benzyl)oxy)-1,2,3,4-tetrahydrocyclopenta[b]indol-3-yl)acetic acid;

2-((R)-7-((4-((1R,2R)-2-hydroxycyclopentyl)-3-(trifluoromethyl)benzyl)oxy)-1,2,3,4-tetrahydrocyclopenta[b]indol-3-yl)acetic acid;

2-((S)-7-((4-((1R,2S)-2-hydroxycyclopentyl)-3-(trifluoromethyl)benzyl)oxy)-1,2,3,4-tetrahydrocyclopenta[b]indol-3-yl)acetic acid;

2-((S)-7-((4-((1S,2R)-2-hydroxycyclopentyl)-3-(trifluoromethyl)benzyl)oxy)-1,2,3,4-tetrahydrocyclopenta[b]indol-3-yl)acetic acid;

2-((S)-7-((4-((1S,2S)-2-hydroxycyclopentyl)-3-(trifluoromethyl)benzyl)oxy)-1,2,3,4-tetrahydrocyclopenta[b]indol-3-yl)acetic acid;

2-((S)-7-((4-((1R,2R)-2-hydroxycyclopentyl)-3-(trifluoromethyl)benzyl)oxy)-1,2,3,4-tetrahydrocyclopenta[b]indol-3-yl)acetic acid;

2-(7-((4-(2-oxocyclopentyl)-3-(trifluoromethyl)benzyl)oxy)-1,2,3,4-tetrahydrocyclopenta[b]indol-3-yl)acetic acid;

2-((R)-7-((4-((R)-2-oxocyclopentyl)-3-(trifluoromethyl)benzyl)oxy)-1,2,3,4-tetrahydrocyclopenta[b]indol-3-yl)acetic acid;

2-((R)-7-((4-((S)-2-oxocyclopentyl)-3-(trifluoromethyl)benzyl)oxy)-1,2,3,4-tetrahydrocyclopenta[b]indol-3-yl)acetic acid;

2-((S)-7-((4-((R)-2-oxocyclopentyl)-3-(trifluoromethyl)benzyl)oxy)-1,2,3,4-tetrahydrocyclopenta[b]indol-3-yl)acetic acid;

2-((S)-7-((4-((S)-2-oxocyclopentyl)-3-(trifluoromethyl)benzyl)oxy)-1,2,3,4-tetrahydrocyclopenta[b]indol-3-yl)acetic acid;

2-(7-((4-isopropoxy-3-(trifluoromethyl)benzyl)oxy)-1,2,3,4-tetrahydrocyclopenta[b]indol-3-yl)acetic acid;

(R)-2-(7-((4-isopropoxy-3-(trifluoromethyl)benzyl)oxy)-1,2,3,4-tetrahydrocyclopenta[b]indol-3-yl)acetic acid; and (S)-2-(7-((4-isopropoxy-3-(trifluoromethyl)benzyl)oxy)-1,2,3,4-tetrahydrocyclopenta[b]indol-3-yl)acetic acid.

12. A pharmaceutical composition comprising a compound according to any one of claim 1 and a pharmaceutically acceptable carrier.

13. A method for treating an S1P1 receptor-associated disorder in an individual comprising administering to said individual in need thereof a therapeutically effective amount of a compound according to any one of claim 1.

14. A method for treating a disorder associated with the S1P1 receptor in an individual comprising administering to said individual in need thereof a therapeutically effective amount of a compound according to any one of claims 1 to 12, wherein said disorder associated with the S1P1 receptor is selected from the group consisting of: a disease or disorder mediated by lymphocytes, an autoimmune disease or disorder, an inflammatory disease or disorder, an inflammatory skin disease, cancer, psoriasis, atopic dermatitis, rheumatoid arthritis, Crohn's disease, transplant rejection, multiple sclerosis, systemic lupus erythematosus, ulcerative colitis, type I diabetes, and acne.

15. A process for preparing a composition comprising admixing a compound according to any one of claim 1 and a pharmaceutically acceptable carrier.

\* \* \* \* \*